US012606606B2

(12) United States Patent
Kurihara et al.

(10) Patent No.: US 12,606,606 B2
(45) Date of Patent: Apr. 21, 2026

(54) NUCLEIC ACID CONSTRUCT THAT ENCODES CHIMERIC RHODOPSIN

(71) Applicant: Restore Vision Inc., Tokyo (JP)

(72) Inventors: Toshihide Kurihara, Tokyo (JP); Yusaku Katada, Tokyo (JP); Kazuo Tsubota, Tokyo (JP); Hideki Kandori, Nagoya (JP)

(73) Assignee: RESTORE VISION INC., Tokyo (JP)

( * ) Notice: Subject to any disclaimer, the term of this patent is extended or adjusted under 35 U.S.C. 154(b) by 886 days.

(21) Appl. No.: 17/642,923

(22) PCT Filed: Sep. 11, 2020

(86) PCT No.: PCT/JP2020/034543
§ 371 (c)(1),
(2) Date: Mar. 14, 2022

(87) PCT Pub. No.: WO2021/049634
PCT Pub. Date: Mar. 18, 2021

(65) Prior Publication Data
US 2022/0402994 A1 Dec. 22, 2022

(30) Foreign Application Priority Data
Sep. 13, 2019 (JP) ................................. 2019-167553

(51) Int. Cl.
| | |
|---|---|
| *C07K 14/705* | (2006.01) |
| *A61K 38/17* | (2006.01) |
| *A61P 27/02* | (2006.01) |
| *A61P 27/10* | (2006.01) |
| *C07K 19/00* | (2006.01) |
| *C12N 15/62* | (2006.01) |
| *C12N 15/63* | (2006.01) |
| *C12N 15/85* | (2006.01) |
| *C12N 15/86* | (2006.01) |
| *C12N 15/861* | (2006.01) |

(52) U.S. Cl.
CPC .......... *C07K 14/705* (2013.01); *A61K 38/177* (2013.01); *A61P 27/10* (2018.01); *C07K 19/00* (2013.01); *C12N 15/62* (2013.01); *C12N 15/63* (2013.01); *C12N 15/8509* (2013.01); *C12N 15/86* (2013.01); *C12N 15/861* (2013.01); *A61P 27/02* (2018.01); *C07K 2319/01* (2013.01); *C07K 2319/02* (2013.01); *C07K 2319/33* (2013.01); *C07K 2319/43* (2013.01)

(58) Field of Classification Search
CPC .......... C07K 2319/00; C07K 2319/43; C07K 19/00; C07K 2319/01; C07K 2319/02; C07K 14/705; C12N 15/63; C12N 15/62; C12N 15/86; C12N 15/861
See application file for complete search history.

(56) References Cited

U.S. PATENT DOCUMENTS

| | | | |
|---|---|---|---|
| 7,196,175 | B2 | 3/2007 | Tamatani et al. |
| 2016/0038409 | A1 | 2/2016 | Pan et al. |
| 2019/0194294 | A1 | 6/2019 | Kurihara et al. |
| 2022/0025018 | A1 | 1/2022 | Kurihara et al. |
| 2022/0273761 | A1 | 9/2022 | Kurihara et al. |

FOREIGN PATENT DOCUMENTS

| | | |
|---|---|---|
| EP | 2547762 B1 | 4/2018 |
| EP | 3508212 A1 | 7/2019 |
| JP | H1129599 | 2/1999 |
| JP | 2009536219 | 10/2009 |
| JP | 2014500716 | 1/2014 |
| JP | 2016519063 | 6/2016 |
| KR | 101061482 B1 | 9/2011 |
| WO | WO2007131180 | 11/2007 |
| WO | WO2011030964 | 3/2011 |
| WO | WO2012061679 | 5/2012 |
| WO | WO2014160281 | 10/2014 |
| WO | WO2015138616 | 9/2015 |
| WO | WO2018043707 | 3/2019 |
| WO | WO2020148913 | 7/2020 |
| WO | WO2021049634 | 3/2022 |

OTHER PUBLICATIONS

Bhattacharya et al. Impact of genetic variation on three dimensional structure and function of proteins. PLoS ONE 12(3): e0171355, 2017.*
Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*
Conley et al. Nanoparticles for retinal gene therapy. Progress Retinal Eye Res 29: 376-397, 2010.*

(Continued)

*Primary Examiner* — Bridget E Bunner
(74) *Attorney, Agent, or Firm* — Leason Ellis LLP; James F. Haley, Jr.; Kendra V. Johnson

(57) ABSTRACT

Provided are: a nucleic acid including a nucleic acid sequence encoding a chimeric protein including at least part of an ion-transporting receptor rhodopsin and at least part of a G protein-coupled receptor rhodopsin and a nucleic acid sequence encoding a signal sequence; and a nucleic acid including a nucleic acid sequence encoding a chimeric protein including at least part of an ion channeling receptor rhodopsin and at least part of a G protein-coupled receptor rhodopsin; and a nucleic acid construct including the nucleic acid sequences. The use of the nucleic acids or nucleic acid constructs prevents and suppresses the progress of retinal diseases, and enhances the visual cognitive behavioral function and visual function.

17 Claims, 23 Drawing Sheets
Specification includes a Sequence Listing.

(56) References Cited

OTHER PUBLICATIONS

Deng et al. Age-related macular degeneration: Epidemiology, genetics, pathophysiology, diagnosis, and targeted therapy. Genes Diseases 9: 62-79, 2022.*

Doerks et al. Protein annotation: detective work for function prediction. Trends in Genetics 14:248-250, 1998.*

Einhauer et al. The FLAG peptide, a versatile fusion tag for the purification of recombinant proteins. J Biochem Biophys Methods 49 : 455-465, 2001.*

English language translation of WO 2018/042707 (Mar. 8, 2018).*

Fenton et al. Rheostat positions: a new classification of protein positions relevant to pharmacogenomics. Medicinal Chem Res 29: 1133-1146, 2020.*

Gradinaru et al. Molecular and Cellular Approaches for Diversifying and Extending Optogenetics. Cell 141: 154-165, 2010.*

Guo et al. Protein tolerance to random amino acid change. Proc Natl Acad Sci USA 101(25): 9205-9210, 2004.*

Mamedov et al. A single mutation converts bacterial Na+-transporting rhodopsin into an H+ transporter. FEBS Lett 590: 2827-2835, 2016.*

Nagata et al. Rhodopsins at a glance. J Cell Sci 134(22): jcs258989, 2021 (12 total pages).*

Ngo et al. "Computational complexity, protein structure prediction, and the Levinthal paradox" in The Protein Folding Problem and Tertiary Structure Prediction, pp. 492-495, 1994.*

Nowak et al. Age-related macular degeneration (AMD): pathogenesis and therapy. Pharmacol Reports 58: 353-363, 2006.*

Simo et al. Angiogenic and antiangiogenic factors in proliferative diabetic retinopathy. Curr Diabetes Rev 2: 71-98, 2006.*

Skolnick et al. From genes to protein structure and function: novel applications of computational approaches in the genomic era. Trends Biotechnol 18(1):34-39 2000.*

Smith et al. The challenges of genome sequence annotation or "the devil is in the details". Nature Biotechnol 15: 1222-1223, 1997.*

Tokuriki et al. Stability effects of mutations and protein evolvability. Curr Opin Structural Biol 19: 596-604, 2009.*

Wells, J.A. Additivity of mutational effects in proteins. Biochemistry 29(37): 8509-8517, 1990.*

Yu et al. Pathogenesis and intervention strategies in diabetic retinopathy. Clin Exp Ophthalmol 29: 164-166, 2001.*

Morgan, "Plasmids 101: The Promoter Region—Let's Go!," Apr. 3, 2014 (8 total pages) (https://blog.addgene.org/plasmids-101-the-promoter-region).

SignaGen Laboratories, A Gene Delivery Company, "Common promoters for eukaryotes and prokaryotes" Oct. 16, 2015 (4 total pages) (https://signagen.com/blog/2015/10/16/common-promoters-for-eukaryotes-and-prokaryotes/ ).

Altschul et al., "Basic Logal Alignment Search Tool," Journal of Molecular Biology, 215:403-410 (1990).

Batzer et al., "Enhanced evolutionary PCR using oligonucleotides with inosine at the 3'-terminus," Nucleic Acids Research, 19:5081 (1991).

Chow et al., "High-performance genetically targetable optical neural silencing by light-driven proton pumps," Nature, 463:98-102 (2010).

Dalbadie-McFarland et al., "Oligonucleotide-directed nutagenesis as a general and powerful method for studies of protein function," PNAS, 79:6409-6413 (1982).

Karlin et al., "Applications and statistics for multiple high-scoring segments in molecular sequences," PNAS, 90:5873-5877 (1993).

Li et al., "Fast noninvasive activation and inhibition of neural and network activity by vertebrate rhodopsin and green algae channelrhodopsin," PNAS, 102(49): 17816-17821 (2005).

Mark et al., "Site-specific mutagenesis of the human fibroblast interferon gene," PNAS, 81:5662-5666 (1984).

Ohtsuka et al., "An Alternative Approach to Deoxyoligonucleotides as Hybridization Probes by Insertion of Deoxyinosine at Ambiguous Codon Positions," Journal of Biological Chemistry, 260(5): 2605-2608 (1985).

Rossolini et al., "Use of deoxyinosine-containing primers vs degenerate primers for polymerase chain reaction based on ambiguous sequence information," Molecular and Cellular Probes, 8:91-98 (1994).

Stockklausner et al., "A sequence motif responsible for ER export and surface expression of Kir2.0 inward rectifier $K^+$ channels", FEBS Letters, 493: 129-133 (2001).

Wang, A. et al., "Site-Specific Mutagenesis of the Human Interleukin-2 Gene: Structure-Function Analysis of the Cysteine Residues," Science 224(4656):1431-1433 (1984).

Zoller et al., "Oligonucleotide-directed mutagenesis using M13-derived vectors: an efficient and general procedure for the production of point mutations in any fragment of DNA," Nucleic Acids Research, 10(20):6487-6500 (1982).

Bi, et al., "Ectopic Expression of a Microbial-Type Rhodopsin Restores Visual Responses in Mice with Photoreceptor Degeneration", Neuron 50(1): 23-33 (2006).

European Supplementary Search Report, dated Apr. 20, 2020, issued in EP Pat. App. No. 17846710.6 (10 pages).

Granovsky, et al., "Objective correlate of subjective pain perception by contact heat-evoked potentials," The Journal of Pain 9(1): 53-63 (2008).

Huang, et al., "A novel approach to predict subjective pain perception from single-trial laser-evoked potentials", Neuroimage 81: 283-293 (2013).

Japanese First Office Action, dated Jul. 29, 2019, issued in JP Pat. App. No. 2018-537436 (12 pages).

Japanese Final Office Action, dated Jan. 6, 2020, issued in JP Pat. App. No. 2018-537436 (8 pages).

Katada, et al., "Study on effect of reconstructing vision using chimeric rhodopsin," The 122nd Annual Meeting of the Japanese Ophthalmological Society, Abstract (2018).

Katada, et al., "Study on effect of reconstructing vision using chimeric rhodopsin," The 122nd Annual Meeting of the Japanese Ophthalmological Society, Poster (Apr. 2018).

Katada, et al., "Study on effect of reconstructing vision using chimeric rhodopsin," The 122nd Annual Meeting of the Japanese Ophthalmological Society, Short Title List (Apr. 2018).

Katada, et al., "Study on effect of reconstructing vision using chimeric rhodopsin", Journal of the Japanese Ophthalmological Society 122: 259 (Mar. 9, 2018).

Kurihara, "From algae to humans: Challenge to transcendental retinal treatment", The 72nd Annual Congress of Japan Clinical Ophthalmology at Tokyo International Forum (Oct. 12, 2018).

Kurihara, Institute for Protein Research, Osaka University Seminar: Frontiers of Sensory research in Retina (Jan. 20, 2018).

Kurihara, "Visual restoration utilizing optogenetics for retinal degeneration", Journal of Japanese Ophthalmological Society 123: 55 (2019).

Restriction Requirement, dated Oct. 8, 2021, issued in U.S. Appl. No. 16/329,631 (7 pages).

Sasaki, et al., "Chimeric proton-pumping rhodopsins containing the cytoplasmic loop of bovine rhodopsin", PLOS ONE 9(3): 1-12, e91323 (2014).

Scientific Research on Innovative Areas "Soft Molecular Systems" Newsletter No. 8, Apr. 2014, Kazuho Yoshida "Function of chimeric protein of animal rhodopsin and microbial rhodopsin," Journal vol. No. PLOS One 9, e91323 (2014).

Tomita, et al., "Restoration of the majority of the visual spectrum by using modified Volvox channelrhodopsin-1", American Society of Gene & Cell Therapy 22(8): 1434-1440 (2014).

Zhao et al., "Improved expression of halorhodopsin for light-induced silencing of neuronal activity," Brain Cell Biology, 36:141-154 (2008).

Rost, "Optogenetic Tools for Subcellular Applications in Neuroscience," Neuron, Nov. 1, 2017, 96(3):572-603.

* cited by examiner

MEA results with the first nucleic acid construct

Figure 2B

MEA results with the first nucleic acid construct

MEA results with the nucleic acid construct of the present disclosure

Figure 3C

MEA results with the nucleic acid construct of the present disclosure

Figure 13

Comparison of Amount of Change with and without Light Irradiation n=11, each

One-way ANOVA with Tukey (* P < 0.01).

SEQUENCE LISTING

```
<160> NUMBER OF SEQ ID NOS: 27

<210> SEQ ID NO 1
<211> LENGTH: 1078
<212> TYPE: DNA
<213> ORGANISM: artificial sequence
<220> FEATURE:
<223> OTHER INFORMATION: An example of nucleic acid sequence consisting
      of chimera rhodopsin (GR/BvRh) and ER export signal

<400> SEQUENCE: 1
ctggatccga tatcaagctt gccaccatgc tgatgaccgt gttcagcagc gccctgagc       60 tggccctgct gggctctaca tttgcccagg tggaccccag caacctgagc gtgtccgaca      120
gcctgaccta cggccagttc aacctggtgt acaacgcctt cagcttcgcc attgccgcca      180
tgttcgccag cgccctgttc ttcttcagtg cacaagccct cgtgggccag cggtacagac      240
tggctctgct ggtgtctgcc atcgtggtgt ctatcgccgg ctaccactac ttccggatct      300
tcaacagctg ggacgccgcc tacgtgctgg aaaacggcgt gtactccctg accagcgaga      360
agttcaacga cgcctacaga tacgtggact ggctgctgac cgtgcccctg ctgctggtgc      420
aaacagtggc cgtgatcgag cgctacgtgg tcgtgtgcaa gcccatgagc aacttcagat      480
tcggcgagaa ccaccccctg ctgatcaagc tgacagtggc cagcgtgctg atgatcgcca      540
caggctaccc tggcgagatc agcgacgaca tcaccacccg gatcatctgg ggaaccgtgt      600
ccaccatccc cttcgcctac atcctgtacg tgctgtgggt ggaactgagc ttcaccgtga      660
aagaggccgc tgctcagcag caggaaagcg ccacaaccca ggtgcagacc ctcgtgcgga      720
acatgagatg gttgctgctg ctgtcctggg gcgtgtaccc tatcgcctac ctgctgccta      780
tgctgggcgt gtccggaaca tctgccgctg tgggagtgca agtgggctac acaatcgccg      840
atgtgctggc caagcccgtg ttcggcctgc tggtgttcgc tatcgccctc gtgaaaacaa      900
aggccgacca ggaaagcagc gagccccacg ccgctattgg agccgccgct aacaagtctg      960
gcggcagcct gatcagcgga tccgccagcg ccagcaacgg cgccagcgaa ttcttctgct     1020
acgagaatga agtgtaatct agcgagctcc tcgagtaatc aacctctgga ttacaaaa      1078

<210> SEQ ID NO 2
<211> LENGTH: 336
<212> TYPE: PRT
<213> ORGANISM: artificial sequence
<220> FEATURE:
<223> OTHER INFORMATION: An example of amino acid sequence consisting of
      chimera rhodopsin (GR/BvRh) and ER export signal
```

```
<400> SEQUENCE: 2

Met Leu Met Thr Val Phe Ser Ser Ala Pro Glu Leu Ala Leu Leu Gly
1               5                   10                  15

Ser Thr Phe Ala Gln Val Asp Pro Ser Asn Leu Ser Val Ser Asp Ser
            20                  25                  30

Leu Thr Tyr Gly Gln Phe Asn Leu Val Tyr Asn Ala Phe Ser Phe Ala
        35                  40                  45

Ile Ala Ala Met Phe Ala Ser Ala Leu Phe Phe Phe Ser Ala Gln Ala
    50                  55                  60

Leu Val Gly Gln Arg Tyr Arg Leu Ala Leu Leu Val Ser Ala Ile Val
65                  70                  75                  80

Val Ser Ile Ala Gly Tyr His Tyr Phe Arg Ile Phe Asn Ser Trp Asp
                85                  90                  95

Ala Ala Tyr Val Leu Glu Asn Gly Val Tyr Ser Leu Thr Ser Glu Lys
                100                 105                 110

Phe Asn Asp Ala Tyr Arg Tyr Val Asp Trp Leu Leu Thr Val Pro Leu
            115                 120                 125

Leu Leu Val Gln Thr Val Ala Val Ile Glu Arg Tyr Val Val Val Cys
        130                 135                 140

Lys Pro Met Ser Asn Phe Arg Phe Gly Glu Asn His Pro Leu Leu Ile
145                 150                 155                 160

Lys Leu Thr Val Ala Ser Val Leu Met Ile Ala Thr Gly Tyr Pro Gly
                165                 170                 175

Glu Ile Ser Asp Asp Ile Thr Thr Arg Ile Ile Trp Gly Thr Val Ser
                180                 185                 190

Thr Ile Pro Phe Ala Tyr Ile Leu Tyr Val Leu Trp Val Glu Leu Ser
            195                 200                 205

Phe Thr Val Lys Glu Ala Ala Ala Gln Gln Gln Glu Ser Ala Thr Thr
    210                 215                 220

Gln Val Gln Thr Leu Val Arg Asn Met Arg Trp Leu Leu Leu Leu Ser
225                 230                 235                 240

Trp Gly Val Tyr Pro Ile Ala Tyr Leu Leu Pro Met Leu Gly Val Ser
                245                 250                 255

Gly Thr Ser Ala Ala Val Gly Val Gln Val Gly Tyr Thr Ile Ala Asp
            260                 265                 270

Val Leu Ala Lys Pro Val Phe Gly Leu Leu Val Phe Ala Ile Ala Leu
        275                 280                 285

Val Lys Thr Lys Ala Asp Gln Glu Ser Ser Glu Pro His Ala Ala Ile
    290                 295                 300

Gly Ala Ala Ala Asn Lys Ser Gly Gly Ser Leu Ile Ser Gly Ser Ala
305                 310                 315                 320

Ser Ala Ser Asn Gly Ala Ser Glu Phe Phe Cys Tyr Glu Asn Glu Val
                325                 330                 335

<210> SEQ ID NO 3
<211> LENGTH: 1102
<212> TYPE: DNA
<213> ORGANISM: artificial sequence
<220> FEATURE:
<223> OTHER INFORMATION: An example of nucleic acid sequence consisting
      of chimera rhodopsin (GR/BvRh), ER export signal and FLAG tag

<400> SEQUENCE: 3
ctggatccga tatcaagctt gccaccatgc tgatgaccgt gttcagcagc gcccctgagc      60
tggccctgct gggctctaca tttgcccagg tggaccccag caacctgagc gtgtccgaca     120
```

-continued

```
gcctgaccta cggccagttc aacctggtgt acaacgcctt cagcttcgcc attgccgcca          180
tgttcgccag cgccctgttc ttcttcagtg cacaagccct cgtgggccag cggtacagac          240
tggctctgct ggtgtctgcc atcgtggtgt ctatcgccgg ctaccactac ttccggatct          300
tcaacagctg ggacgccgcc tacgtgctgg aaaacggcgt gtactccctg accagcgaga          360
agttcaacga cgcctacaga tacgtggact ggctgctgac cgtgcccctg ctgctggtgc          420
aaacagtggc cgtgatcgag cgctacgtgg tcgtgtgcaa gcccatgagc aacttcagat          480
tcggcgagaa ccaccccctg ctgatcaagc tgacagtggc cagcgtgctg atgatcgcca          540
caggctaccc tggcgagatc agcgacgaca tcaccacccg gatcatctgg ggaaccgtgt          600
ccaccatccc cttcgcctac atcctgtacg tgctgtgggt ggaactgagc ttcaccgtga          660
aagaggccgc tgctcagcag caggaaagcg ccacaaccca ggtgcagacc ctcgtgcgga          720
acatgagatg gttgctgctg ctgtcctggg gcgtgtaccc tatcgcctac ctgctgccta          780
tgctgggcgt gtccggaaca tctgccgctg tgggagtgca agtgggctac acaatcgccg          840
atgtgctggc caagcccgtg ttcggcctgc tggtgttcgc tatcgccctc gtgaaaacaa          900
aggccgacca ggaaagcagc gagccccacg ccgctattgg agccgccgct aacaagtctg          960
gcggcagcct gatcagcgga tccgccagcg ccagcaacgg cgccagcgac tacaaagacg         1020
atgacgacaa ggaattcttc tgctacgaga tgaagtgta atctagcgag ctcctcgagt         1080
aatcaacctc tggattacaa aa                                                 1102
```

<210> SEQ ID NO 4
<211> LENGTH: 344
<212> TYPE: PRT
<213> ORGANISM: artificial sequence
<220> FEATURE:
<223> OTHER INFORMATION: An example of amino acid sequence consisting of
     chimera rhodopsin (GR/BvRh), ER export signal and FLAG tag

<400> SEQUENCE: 4

```
Met Leu Met Thr Val Phe Ser Ser Ala Pro Glu Leu Ala Leu Leu Gly
1               5                   10                  15

Ser Thr Phe Ala Gln Val Asp Pro Ser Asn Leu Ser Val Ser Asp Ser
            20                  25                  30

Leu Thr Tyr Gly Gln Phe Asn Leu Val Tyr Asn Ala Phe Ser Phe Ala
        35                  40                  45

Ile Ala Ala Met Phe Ala Ser Ala Leu Phe Phe Phe Ser Ala Gln Ala
    50                  55                  60

Leu Val Gly Gln Arg Tyr Arg Leu Ala Leu Leu Val Ser Ala Ile Val
65                  70                  75                  80

Val Ser Ile Ala Gly Tyr His Tyr Phe Arg Ile Phe Asn Ser Trp Asp
                85                  90                  95

Ala Ala Tyr Val Leu Glu Asn Gly Val Tyr Ser Leu Thr Ser Glu Lys
            100                 105                 110

Phe Asn Asp Ala Tyr Arg Tyr Val Asp Trp Leu Leu Thr Val Pro Leu
        115                 120                 125

Leu Leu Val Gln Thr Val Ala Val Ile Glu Arg Tyr Val Val Val Cys
    130                 135                 140

Lys Pro Met Ser Asn Phe Arg Phe Gly Glu Asn His Pro Leu Leu Ile
145                 150                 155                 160

Lys Leu Thr Val Ala Ser Val Leu Met Ile Ala Thr Gly Tyr Pro Gly
                165                 170                 175
```

-continued

```
Glu Ile Ser Asp Asp Ile Thr Thr Arg Ile Ile Trp Gly Thr Val Ser
            180                 185                 190

Thr Ile Pro Phe Ala Tyr Ile Leu Tyr Val Leu Trp Val Glu Leu Ser
            195                 200                 205

Phe Thr Val Lys Glu Ala Ala Ala Gln Gln Gln Glu Ser Ala Thr Thr
            210                 215                 220

Gln Val Gln Thr Leu Val Arg Asn Met Arg Trp Leu Leu Leu Leu Ser
225                 230                 235                 240

Trp Gly Val Tyr Pro Ile Ala Tyr Leu Leu Pro Met Leu Gly Val Ser
                245                 250                 255

Gly Thr Ser Ala Ala Val Gly Val Gln Val Gly Tyr Thr Ile Ala Asp
            260                 265                 270

Val Leu Ala Lys Pro Val Phe Gly Leu Leu Val Phe Ala Ile Ala Leu
            275                 280                 285

Val Lys Thr Lys Ala Asp Gln Glu Ser Ser Glu Pro His Ala Ala Ile
            290                 295                 300

Gly Ala Ala Ala Asn Lys Ser Gly Gly Ser Leu Ile Ser Gly Ser Ala
305                 310                 315                 320

Ser Ala Ser Asn Gly Ala Ser Asp Tyr Lys Asp Asp Asp Lys Glu
                325                 330                 335

Phe Phe Cys Tyr Glu Asn Glu Val
            340
```

```
<210> SEQ ID NO 5
<211> LENGTH: 317
<212> TYPE: PRT
<213> ORGANISM: artificial sequence
<220> FEATURE:
<223> OTHER INFORMATION: An example of amino acid sequence encoding
      chimera rhodopsin (GR/BvRh)

<400> SEQUENCE: 5
```

```
Met Leu Met Thr Val Phe Ser Ser Ala Pro Glu Leu Ala Leu Leu Gly
1               5                   10                  15

Ser Thr Phe Ala Gln Val Asp Pro Ser Asn Leu Ser Val Ser Asp Ser
            20                  25                  30

Leu Thr Tyr Gly Gln Phe Asn Leu Val Tyr Asn Ala Phe Ser Phe Ala
            35                  40                  45

Ile Ala Ala Met Phe Ala Ser Ala Leu Phe Phe Phe Ser Ala Gln Ala
    50                  55                  60

Leu Val Gly Gln Arg Tyr Arg Leu Ala Leu Leu Val Ser Ala Ile Val
65                  70                  75                  80

Val Ser Ile Ala Gly Tyr His Tyr Phe Arg Ile Phe Asn Ser Trp Asp
                85                  90                  95

Ala Ala Tyr Val Leu Glu Asn Gly Val Tyr Ser Leu Thr Ser Glu Lys
            100                 105                 110

Phe Asn Asp Ala Tyr Arg Tyr Val Asp Trp Leu Leu Thr Val Pro Leu
            115                 120                 125

Leu Leu Val Gln Thr Val Ala Val Ile Glu Arg Tyr Val Val Val Cys
            130                 135                 140

Lys Pro Met Ser Asn Phe Arg Phe Gly Glu Asn His Pro Leu Leu Ile
145                 150                 155                 160

Lys Leu Thr Val Ala Ser Val Leu Met Ile Ala Thr Gly Tyr Pro Gly
                165                 170                 175

Glu Ile Ser Asp Asp Ile Thr Thr Arg Ile Ile Trp Gly Thr Val Ser
            180                 185                 190
```

-continued

```
Thr Ile Pro Phe Ala Tyr Ile Leu Tyr Val Leu Trp Val Glu Leu Ser
        195               200               205

Phe Thr Val Lys Glu Ala Ala Ala Gln Gln Gln Glu Ser Ala Thr Thr
        210               215               220

Gln Val Gln Thr Leu Val Arg Asn Met Arg Trp Leu Leu Leu Leu Ser
225               230               235               240

Trp Gly Val Tyr Pro Ile Ala Tyr Leu Leu Pro Met Leu Gly Val Ser
                245               250               255

Gly Thr Ser Ala Ala Val Gly Val Gln Val Gly Tyr Thr Ile Ala Asp
                260               265               270

Val Leu Ala Lys Pro Val Phe Gly Leu Leu Val Phe Ala Ile Ala Leu
        275               280               285

Val Lys Thr Lys Ala Asp Gln Glu Ser Ser Glu Pro His Ala Ala Ile
        290               295               300

Gly Ala Ala Ala Asn Lys Ser Gly Gly Ser Leu Ile Ser
305               310               315
```

```
<210> SEQ ID NO 6
<211> LENGTH: 939
<212> TYPE: DNA
<213> ORGANISM: artificial sequence
<220> FEATURE:
<223> OTHER INFORMATION: An example of nucleic acid sequence encoding
      chimera rhodopsin (GtACR2/BvRh)

<400> SEQUENCE: 6
aagcttatgg ccagccaggt ggtgtacggc gagtgggcct ctacccacac cgagtgctac      60
aacatgagcc ggatcgacag caccttcgtg tccctgctgc agctcgtgtg ggccgtggtg     120
tctggctgtc agaccatctt catgatcagc agagccccca aggtgccctg ggagagcgtg     180
tacctgccct tcgtggaatc catcacctac gccctggcca gcaccggcaa tggcacactg     240
cagatgcggg acgccggtt cttcccttgg tcacggatgg cctcttggct gtgcacctgt      300
cccatcatgc tgggccagat cagcaacatg atcgagagat acgtggtcgt gtgcaagccc     360
atgagcaact tcagattcgg cgagaaccac atcccctga accctattgc ccaggccgcc      420
agcatcatcc gggtcgtgat gggcatcacc gccaccatta gccctgccga gtatatgaag     480
tggctgttct tcttcttcgg cgccacctgt ctggtgttcg agtacagcgt ggtgttcacc     540
atcttccaag tgggcctgtt caccgtgaaa gaggccgctg cccagcagca ggaaagcgcc     600
acaacacagg cccagaaagt ggtcgtgcgg atcaagatgc tgcggctgat cttctttatc     660
gcctggacca tgttccccat cgtgtggctg atctccccca ccggcgtgtg cgtgatccac     720
gagaatgtgt ccgccatcct gtacctgctg gccgacggcc tgtgcaagaa cacctacggc     780
gtgatcctgt ggtccaccgc ctggggagtg ctggaaggca atgggaccc tgcctgtctg      840 cccggccagg aaaaacctga ggccgacgat cccttcggcc tgaaccacga gaagaacgcc     900
cctcccaacg acgaagtgaa catcagaatg ttcggcagg                            939
```

```
<210> SEQ ID NO 7
<211> LENGTH: 1374
<212> TYPE: DNA
<213> ORGANISM: artificial sequence
<220> FEATURE:
<223> OTHER INFORMATION: An example of nucleic acid sequence encoding
      chimera rhodopsin (GtACR2/BvRh)

<400> SEQUENCE: 7
```

-continued

```
atggcaagcc aagtcgttta tggagaatgg gcgagtacgc atacagaatg ttacaacatg      60
tcaaggatcg acagcacctt tgtctcattg ctgcagctgg tctgggctgt tgtcagcgga     120
tgccagacga tctttatgat ctctcgagcc ccgaaggtgc catgggaatc tgtttacctt     180
cccttcgttg aaagcatcac ctatgccctc gcttctactg aaacggcac gttgcagatg      240 agggacgggc gcttctttcc ttggtcgcgc atggcatcct ggttgtgcac ttgccctatc     300
atgctcgggc agatcagcaa catgatcgag cggtacgtag tggtgtgcaa gcccatgagc     360
aacttccgct cgggggagaa cccacatcccg ttgaatccca tcgcgcaagc agcctccatc    420
atccgagtgg tgatgggaat cacggcgact atctctcccg ccgagtacat gaagtggctc     480
tttttcttct tcgggggccac gtgcctggtc tttgagtact cagttgtctt caccatcttt    540
caagtcgggc tgttcaccgt caaggaggct gcagcccagc agcaggagtc ggccaccact     600
caggctcaga aggtggtggt gagaatcaag atgctcagac tcatcttctt catcgcatgg     660
accatgttcc ccatcgtatg gctgatatcc cccactggcg tctgcgtcat tcatgagaac     720
gtgagcgcta tcctgtacct cctcgccgac gggctctgca agaacaccta cggagtgatc     780
ctgtggagca cggcatgggg cgtgttggaa gggaagtggg accctgcatg ccttccagga     840
caggagaagc cggaggccga cgatccgttt gggctgaacc atgagaagaa tgctcccccc     900
aacgatgaag tcaacatccg gatgttcgga gtcatcggct cggtgaggaa gtcaaagagg     960
aggcagaagt gggagctggc gccggcgcat ctagaggaca ggatcaggtt gagcgacgag    1020
gagtcggatg actcgaggcc gaagaggaag aagaaaggag acgcgcggga ctacaggagg    1080
aagcatcgag gaggcgccga cgacgacgat catcacagca gcgaatcgga gagtgagaag    1140
aagaacaagg gaaagaagaa gaagtcgggc aagggaaaga agaaggacga ctcgggctcc    1200
gaggacgatc ttgaggtcgg caacgggaag gcgaagaacg gagacaagca ggagttcaac    1260
gacatcaaca agatcctacg agccatgaag agaaacgccg ggacgctgag cgaaaagtct    1320
cattccgatg actccgaggg aaagcgtgag agcgcggatc attccatgtg ctga          1374
```

<210> SEQ ID NO 8
<211> LENGTH: 311
<212> TYPE: PRT
<213> ORGANISM: Artificial Sequence
<220> FEATURE:
<223> OTHER INFORMATION: An example of amino acid sequence encoding
      chimera rhodopsin (GtACR2/BvRh)

<400> SEQUENCE: 8

```
Met Ala Ser Gln Val Val Tyr Gly Glu Trp Ala Ser Thr His Thr Glu
1               5                   10                  15

Cys Tyr Asn Met Ser Arg Ile Asp Ser Thr Phe Val Ser Leu Leu Gln
            20                  25                  30

Leu Val Trp Ala Val Val Ser Gly Cys Gln Thr Ile Phe Met Ile Ser
        35                  40                  45

Arg Ala Pro Lys Val Pro Trp Glu Ser Val Tyr Leu Pro Phe Val Glu
    50                  55                  60

Ser Ile Thr Tyr Ala Leu Ala Ser Thr Gly Asn Gly Thr Leu Gln Met
65                  70                  75                  80

Arg Asp Gly Arg Phe Phe Pro Trp Ser Arg Met Ala Ser Trp Leu Cys
                85                  90                  95

Thr Cys Pro Ile Met Leu Gly Gln Ile Ser Asn Met Ile Glu Arg Tyr
            100                 105                 110

Val Val Val Cys Lys Pro Met Ser Asn Phe Arg Phe Gly Glu Asn His
```

```
          115                  120                  125
Ile Pro Leu Asn Pro Ile Ala Gln Ala Ala Ser Ile Ile Arg Val Val
    130                  135                  140
Met Gly Ile Thr Ala Thr Ile Ser Pro Ala Glu Tyr Met Lys Trp Leu
145                  150                  155                  160
Phe Phe Phe Phe Gly Ala Thr Cys Leu Val Phe Glu Tyr Ser Val Val
                165                  170                  175
Phe Thr Ile Phe Gln Val Gly Leu Phe Thr Val Lys Glu Ala Ala Ala
            180                  185                  190
Gln Gln Gln Glu Ser Ala Thr Thr Gln Ala Gln Lys Val Val Val Arg
        195                  200                  205
Ile Lys Met Leu Arg Leu Ile Phe Phe Ile Ala Trp Thr Met Phe Pro
    210                  215                  220
Ile Val Trp Leu Ile Ser Pro Thr Gly Val Cys Val Ile His Glu Asn
225                  230                  235                  240
Val Ser Ala Ile Leu Tyr Leu Leu Ala Asp Gly Leu Cys Lys Asn Thr
                245                  250                  255
Tyr Gly Val Ile Leu Trp Ser Thr Ala Trp Gly Val Leu Glu Gly Lys
            260                  265                  270
Trp Asp Pro Ala Cys Leu Pro Gly Gln Glu Lys Pro Glu Ala Asp Asp
        275                  280                  285
Pro Phe Gly Leu Asn His Glu Lys Asn Ala Pro Pro Asn Asp Glu Val
    290                  295                  300
Asn Ile Arg Met Phe Gly Arg
305                  310
```

```
<210> SEQ ID NO 9
<211> LENGTH: 1047
<212> TYPE: DNA
<213> ORGANISM: Homo sapiens

<400> SEQUENCE: 9
atgaatggca cagaaggccc taacttctac gtgcccttct ccaatgcgac gggtgtggta      60
cgcagcccct tcgagtaccc acagtactac ctggctgagc catggcagtt ctccatgctg     120
gccgcctaca tgtttctgct gatcgtgctg ggcttcccca tcaacttcct cacgctctac     180
gtcaccgtcc agcacaagaa gctgcgcacg cctctcaact acatcctgct caacctagcc     240
gtggctgacc tcttcatggt cctaggtggc ttcaccagca ccctctacac ctctctgcat     300
ggatacttcg tcttcgggcc cacaggatgc aatttggagg gcttctttgc caccctgggc     360
ggtgaaattg ccctgtggtc cttggtggtc ctggccatcg agcggtacgt ggtggtgtgt     420
aagcccatga gcaacttccg cttcggggag aaccatgcca tcatgggcgt tgccttcacc     480
tgggtcatgg cgctggcctg cgccgcaccc ccactcgccg gctggtccag gtacatcccc     540
gagggcctgc agtgctcgtg tggaatcgac tactacacgc tcaagccgga ggtcaacaac     600
gagtcttttg tcatctacat gttcgtggtc cacttcacca tccccatgat tatcatcttt     660
ttctgctatg ggcagctcgt cttcaccgtc aaggaggccg ctgcccagca gcaggagtca     720
gccaccacac agaaggcaga gaaggaggtc acccgcatgg tcatcatcat ggtcatcgct     780
ttcctgatct gctgggtgcc ctacgccagc gtggcattct acatcttcac ccaccagggc     840
tccaacttcg tcccatcttc catgaccatc ccagcgttct tgccaagag cgccgccatc     900 tacaaccctg tcatctatat catgatgaac aagcagttcc ggaactgcat gctcaccacc     960
atctgctgcg gcaagaaccc actgggtgac gatgaggcct ctgctaccgt gtccaagacg    1020
```

-continued gagacgagcc aggtggcccc ggcctaa                                                    1047

<210> SEQ ID NO 10
<211> LENGTH: 348
<212> TYPE: PRT
<213> ORGANISM: Homo sapiens

<400> SEQUENCE: 10

Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr Leu Ala
                20                  25                  30

Glu Pro Trp Gln Phe Ser Met Leu Ala Ala Tyr Met Phe Leu Leu Ile
            35                  40                  45

Val Leu Gly Phe Pro Ile Asn Phe Leu Thr Leu Tyr Val Thr Val Gln
        50                  55                  60

His Lys Lys Leu Arg Thr Pro Leu Asn Tyr Ile Leu Leu Asn Leu Ala
65                  70                  75                  80

Val Ala Asp Leu Phe Met Val Leu Gly Gly Phe Thr Ser Thr Leu Tyr
                85                  90                  95

Thr Ser Leu His Gly Tyr Phe Val Phe Gly Pro Thr Gly Cys Asn Leu
                100                 105                 110

Glu Gly Phe Phe Ala Thr Leu Gly Gly Glu Ile Ala Leu Trp Ser Leu
            115                 120                 125

Val Val Leu Ala Ile Glu Arg Tyr Val Val Val Cys Lys Pro Met Ser
        130                 135                 140

Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Ala Gly Trp Ser
                165                 170                 175

Arg Tyr Ile Pro Glu Gly Leu Gln Cys Ser Cys Gly Ile Asp Tyr Tyr
                180                 185                 190

Thr Leu Lys Pro Glu Val Asn Asn Glu Ser Phe Val Ile Tyr Met Phe
            195                 200                 205

Val Val His Phe Thr Ile Pro Met Ile Ile Ile Phe Phe Cys Tyr Gly
        210                 215                 220

Gln Leu Val Phe Thr Val Lys Glu Ala Ala Ala Gln Gln Gln Glu Ser
225                 230                 235                 240

Ala Thr Thr Gln Lys Ala Glu Lys Glu Val Thr Arg Met Val Ile Ile
                245                 250                 255

Met Val Ile Ala Phe Leu Ile Cys Trp Val Pro Tyr Ala Ser Val Ala
                260                 265                 270

Phe Tyr Ile Phe Thr His Gln Gly Ser Asn Phe Gly Pro Ile Phe Met
            275                 280                 285

Thr Ile Pro Ala Phe Phe Ala Lys Ser Ala Ala Ile Tyr Asn Pro Val
        290                 295                 300

Ile Tyr Ile Met Met Asn Lys Gln Phe Arg Asn Cys Met Leu Thr Thr
305                 310                 315                 320

Ile Cys Cys Gly Lys Asn Pro Leu Gly Asp Asp Glu Ala Ser Ala Thr
                325                 330                 335

Val Ser Lys Thr Glu Thr Ser Gln Val Ala Pro Ala
                340                 345

<210> SEQ ID NO 11

```
<211> LENGTH: 1047
<212> TYPE: DNA
<213> ORGANISM: Bos taurus

<400> SEQUENCE: 11
atgaacggga ccgagggccc aaacttctac gtgcctttct ccaacaagac gggcgtggtg      60
cgcagcccct tcgaggcccc gcagtactac ctggcggagc catggcagtt ctccatgctg     120
gccgcctaca tgttcctgct gatcatgctt ggcttcccca tcaacttcct cacgctgtac     180
gtcacagtcc agcacaagaa gctgcgcaca cccctcaact acatcctgct caacctggcc     240
gtggccgacc tcttcatggt cttcgggggc ttcaccacca ccctctacac ctctctgcac     300
ggatacttcg tctttgggcc cacgggctgc aacctggagg gcttctttgc caccctgggc     360
ggtgaaattg cactgtggtc cttggtggtc ctggccatcg agcggtacgt ggtggtgtgc     420
aagcccatga gcaacttccg cttcgggggag aaccacgcca tcatgggcgt cgccttcacc     480
tgggtcatgg ctctggcctg tgccgcgccc cccctcgtcg gctggtccag gtacatcccg     540
gagggcatgc agtgctcgtg cgggattgac tactacacgc cccacgagga gaccaacaat     600
gagtcgttcg tcatctacat gttcgtggtc cacttcatca tccccctgat tgtcatattc     660
ttctgctacg ggcagctggt gttcaccgtc aaggaggcgg ctgcccagca gcaggagtcg     720
gccaccactc agaaggccga gaaggaggtc acccgcatgg tgatcatcat ggtcatcgct     780
ttcctaatct gctggctgcc ctacgctggg gtggcgttct acatcttcac ccatcagggc     840
tctgactttg gccccatctt catgaccatc ccggctttct tgccaagac ttctgccgtc      900 tacaaccccg tcatctacat catgatgaac aagcagttcc ggaactgcat ggtcaccact     960
ctctgctgtg caagaacccc gctgggtgac gacgaggcct ccaccaccgt ctccaagaca    1020
gagaccagcc aggtggcgcc tgcctaa                                        1047

<210> SEQ ID NO 12
<211> LENGTH: 348
<212> TYPE: PRT
<213> ORGANISM: Bos taurus

<400> SEQUENCE: 12

Met Asn Gly Thr Glu Gly Pro Asn Phe Tyr Val Pro Phe Ser Asn Lys
1               5                   10                  15

Thr Gly Val Val Arg Ser Pro Phe Glu Ala Pro Gln Tyr Tyr Leu Ala
                20                  25                  30

Glu Pro Trp Gln Phe Ser Met Leu Ala Ala Tyr Met Phe Leu Leu Ile
            35                  40                  45

Met Leu Gly Phe Pro Ile Asn Phe Leu Thr Leu Tyr Val Thr Val Gln
        50                  55                  60

His Lys Lys Leu Arg Thr Pro Leu Asn Tyr Ile Leu Leu Asn Leu Ala
65                  70                  75                  80

Val Ala Asp Leu Phe Met Val Phe Gly Gly Phe Thr Thr Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Val Cys Lys Pro Met Ser
    130                 135                 140

Asn Phe Arg Phe Gly Glu Asn His Ala Ile Met Gly Val Ala Phe Thr
145                 150                 155                 160
```

-continued

Trp Val Met Ala Leu Ala Cys Ala Ala Pro Pro Leu Val Gly Trp Ser
                165                 170                 175

Arg Tyr Ile Pro Glu Gly Met Gln Cys Ser Cys Gly Ile Asp Tyr Tyr
            180                 185                 190

Thr Pro His Glu Glu Thr Asn Asn Glu Ser Phe Val Ile Tyr Met Phe
        195                 200                 205

Val Val His Phe Ile Ile Pro Leu Ile Val Ile Phe Phe Cys Tyr Gly
    210                 215                 220

Gln Leu Val Phe Thr Val Lys Glu Ala Ala Ala Gln Gln Gln Glu Ser
225                 230                 235                 240

Ala Thr Thr Gln Lys Ala Glu Lys Glu Val Thr Arg Met Val Ile Ile
                245                 250                 255

Met Val Ile Ala Phe Leu Ile Cys Trp Leu Pro Tyr Ala Gly Val Ala
                260                 265                 270

Phe Tyr Ile Phe Thr His Gln Gly Ser Asp Phe Gly Pro Ile Phe Met
            275                 280                 285

Thr Ile Pro Ala Phe Phe Ala Lys Thr Ser Ala Val Tyr Asn Pro Val
        290                 295                 300

Ile Tyr Ile Met Met Asn Lys Gln Phe Arg Asn Cys Met Val Thr Thr
305                 310                 315                 320

Leu Cys Cys Gly Lys Asn Pro Leu Gly Asp Asp Glu Ala Ser Thr Thr
                325                 330                 335

Val Ser Lys Thr Glu Thr Ser Gln Val Ala Pro Ala
            340                 345

<210> SEQ ID NO 13
<211> LENGTH: 897
<212> TYPE: DNA
<213> ORGANISM: Gloeobacter violaceus

<400> SEQUENCE: 13
atgttgatga ccgtattttc ttctgcacct gaacttgccc ttctcggatc aacctttgcc        60
caggtcgatc cttcaaactt atcggtctca gattcgctga cctatggtca gttcaatctg       120
gtttacaacg ctttctcgtt tgccatcgcg gcaatgttcg catctgccct cttcttcttc       180
agcgctcagg cactcgtcgg tcaacgatac cggttggcct tgcttgtttc agcaattgtt       240
gtgagtatcg ctgggtacca ctactttcgg atcttcaata gttgggatgc tgcctacgtt       300
ctggagaatg gcgtgtattc cctgactagc gaaaaattca cgacgcctta ccgctatgtg       360
gattggctgt tgaccgtgcc tctgttgctg gtggagacag tggcagtgct gacgttgcct       420
gcaaaggagg caagacccct gctgatcaaa ctgacggtgg cttcagttct gatgattgcc       480
acgggctacc ccggcgagat ttctgacgac attacgactc gcatcatctg gggtacggtc       540
agcacgattc ccttcgccta catcctctat gtgttgtggg tcgaactgtc caggtccctt       600
gtccgccagc ccgctgctgt acaaaccctg gtccgcaaca tgcggtggct gctgttgctc       660
tcctggggtg tttacccgat cgcatacctt ctacccatgc ttggagtatc cggtacgtcc       720
gcggctgtcg cgttcaggt tggctatacg atcgcagacg tgctggcgaa gcctgtattt       780
ggtcttctag tcttcgcgat tgcactcgtg aaaacaaaag cagatcaaga aagcagtgaa       840
ccacatgccg caataggtgc tgctgcaaat aaatcgggag gcagtcttat ctcctag        897

<210> SEQ ID NO 14
<211> LENGTH: 298
<212> TYPE: PRT

-continued

<213> ORGANISM: Gloeobacter violaceus

<400> SEQUENCE: 14

```
Met Leu Met Thr Val Phe Ser Ser Ala Pro Glu Leu Ala Leu Leu Gly
1               5                   10                  15

Ser Thr Phe Ala Gln Val Asp Pro Ser Asn Leu Ser Val Ser Asp Ser
                20                  25                  30

Leu Thr Tyr Gly Gln Phe Asn Leu Val Tyr Asn Ala Phe Ser Phe Ala
            35                  40                  45

Ile Ala Ala Met Phe Ala Ser Ala Leu Phe Phe Phe Ser Ala Gln Ala
        50                  55                  60

Leu Val Gly Gln Arg Tyr Arg Leu Ala Leu Leu Val Ser Ala Ile Val
65                  70                  75                  80

Val Ser Ile Ala Gly Tyr His Tyr Phe Arg Ile Phe Asn Ser Trp Asp
                85                  90                  95

Ala Ala Tyr Val Leu Glu Asn Gly Val Tyr Ser Leu Thr Ser Glu Lys
            100                 105                 110

Phe Asn Asp Ala Tyr Arg Tyr Val Asp Trp Leu Leu Thr Val Pro Leu
        115                 120                 125

Leu Leu Val Glu Thr Val Ala Val Leu Thr Leu Pro Ala Lys Glu Ala
    130                 135                 140

Arg Pro Leu Leu Ile Lys Leu Thr Val Ala Ser Val Leu Met Ile Ala
145                 150                 155                 160

Thr Gly Tyr Pro Gly Glu Ile Ser Asp Asp Ile Thr Thr Arg Ile Ile
                165                 170                 175

Trp Gly Thr Val Ser Thr Ile Pro Phe Ala Tyr Ile Leu Tyr Val Leu
            180                 185                 190

Trp Val Glu Leu Ser Arg Ser Leu Val Arg Gln Pro Ala Ala Val Gln
            195                 200                 205

Thr Leu Val Arg Asn Met Arg Trp Leu Leu Leu Leu Ser Trp Gly Val
    210                 215                 220

Tyr Pro Ile Ala Tyr Leu Leu Pro Met Leu Gly Val Ser Gly Thr Ser
225                 230                 235                 240

Ala Ala Val Gly Val Gln Val Gly Tyr Thr Ile Ala Asp Val Leu Ala
                245                 250                 255

Lys Pro Val Phe Gly Leu Leu Val Phe Ala Ile Ala Leu Val Lys Thr
            260                 265                 270

Lys Ala Asp Gln Glu Ser Ser Glu Pro His Ala Ala Ile Gly Ala Ala
        275                 280                 285

Ala Asn Lys Ser Gly Gly Ser Leu Ile Ser
    290                 295
```

<210> SEQ ID NO 15
<211> LENGTH: 1317
<212> TYPE: DNA
<213> ORGANISM: Guillardia theta

<400> SEQUENCE: 15

```
atggcaagcc aagtcgttta tggagaatgg gcgagtacgc atacagaatg ttacaacatg      60
tcaaggatcg acagcacctt tgtctcattg ctgcagctgg tctgggctgt tgtcagcgga     120
tgccagacga tctttatgat ctctcgagcc ccgaaggtgc catgggaatc tgtttacctt     180
cccttcgttg aaagcatcac ctatgccctc gcttctactg aaacggcac gttgcagatg     240 agggacgggc gcttctttcc ttggtcgcgc atggcatcct ggttgtgcac ttgccctatc     300
```

-continued

```
atgctcgggc agatcagcaa catggcgctg gtgaagtaca agagcatccc gttgaatccc      360
atcgcgcaag cagcctccat catccgagtg gtgatgggaa tcacggcgac tatctctccc      420
gccgagtaca tgaagtggct cttttttcttc ttcggggcca cgtgcctggt ctttgagtac      480
tcagttgtct tcaccatctt tcaagtcggg ctgtacgggt ttgagagcgt ggggactccg      540
ctggctcaga aggtggtggt gagaatcaag atgctcagac tcatcttctt catcgcatgg      600
accatgttcc ccatcgtatg gctgatatcc cccactggcg tctgcgtcat tcatgagaac      660
gtgagcgcta tcctgtacct cctcgccgac gggctctgca agaacaccta cggagtgatc      720
ctgtggagca cggcatgggg cgtgttggaa gggaagtggg accctgcatg ccttccagga      780
caggagaagc cggaggccga cgatccgttt gggctgaacc atgagaagaa tgctcccccc      840
aacgatgaag tcaacatccg gatgttcgga cgcgtcatcg gctcggtgag gaagtcaaag      900
aggaggcaga agtgggagct ggcgccggcg catctagagg acaggatcag gttgagcgac      960
gaggagtcgg atgactcgag gccgaagagg aagaagaaag agacgcgcg ggactacagg     1020 aggaagcatc gaggaggcgc cgacgacgac gatcatcaca gcagcgaatc ggagagtgag     1080
aagaagaaca agggaaagaa gaagaagtcg ggcaagggaa agaagaagga cgactcgggc     1140
tccgaggacg atcttgaggt cggcaacggg aaggcgaaga acggagacaa gcaggagttc     1200
aacgacatca acaagatcct acgagccatg aagagaaacg ccgggacgct gagcgaaaag     1260
tctcattccg atgactccga gggaaagcgt gagagcgcgg atcattccat gtgctga      1317
```

```
<210> SEQ ID NO 16
<211> LENGTH: 438
<212> TYPE: PRT
<213> ORGANISM: Guillardia theta

<400> SEQUENCE: 16

Met Ala Ser Gln Val Val Tyr Gly Glu Trp Ala Ser Thr His Thr Glu
1               5                   10                  15

Cys Tyr Asn Met Ser Arg Ile Asp Ser Thr Phe Val Ser Leu Leu Gln
            20                  25                  30

Leu Val Trp Ala Val Val Ser Gly Cys Gln Thr Ile Phe Met Ile Ser
        35                  40                  45

Arg Ala Pro Lys Val Pro Trp Glu Ser Val Tyr Leu Pro Phe Val Glu
    50                  55                  60

Ser Ile Thr Tyr Ala Leu Ala Ser Thr Gly Asn Gly Thr Leu Gln Met
65                  70                  75                  80

Arg Asp Gly Arg Phe Phe Pro Trp Ser Arg Met Ala Ser Trp Leu Cys
                85                  90                  95

Thr Cys Pro Ile Met Leu Gly Gln Ile Ser Asn Met Ala Leu Val Lys
            100                 105                 110

Tyr Lys Ser Ile Pro Leu Asn Pro Ile Ala Gln Ala Ala Ser Ile Ile
        115                 120                 125

Arg Val Val Met Gly Ile Thr Ala Thr Ile Ser Pro Ala Glu Tyr Met
    130                 135                 140

Lys Trp Leu Phe Phe Phe Phe Gly Ala Thr Cys Leu Val Phe Glu Tyr
145                 150                 155                 160

Ser Val Val Phe Thr Ile Phe Gln Val Gly Leu Tyr Gly Phe Glu Ser
                165                 170                 175

Val Gly Thr Pro Leu Ala Gln Lys Val Val Val Arg Ile Lys Met Leu
            180                 185                 190

Arg Leu Ile Phe Phe Ile Ala Trp Thr Met Phe Pro Ile Val Trp Leu
```

-continued

```
                195                 200                 205

Ile Ser Pro Thr Gly Val Cys Val Ile His Glu Asn Val Ser Ala Ile
    210                 215                 220

Leu Tyr Leu Leu Ala Asp Gly Leu Cys Lys Asn Thr Tyr Gly Val Ile
225                 230                 235                 240

Leu Trp Ser Thr Ala Trp Gly Val Leu Glu Gly Lys Trp Asp Pro Ala
                245                 250                 255

Cys Leu Pro Gly Gln Glu Lys Pro Glu Ala Asp Asp Pro Phe Gly Leu
                260                 265                 270

Asn His Glu Lys Asn Ala Pro Pro Asn Asp Glu Val Asn Ile Arg Met
                275                 280                 285

Phe Gly Arg Val Ile Gly Ser Val Arg Lys Ser Lys Arg Arg Gln Lys
    290                 295                 300

Trp Glu Leu Ala Pro Ala His Leu Glu Asp Arg Ile Arg Leu Ser Asp
305                 310                 315                 320

Glu Glu Ser Asp Asp Ser Arg Pro Lys Arg Lys Lys Lys Gly Asp Ala
                325                 330                 335

Arg Asp Tyr Arg Arg Lys His Arg Gly Gly Ala Asp Asp Asp His
                340                 345                 350

His Ser Ser Glu Ser Glu Ser Glu Lys Lys Asn Lys Gly Lys Lys Lys
    355                 360                 365

Lys Ser Gly Lys Gly Lys Lys Lys Asp Asp Ser Gly Ser Glu Asp Asp
    370                 375                 380

Leu Glu Val Gly Asn Gly Lys Ala Lys Asn Gly Asp Lys Gln Glu Phe
385                 390                 395                 400

Asn Asp Ile Asn Lys Ile Leu Arg Ala Met Lys Arg Asn Ala Gly Thr
                405                 410                 415

Leu Ser Glu Lys Ser His Ser Asp Asp Ser Glu Gly Lys Arg Glu Ser
    420                 425                 430

Ala Asp His Ser Met Cys
        435
```

```
<210> SEQ ID NO 17
<211> LENGTH: 34
<212> TYPE: DNA
<213> ORGANISM: artificial sequence
<220> FEATURE:
<223> OTHER INFORMATION: Artificial Nucleic Acid

<400> SEQUENCE: 17
atcgagcgct acgtggtcgt gtgcaagccc atga                              34

<210> SEQ ID NO 18
<211> LENGTH: 33
<212> TYPE: DNA
<213> ORGANISM: artificial sequence
<220> FEATURE:
<223> OTHER INFORMATION: Artificial Nucleic Acid

<400> SEQUENCE: 18
atcgagcggt acgtagtggt gtgcaagccc atg                               33

<210> SEQ ID NO 19
<211> LENGTH: 11
<212> TYPE: PRT
<213> ORGANISM: artificial sequence
<220> FEATURE:
<223> OTHER INFORMATION: Artificial Peptide
```

-continued

```
<400> SEQUENCE: 19

Ile Glu Arg Tyr Val Val Val Cys Lys Pro Met
1               5                   10

<210> SEQ ID NO 20
<211> LENGTH: 51
<212> TYPE: DNA
<213> ORGANISM: artificial sequence
<220> FEATURE:
<223> OTHER INFORMATION: Artificial Nucleic Acid

<400> SEQUENCE: 20
ttcaccgtga aagaggccgc tgctcagcag caggaaagcg ccacaaccca g           51

<210> SEQ ID NO 21
<211> LENGTH: 51
<212> TYPE: DNA
<213> ORGANISM: artificial sequence
<220> FEATURE:
<223> OTHER INFORMATION: Artificial Nucleic Acid

<400> SEQUENCE: 21
ttcaccgtca aggaggctgc agcccagcag caggagtcgg ccaccactca g           51

<210> SEQ ID NO 22
<211> LENGTH: 16
<212> TYPE: PRT
<213> ORGANISM: artificial sequence
<220> FEATURE:
<223> OTHER INFORMATION: Artificial Peptide

<400> SEQUENCE: 22

Phe Thr Val Lys Glu Ala Ala Ala Gln Gln Gln Glu Ser Ala Thr Thr
1               5                   10                  15

<210> SEQ ID NO 23
<211> LENGTH: 1036
<212> TYPE: DNA
<213> ORGANISM: artificial sequence
<220> FEATURE:
<223> OTHER INFORMATION: Artificial Nucleic Acid

<400> SEQUENCE: 23
ggagacccaa gctggctagc gtttaaactt aagcttgcca ccatgttgat gaccgtattt    60
tcttctgcac ctgaacttgc ccttctcgga tcaacctttg cccaggtcga tccttcaaac   120
ttatcggtct cagattcgct gacctatggt cagttcaatc tggtttacaa cgctttctcg   180
tttgccatcg cggcaatgtt cgcatctgcc ctcttcttct tcagcgctca ggcactcgtc   240
ggtcaacgat accggttggc cttgcttgtt tcagcaattg ttgtgagtat cgctgggtac   300
cactactttc ggatcttcaa tagttgggat gctgcctacg ttctggagaa tggcgtgtat   360
tccctgacta gcgaaaaatt caacgacgcc taccgctatg tggattggct gttgaccgtg   420
cctctgttgc tggtgcaaac agtggcagtg atcgagcggt acgtagtggt gtgcaagccc   480
atgagcaact ccgcttcgg ggagaaccac cccttgctga tcaaactgac ggtggcttca   540
gttctgatga ttgccacggg ctaccccggc gagatttctg acgacattac gactcgcatc   600
atctggggta cggtcagcac gattcccttc gcctacatcc tctatgtgtt gtgggtcgaa   660
ctgtccttca ccgtcaagga ggctgcagcc cagcagcagg agtcggccac cactcaggta   720
caaaccctgg tccgcaacat gcggtggctg ctgttgctct cctggggtgt ttacccgatc   780
gcataccttc tacccatgct ggagtatccg gtacgtccg cggctgtcgg cgttcaggtt   840
```

```
ggctatacga tcgcagacgt gctggcgaag cctgtatttg gtcttctagt cttcgcgatt      900
gcactcgtga aaacaaaagc agatcaagaa agcagtgaac cacatgccgc aataggtgct      960
gctgcaaata aatcgggagg cagtcttatc tcctgatcta gagggcccgt ttaaacccgc     1020
tgatcagcct cgactg                                                     1036

<210> SEQ ID NO 24
<211> LENGTH: 60
<212> TYPE: DNA
<213> ORGANISM: artificial sequence
<220> FEATURE:
<223> OTHER INFORMATION: Artificial Nucleic Acid

<400> SEQUENCE: 24
atcgagcggt acgtagtggt gtgcaagccc atgagcaact ccgcttcgg ggagaaccac       60

<210> SEQ ID NO 25
<211> LENGTH: 20
<212> TYPE: PRT
<213> ORGANISM: artificial sequence
<220> FEATURE:
<223> OTHER INFORMATION: Artificial Peptide

<400> SEQUENCE: 25

Ile Glu Arg Tyr Val Val Val Cys Lys Pro Met Ser Asn Phe Arg Phe
1               5                   10                  15

Gly Glu Asn His
            20

<210> SEQ ID NO 26
<211> LENGTH: 5986
<212> TYPE: DNA
<213> ORGANISM: artificial sequence
<220> FEATURE:
<223> OTHER INFORMATION: chimera rhodopsin

<400> SEQUENCE: 26
agcgcccaat acgcaaaccg cctctccccg cgcgttggcc gattcattaa tgcagctggc       60
acgacaggtt tcccgactgg aaagcgggca gtgagcgcaa cgcaattaat gtgagttagc      120
tcactcatta ggcaccccag gctttacact ttatgcttcc ggctcgtatg ttgtgtggaa      180
ttgtgagcgg ataacaattt cacacaggaa acagctatga ccatgattac gaattgcctg      240
caggcagctg cgcgctcgct cgctcactga ggccgcccgg gcaaagcccg ggcgtcgggc      300
gacctttggt cgcccggcct cagtgagcga gcgagcgcgc agagagggag tggccaactc      360
catcactagg ggttcctatc gatatcaagc tttaatagta atcaattacg gggtcattag      420
ttcatagccc atatatggag ttccgcgtta cataacttac ggtaaatggc ccgcctggct      480
gaccgcccaa cgacccccgc ccattgacgt caataatgac gtatgttccc atagtaacgc      540
caatagggac tttccattga cgtcaatggg tggagtattt acggtaaact gcccacttgg      600
cagtacatca agtgtatcat atgccaagta cgccccctat tgacgtcaat gacggtaaat      660
ggcccgcctg gcattatgcc cagtacatga ccttatggga ctttcctact tggcagtaca      720
tctacgtatt agtcatcgct attaccatgg tgatgcggtt ttggcagtac atcaatgggc      780
gtggatagcg gtttgactca cggggatttc caagtctcca ccccattgac gtcaatggga      840
gtttgttttg gcaccaaaat caacgggact ttccaaaatg tcgtaacaac tccgccccat      900
tgacgcaaat gggcggtagg cgtgtacggt gggaggtcta tataagcaga gctggtttag      960
```

-continued

```
tggatatcct taagggccca gccggcccga atcccggccg ggaacggtgc attggaacgc      1020
ggattccccg tgccaagagt gacgtaagta ccgcctatag agtctatagg cccacaaaaa      1080
atgctttctt cttttaatat acttttttgt ttatcttatt tctaatactt tccctaatct      1140
ctttctttca gggcaataat gatacaatgt atcatgcctc tttgcaccat tctaaagaat      1200
aacagtgata atttctgggt taaggcaata gcaatatttc tgcatataaa tatttctgca      1260
tataaattgt aactgatgta agaggtttca tattgctaat agcagctaca atccagctac      1320
cattctgctt ttattttatg gttgggataa ggctggatta ttctgagtcc aagctaggcc      1380
cttttgctaa tcatgttcat acctcttatc ttcctcccac agctcctggg caacgtgctg      1440
gtctgtgtgc tggcccatca ctttggcaaa gaattgggat tcgcgagcca ccatgctgat      1500
gaccgtgttc agcagcgccc ctgagctggc cctgctgggc tctacatttg cccaggtgga      1560
ccccagcaac ctgagcgtgt ccgacagcct gacctacggc cagttcaacc tggtgtacaa      1620
cgccttcagc ttcgccattg ccgccatgtt cgccagcgcc ctgttcttct tcagtgcaca      1680
agccctcgtg ggccagcggt acagactggc tctgctggtg tctgccatcg tggtgtctat      1740
cgccggctac cactacttcc ggatcttcaa cagctgggac gccgcctacg tgctggaaaa      1800
cggcgtgtac tccctgacca gcgagaagtt caacgacgcc tacagatacg tggactggct      1860
gctgaccgtg cccctgctgc tggtgcaaac agtggccgtg atcgagcgct acgtggtcgt      1920
gtgcaagccc atgagcaact tcagattcgg cgagaaccac cccctgctga tcaagctgac      1980
agtggccagc gtgctgatga tcgccacagg ctaccctggc gagatcagcg acgacatcac      2040 caccccggatc atctggggaa ccgtgtccac catcccettc gcctacatcc tgtacgtgct      2100
gtgggtggaa ctgagcttca ccgtgaaaga ggccgctgct cagcagcagg aaagcgccac      2160
aacccaggtg cagaccctcg tgcggaacat gagatggttg ctgctgctgt cctgggggcgt      2220 gtaccctatc gcctacctgc tgcctatgct gggcgtgtcc ggaacatctg ccgctgtggg      2280
agtgcaagtg ggctacacaa tcgccgatgt gctggccaag cccgtgttcg gcctgctggt      2340
gttcgctatc gccctcgtga aaacaaaggc cgaccaggaa agcagcgagc cccacgccgc      2400
tattggagcc gccgctaaca agtctggcgg cagcctgatc agcttctgct acgagaatga      2460
agtgtaagga tccacgggtg gcatccctgt gacccctccc cagtgcctct cctggccctg      2520
gaagttgcca ctccagtgcc caccagcctt gtcctaataa aattaagttg catcattttg      2580
tctgactagg tgtccttcta taatattatg gggtggaggg gggtggtatg gagcaagggg      2640
caagttggga agacaacctg tagggcctgc ggggtctatt gggaaccaag ctggagtgca      2700
gtggcacaat cttggctcac tgcaatctcc gcctcctggg ttcaagcgat tctcctgcct      2760
cagcctcccg agttgttggg attccaggca tgcatgacca ggctcagcta attttttgttt      2820 ttttggtaga gacggggttt caccatattg gccaggctgg tctccaactc ctaatctcag      2880
gtgatctacc caccttggcc tcccaaattg ctgggattac aggcgtgaac cactgctccc      2940
ttccctgtcc ttatcgatag atctaggaac ccctagtgat ggagttggcc actccctctc      3000
tgcgcgctcg ctcgctcact gaggccgggc gaccaaaggt cgcccgacgc ccgggctttg      3060
cccgggcggc ctcagtgagc gagcgagcgc gcagctgcct gcaggcagct ggcactggcc      3120
cgtcgtttta caacgtcgtg actgggaaaa ccctggcgtt acccaactta atcgccttgc      3180
agcacatccc cctttcgcca gctggcgtaa tagcgaagag gcccgcaccg atcgcccttc      3240
ccaacagttg cgcagcctga atggcgaatg gcgcctgatg cggtattttc tccttacgca      3300
tctgtgcggt atttcacacc gcatacgtca aagcaaccat agtacgcgcc ctgtagcggc      3360
```

-continued

```
gcattaagcg cggcgggtgt ggtggttacg cgcagcgtga ccgctacact tgccagcgcc   3420
ctagcgcccg ctcctttcgc tttcttccct tcctttctcg ccacgttcgc cggctttccc   3480
cgtcaagctc taaatcgggg gctccctttta gggttccgat ttagtgcttt acggcacctc   3540
gaccccaaaa aacttgattt gggtgatggt tcacgtagtg ggccatcgcc ctgatagacg   3600 gttttttcgcc ctttgacgtt ggagtccacg ttctttaata gtggactctt gttccaaact   3660
ggaacaacac tcaaccctat ctcgggctat tcttttgatt tataagggat tttgccgatt   3720
tcggcctatt ggttaaaaaa tgagctgatt taacaaaaat ttaacgcgaa ttttaacaaa   3780
atattaacgt ttacaatttt atggtgcact ctcagtacaa tctgctctga tgccgcatag   3840
ttaagccagc cccgacaccc gccaacaccc gctgacgcgc cctgacgggc ttgtctgctc   3900
ccggcatccg cttacagaca agctgtgacc gtctccggga gctgcatgtg tcagaggttt   3960
tcaccgtcat caccgaaacg cgcgagacga aagggcctcg tgatacgcct attttttatag   4020 gttaatgtca tgataataat ggtttcttag acgtcaggtg gcactttttcg gggaaatgtg   4080 cgcggaaccc ctatttgttt attttttctaa atacattcaa atatgtatcc gctcatgaga   4140 caataacccct gataaatgct tcaataatat tgaaaaagga agagtatgag tattcaacat   4200
ttccgtgtcg cccttattcc cttttttgcg gcattttgcc ttcctgtttt tgctcaccca   4260
gaaacgctgg tgaaagtaaa agatgctgaa gatcagttgg gtgcacgagt gggttacatc   4320
gaactggatc tcaacagcgg taagatcctt gagagttttc gccccgaaga acgttttcca   4380
atgatgagca cttttaaagt tctgctatgt ggcgcggtat tatcccgtat tgacgccggg   4440
caagagcaac tcggtcgccg catacactat tctcagaatg acttggttga gtactcacca   4500
gtcacagaaa agcatcttac ggatggcatg acagtaagag aattatgcag tgctgccata   4560
accatgagtg ataacactgc ggccaactta cttctgacaa cgatcggagg accgaaggag   4620
ctaaccgctt ttttgcacaa catgggggat catgtaactc gccttgatcg ttgggaaccg   4680
gagctgaatg aagccatacc aaacgacgag cgtgacacca cgatgcctgt agcaatggca   4740
acaacgttgc gcaaactatt aactggcgaa ctacttactc tagcttcccg gcaacaatta   4800
atagactgga tggaggcgga taaagttgca ggaccacttc tgcgctcggc ccttccggct   4860 ggctggtttta ttgctgataa atctggagcc ggtgagcgtg ggtctcgcgg tatcattgca   4920
gcactggggc cagatggtaa gccctcccgt atcgtagtta tctacacgac ggggagtcag   4980
gcaactatgg atgaacgaaa tagacagatc gctgagatag gtgcctcact gattaagcat   5040
tggtaactgt cagaccaagt ttactcatat atactttaga ttgatttaaa acttcatttt   5100
taatttaaaa ggatctaggt gaagatcctt tttgataatc tcatgaccaa atcccttaa   5160 cgtgagtttt cgttccactg agcgtcagac cccgtagaaa agatcaaagg atcttcttga   5220
gatccttttt ttctgcgcgt aatctgctgc ttgcaaacaa aaaaaccacc gctaccagcg   5280
gtggtttgtt tgccggatca agagctacca actctttttc cgaaggtaac tggcttcagc   5340
agagcgcaga taccaaatac tgttcttcta gtgtagccgt agttaggcca ccacttcaag   5400
aactctgtag caccgcctac atacctcgct ctgctaatcc tgttaccagt ggctgctgcc   5460
agtggcgata agtcgtgtct taccgggttg gactcaagac gatagttacc ggataaggcg   5520
cagcggtcgg gctgaacggg gggttcgtgc acacagccca gcttggagcg aacgacctac   5580
accgaactga gatacctaca gcgtgagcta tgagaaagcg ccacgcttcc cgaagggaga   5640
aaggcggaca ggtatccggt aagcggcagg gtcggaacag gagagcgcac gagggagctt   5700
```

-continued

```
ccagggggaa acgcctggta tctttatagt cctgtcgggt ttcgccacct ctgacttgag    5760
cgtcgatttt tgtgatgctc gtcaggggggg cggagcctat ggaaaaacgc cagcaacgcg   5820 gccttttttac ggttcctggc cttttgctgg ccttttgctc acatgttctt tcctgcgtta   5880
tcccctgatt ctgtggataa ccgtattacc gcctttgagt gagctgatac cgctcgccgc    5940
agccgaacga ccgagcgcag cgagtcagtg agcgaggaag cggaag                   5986
```

```
<210> SEQ ID NO 27
<211> LENGTH: 324
<212> TYPE: PRT
<213> ORGANISM: artificial sequence
<220> FEATURE:
<223> OTHER INFORMATION: chimera rhodopsin

<400> SEQUENCE: 27

Met Leu Met Thr Val Phe Ser Ser Ala Pro Glu Leu Ala Leu Leu Gly
1               5                   10                  15

Ser Thr Phe Ala Gln Val Asp Pro Ser Asn Leu Ser Val Ser Asp Ser
            20                  25                  30

Leu Thr Tyr Gly Gln Phe Asn Leu Val Tyr Asn Ala Phe Ser Phe Ala
        35                  40                  45

Ile Ala Ala Met Phe Ala Ser Ala Leu Phe Phe Phe Ser Ala Gln Ala
    50                  55                  60

Leu Val Gly Gln Arg Tyr Arg Leu Ala Leu Leu Val Ser Ala Ile Val
65                  70                  75                  80

Val Ser Ile Ala Gly Tyr His Tyr Phe Arg Ile Phe Asn Ser Trp Asp
                85                  90                  95

Ala Ala Tyr Val Leu Glu Asn Gly Val Tyr Ser Leu Thr Ser Glu Lys
            100                 105                 110

Phe Asn Asp Ala Tyr Arg Tyr Val Asp Trp Leu Leu Thr Val Pro Leu
            115                 120                 125

Leu Leu Val Gln Thr Val Ala Val Ile Glu Arg Tyr Val Val Val Cys
    130                 135                 140

Lys Pro Met Ser Asn Phe Arg Phe Gly Glu Asn His Pro Leu Leu Ile
145                 150                 155                 160

Lys Leu Thr Val Ala Ser Val Leu Met Ile Ala Thr Gly Tyr Pro Gly
            165                 170                 175

Glu Ile Ser Asp Asp Ile Thr Thr Arg Ile Ile Trp Gly Thr Val Ser
            180                 185                 190

Thr Ile Pro Phe Ala Tyr Ile Leu Tyr Val Leu Trp Val Glu Leu Ser
        195                 200                 205

Phe Thr Val Lys Glu Ala Ala Ala Gln Gln Gln Glu Ser Ala Thr Thr
    210                 215                 220

Gln Val Gln Thr Leu Val Arg Asn Met Arg Trp Leu Leu Leu Leu Ser
225                 230                 235                 240

Trp Gly Val Tyr Pro Ile Ala Tyr Leu Leu Pro Met Leu Gly Val Ser
                245                 250                 255

Gly Thr Ser Ala Ala Val Gly Val Gln Val Gly Tyr Thr Ile Ala Asp
            260                 265                 270

Val Leu Ala Lys Pro Val Phe Gly Leu Leu Val Phe Ala Ile Ala Leu
    275                 280                 285
```

-continued

```
Val Lys Thr Lys Ala Asp Gln Glu Ser Ser Glu Pro His Ala Ala Ile
    290                 295                 300

Gly Ala Ala Ala Asn Lys Ser Gly Gly Ser Leu Ile Ser Phe Cys Tyr
305                 310                 315                 320

Glu Asn Glu Val
```

NUCLEIC ACID CONSTRUCT THAT ENCODES CHIMERIC RHODOPSIN

CROSS-REFERENCE TO RELATED APPLICATIONS

This application is a United States National Phase application, filed under 35 U.S.C. § 371, of International Application No. PCT/JP2020/034543, filed on Sep. 11, 2020, which claims priority to and benefits from Japanese Patent Application No. 2019-167553, filed on Sep. 13, 2019. The content of each of the foregoing applications is incorporated herein by reference in its entirety.

SEQUENCE LISTING

The Sequence Listing associated with this application is provided in text format in lieu of a paper copy and is hereby incorporated by reference into the specification. The name of the text file containing the Sequence Listing is 000373-0002-301_SL.txt. The text file is 51, 417 bytes in size, was created on Mar. 14, 2022, and is being submitted electronically via EFS-Web.

TECHNICAL FIELD

The present disclosure relates to prevention and suppression of progress of retinal diseases, improvement in visual cognitive behavioral functions, and enhancement of visual functions.

BACKGROUND ART

Rhodopsin is a photosensitive receptor with a seven transmembrane structure in the retina of humans and animals, and rhodopsin is also applied in medicine.

SUMMARY OF INVENTION

Solution to Problem

The inventors have found that a chimeric protein of two types of rhodopsins, an ion-transporting rhodopsin and a G protein-coupled receptor rhodopsin, has effects for the prevention and suppression of progress of retinal diseases, the improvement in visual cognitive behavioral functions, and the enhancement of visual functions. The inventors have found that the expression efficiency of a novel nucleic acid construct encoding chimeric rhodopsin, into which an endoplasmic reticulum transport signal has been introduced, is remarkably high and that it is effective for clinical application.

Accordingly, the present disclosure provides the following:
(Item X1)
A nucleic acid comprising: a nucleic acid sequence encoding a chimeric protein comprising at least part of an ion-transporting receptor rhodopsin and at least part of a G protein-coupled receptor rhodopsin; and a nucleic acid sequence encoding a signal sequence.
(Item X2)
The nucleic acid of Item X1, wherein the signal sequence is an endoplasmic reticulum export signal sequence.
(Item X3)
The nucleic acid of Item X1 or 2, wherein the nucleic acid comprises a nucleic acid sequence set forth in SEQ ID NO: 1 or 26.

(Item X4)
The nucleic acid of any one of Items X1-3, further comprising a nucleic acid sequence encoding a FLAG tag.
(Item X5)
The nucleic acid of any one of Items X1-4, wherein the nucleic acid comprises a nucleic acid sequence set forth in SEQ ID NO: 3.
(Item X6)
The nucleic acid of any one of Items X1-3, wherein the nucleic acid is a nucleic acid sequence set forth in SEQ ID NO: 26.
(Item X7)
A polypeptide consisting of: a chimeric protein of an ion-transporting receptor rhodopsin and a G protein-coupled receptor rhodopsin; and a signal sequence.
(Item X8)
The polypeptide of Item X7, wherein the signal sequence is an endoplasmic reticulum export signal sequence.
(Item X9)
The polypeptide of Item X8 or 9, wherein the polypeptide is an amino acid sequence set forth in SEQ ID NO: 2 or 27.
(Item X10)
The nucleic acid of Item X1, comprising a nucleic acid sequence encoding a polypeptide of any one of Items X7-9.
(Item X11)
The nucleic acid of Item X10, further comprising a nucleic acid sequence encoding a FLAG tag.
(Item X12)
The nucleic acid of Item X10 or 11, comprising a nucleic acid sequence encoding an amino acid sequence set forth in SEQ ID NO: 4.
(Item X13)
A nucleic acid comprising a nucleic acid sequence encoding a chimeric protein comprising at least part of an ion channeling receptor rhodopsin and at least part of a G protein-coupled receptor rhodopsin.
(Item X14)
The nucleic acid of Item X13, wherein the nucleic acid comprises a nucleic acid sequence set forth in SEQ ID NO: 7.
(Item X15)
A polypeptide comprising a chimeric protein comprising part of an ion channeling receptor rhodopsin and part of a G protein-coupled receptor rhodopsin.
(Item X16)
The polypeptide of Item X15, wherein the polypeptide is an amino acid sequence set forth in SEQ ID NO: 8.
(Item X17)
The nucleic acid of Item X13, comprising a nucleic acid sequence encoding a polypeptide of Item X15 or 16.
(Item X18)
The nucleic acid of Item X17, comprising a nucleic acid sequence encoding an amino acid sequence set forth in SEQ ID NO: 8.
(Item X19)
A nucleic acid construct comprising: a nucleic acid of any one of Items X1-6 and 10-12; and/or a nucleic acid of any one of Items X13-14 and 17-18; and a nucleic acid operably linked to the nucleic acid, for enabling expression in a cell.
(Item X20)
The nucleic acid construct of Item X19, further comprising a vector.
(Item X21)
The nucleic acid construct of Item X20, wherein the vector is a viral vector.

3

(Item X22)

The nucleic acid construct of Item X20 or 21, wherein the vector is a retro viral vector, a lentiviral vector, or an adeno-associated virus (AAV) vector.

(Item X23)

The nucleic acid construct of any one of Items X20-22, wherein the vector is an AAV vector.

(Item X24)

The nucleic acid construct of Item X23, wherein the AAV vector is AAV-DJ, AAV-2 or AAV-6.

(Item X25)

A composition for use in gene-introduction comprising: a nucleic acid of any one of Items X1-6 and 10-12; a nucleic acid of any one of Items X13-14 and 17-18; or a nucleic acid construct of any one of Items X19-24.

(Item X26)

A cell comprising one or more of: a nucleic acid of any one of Items X1-6 and 10-12; a polypeptide of any one of Items X7-9; a nucleic acid of any one of Items X13-14 and 17-18; a polypeptide of any one of Items X15-16; and a nucleic acid construct of any one of Items X19-24.

(Item X27)

The cell of Item X26, wherein the cell is a retinal cell.

(Item X28)

A pharmaceutical composition comprising one or more of: a nucleic acid of any one of Items X1-6 and 10-12; a polypeptide of any one of Items X7-9; a nucleic acid of any one of Items X13-14 and 17-18; a polypeptide of any one of Items X15-16; a nucleic acid construct of any one of Items X19-24; a gene-introducing composition of Item X25; and a cell of any one of Items X26-27.

(Item X29)

The pharmaceutical composition of Item X28 for use in treating, preventing or suppressing the progress of a disease, disorder or symptom of the retina.

(Item X30)

The pharmaceutical composition of Item X28 for use in improvement in a visual cognitive behavioral function.

(Item X31)

The pharmaceutical composition of Item X28 for use in enhancing a visual function.

(Item X32)

The pharmaceutical composition of Item X31 for use in enhancing an object recognition function.

(Item A1)

A method for treating, preventing or suppressing the progress of a disease, disorder or symptom of the retina in a subject, the method comprising: administering an effective amount of one or more of: a nucleic acid of any one of Items X1-6 and 10-12; a polypeptide of any one of Items X7-9; a nucleic acid of any one of Items X13-14 and 17-18; a polypeptide of any one of Items X15-16; a nucleic acid construct of any one of Items X19-24; a composition for use in gene-introduction of Item X25; and a cell of any one of Items X26-27 to the subject.

(Item A2)

A method for improving a visual cognitive behavioral function in a subject, the method comprising: administering an effective amount of one or more of: a nucleic acid of any one of Items X1-6 and 10-12; a polypeptide of any one of Items X7-9; a nucleic acid of any one of Items X13-14 and 17-18; a polypeptide of any one of Items X15-16; a nucleic acid construct of any one of Items X19-24; a composition use in gene-introduction of Item X25; and a cell of any one of Items X26-27 to the subject.

4

(Item A3)

A method for enhancing a visual function in a subject, the method comprising: administering an effective amount of one or more of: a nucleic acid of any one of Items X1-6 and 10-12; a polypeptide of any one of Items X7-9; a nucleic acid of any one of Items X13-14 and 17-18; a polypeptide of any one of Items X15-16; a nucleic acid construct of any one of Items X19-24; a composition use in gene-introduction of Item X25; and a cell of any one of Items X26-27 to the subject.

(Item A4)

A method for enhancing an object recognition function in a subject, the method comprising: administering an effective amount of one or more of: a nucleic acid of any one of Items X1-6 and 10-12; a polypeptide of any one of Items X7-9; a nucleic acid of any one of Items X13-14 and 17-18; a polypeptide of any one of Items X15-16; a nucleic acid construct of any one of Items X19-24; a composition use in gene-introduction of Item X25; and a cell of any one of Items X26-27 to the subject.

(Item B1)

Use of one or more of: a nucleic acid of any one of Items X1-6 and 10-12; a polypeptide of any one of Items X7-9; a nucleic acid of any one of Items X13-14 and 17-18; a polypeptide of any one of Items X15-16; a nucleic acid construct of any one of Items X19-24; a gene-introducing composition of Item X25; and a cell of any one of Items X26-27, in the manufacture of a pharmaceutical for use in treating, preventing or suppressing the progress of a disease, disorder or symptom of the retina.

(Item B2)

Use of one or more of: a nucleic acid of any one of Items X1-6 and 10-12; a polypeptide of any one of Items X7-9; a nucleic acid of any one of Items X13-14 and 17-18; a polypeptide of any one of Items X15-16; a nucleic acid construct of any one of Items X19-24; a composition use in gene-introduction of Item X25; and a cell of any one of Items X26-27, in the manufacture of a pharmaceutical for use in improving a visual cognitive behavioral function.

(Item B3)

Use of one or more of: a nucleic acid of any one of Items X1-6 and 10-12; a polypeptide of any one of Items X7-9; a nucleic acid of any one of Items X13-14 and 17-18; a polypeptide of any one of Items X15-16; a nucleic acid construct of any one of Items X19-24; a composition for use in gene-introduction of Item X25; and a cell of any one of Items X26-27, in the manufacture of a pharmaceutical for use in enhancing a visual function.

(Item B4)

Use of one or more of: a nucleic acid of any one of Items X1-6 and 10-12; a polypeptide of any one of Items X7-9; a nucleic acid of any one of Items X13-14 and 17-18; a polypeptide of any one of Items X15-16; a nucleic acid construct of any one of Items X19-24; a composition use in gene-introduction of Item X25; and a cell of any one of Items X26-27, in the manufacture of a pharmaceutical for use in enhancing an object recognition function.

(Item B5)

Use of: a nucleic acid of any one of Items X1-6 and 10-12; a nucleic acid of any one of Items X13-14 and 17-18; a gene of a nucleic acid construct of any one of Items X19-24; or a cell of any one of Items X26-27, in the manufacture of a pharmaceutical for use in introducing a gene.

(Item C1)

A nucleic acid of any one of Items X1-6 and 10-12; a polypeptide of any one of Items X7-9; a nucleic acid of any one of Items X13-14 and 17-18; a polypeptide of any one of Items X15-16; a nucleic acid construct of any one of Items X19-24; or a cell of any one of Items X26-27, for use in treating, preventing or suppressing the progress of a disease, disorder or symptom of the retina.
(Item C2)

A nucleic acid of any one of Items X1-6 and 10-12; a polypeptide of any one of Items X7-9; a nucleic acid of any one of Items X13-14 and 17-18; a polypeptide of any one of Items X15-16; a nucleic acid construct of any one of Items X19-24; or a cell of any one of Items X26-27, for use in improving a visual cognitive behavioral function.
(Item C3)

A nucleic acid of any one of Items X1-6 and 10-12; a polypeptide of any one of Items X7-9; a nucleic acid of any one of Items X13-14 and 17-18; a polypeptide of any one of Items X15-16; a nucleic acid construct of any one of Items X19-24; a gene-introducing composition of Item X25; or a cell of any one of Items X26-27, for use in enhancing a visual function.
(Item C4)

A nucleic acid of any one of Items X1-6 and 10-12; a polypeptide of any one of Items X7-9; a nucleic acid of any one of Items X13-14 and 17-18; a polypeptide of any one of Items X15-16; a nucleic acid construct of any one of Items X19-24; or a cell of any one of Items X26-27, for use in enhancing an object recognition function.
(Item C5)

A nucleic acid of any one of Items X1-6 and 10-12; a nucleic acid of any one of Items X13-14 and 17-18; or a nucleic acid construct of any one of Items X19-24, for use in introducing a gene.
(Item 1)

A nucleic acid comprising: a nucleic acid sequence encoding a chimeric protein comprising at least part of an ion-transporting receptor rhodopsin and at least part of a G protein-coupled receptor rhodopsin; and a nucleic acid sequence encoding a signal sequence.
(Item 2)

The nucleic acid of Item 1, wherein the signal sequence is an endoplasmic reticulum export signal sequence.
(Item 3)

The nucleic acid of Item 1 or 2, wherein the nucleic acid comprises a nucleic acid sequence set forth in SEQ ID NO: 1.
(Item 4)

The nucleic acid of any one of Items 1-3, further comprising a nucleic acid sequence encoding a FLAG tag.
(Item 5)

The nucleic acid of any one of Items 1-4, wherein the nucleic acid comprises a nucleic acid sequence set forth in SEQ ID NO: 3.
(Item 6)

A polypeptide consisting of: a chimeric protein of an ion-transporting receptor rhodopsin and a G protein-coupled receptor rhodopsin; and a signal sequence.
(Item 7)

The polypeptide of Item 6, wherein the signal sequence is an endoplasmic reticulum export signal sequence.
(Item 8)

The polypeptide of Item 7 or 8, wherein the polypeptide is an amino acid sequence set forth in SEQ ID NO: 2.
(Item 9)

The nucleic acid of Item 1, comprising a nucleic acid sequence encoding a polypeptide of any one of Items 6-8.
(Item 10)

The nucleic acid of Item 9, further comprising a nucleic acid sequence encoding a FLAG tag.

(Item 11)

The nucleic acid of Item 9 or 10, comprising a nucleic acid sequence encoding an amino acid sequence set forth in SEQ ID NO: 4.
(Item 12)

A nucleic acid comprising a nucleic acid sequence encoding a chimeric protein comprising at least part of an ion channeling receptor rhodopsin and at least part of a G protein-coupled receptor rhodopsin.
(Item 13)

The nucleic acid of Item 12, wherein the nucleic acid comprises a nucleic acid sequence set forth in SEQ ID NO: 7.
(Item 14)

A polypeptide comprising a chimeric protein comprising part of an ion channeling receptor rhodopsin and part of a G protein-coupled receptor rhodopsin.
(Item 15)

The polypeptide of Item 14, wherein the polypeptide is an amino acid sequence set forth in SEQ ID NO: 8.
(Item 16)

The nucleic acid of Item 12, comprising a nucleic acid sequence encoding a polypeptide of Item 14 or 15.
(Item 17)

The nucleic acid of Item 16, comprising a nucleic acid sequence encoding an amino acid sequence set forth in SEQ ID NO: 8.
(Item 18)

A nucleic acid construct comprising: a nucleic acid of any one of Items 1-5 and 9-11; and/or a nucleic acid of any one of Items 12-13 and 16-17; and a nucleic acid operably linked to the nucleic acid, for use in enabling expression in a cell.
(Item 19)

The nucleic acid construct of Item 18, further comprising a vector.
(Item 20)

The nucleic acid construct of Item 19, wherein the vector is a viral vector.
(Item 21)

The nucleic acid construct of Item 19 or 20, wherein the vector is a retroviral vector, a lentiviral vector, or an adeno-associated virus (AAV) vector.
(Item 22)

The nucleic acid construct of any one of Items 19-21, wherein the vector is an AAV vector.
(Item 23)

The nucleic acid construct of Item 22, wherein the AAV vector is AAV-DJ, AAV-2 or AAV-6.
(Item 24)

A composition use in gene-introduction comprising: a nucleic acid of any one of Items 1-5 and 9-11; a nucleic acid of any one of Items 12-13 and 16-17; or a nucleic acid construct of any one of Items 18-23.
(Item 25)

A cell comprising one or more of: a nucleic acid of any one of Items 1-5 and 9-11; a polypeptide of any one of Items 6-8; a nucleic acid of any one of Items 12-13 and 16-17; a polypeptide of any one of Items 14-15; and a nucleic acid construct of any one of Items 18-23.
(Item 26)

The cell of Item 25, wherein the cell is a retinal cell.
(Item 27)

A pharmaceutical composition comprising one or more of: a nucleic acid of any one of Items 1-5 and 9-11; a polypeptide of any one of Items 6-8; a nucleic acid of any one of Items 12-13 and 16-17; a polypeptide of any one of Items 14-15; a nucleic acid construct of any one of Items 18-23; a gene-introducing composition of Item 24; and a cell of any one of Items 25-26.

(Item 28)

The pharmaceutical composition of Item 27 for use in treating, preventing or suppressing the progress of a disease, disorder or symptom of the retina.

(Item 29)

The pharmaceutical composition of Item 27 for use in improving a visual cognitive behavioral function.

(Item 30)

The pharmaceutical composition of Item 27 for use in enhancing a visual function.

(Item 31)

The pharmaceutical composition of Item 30 for use in enhancing an object recognition function.

In the present disclosure, it is intended that the above one or more features may be provided in further combinations, in addition to the explicit combinations. Still further embodiments and advantages of the present disclosure will be appreciated by those skilled in the art upon reading and understanding the following detailed description as necessary.

Advantageous Effects of Invention

The present disclosure has demonstrated that the gene expression of the chimeric protein is higher in both efficiency and sensitivity and functions more efficiently. According to the present disclosure, a better visual restoration effect can be obtained. The present disclosure has not only confirmed an increase in expression level and sensitiveness to light exceeding the expression level and sensitiveness to light of the conventional construct in MEA, but also confirmed significant restoration of optical response in the central nervous system in VEP. When this is applied to the visual restoration gene therapy for human retinal diseases, it is expected to have the effect of visual sense restoration in darker places and the effect of expanding the visual field. This further achieves effects on restoring and improving light-dark determination functions and visual cognitive behavioral functions, effects on restoring object recognition functions, preventive and progress-suppressing effects on diseases, and the like.

BRIEF DESCRIPTION OF DRAWINGS

FIGS. 2A to 2C are diagrams showing results of multi-electrode array test in mice injected with the first nucleic acid construct.

FIGS. 3A to 3C are diagrams showing results of multi-electrode array test in mice injected with the nucleic acid construct of the present disclosure.

FIG. 13 shows the experimental data of forcible expression of each gene in HEK293T cells using the lipofection method and the measurement of the change in CAMP concentration with and without light stimulation.

DESCRIPTION OF EMBODIMENTS

Figure 1:
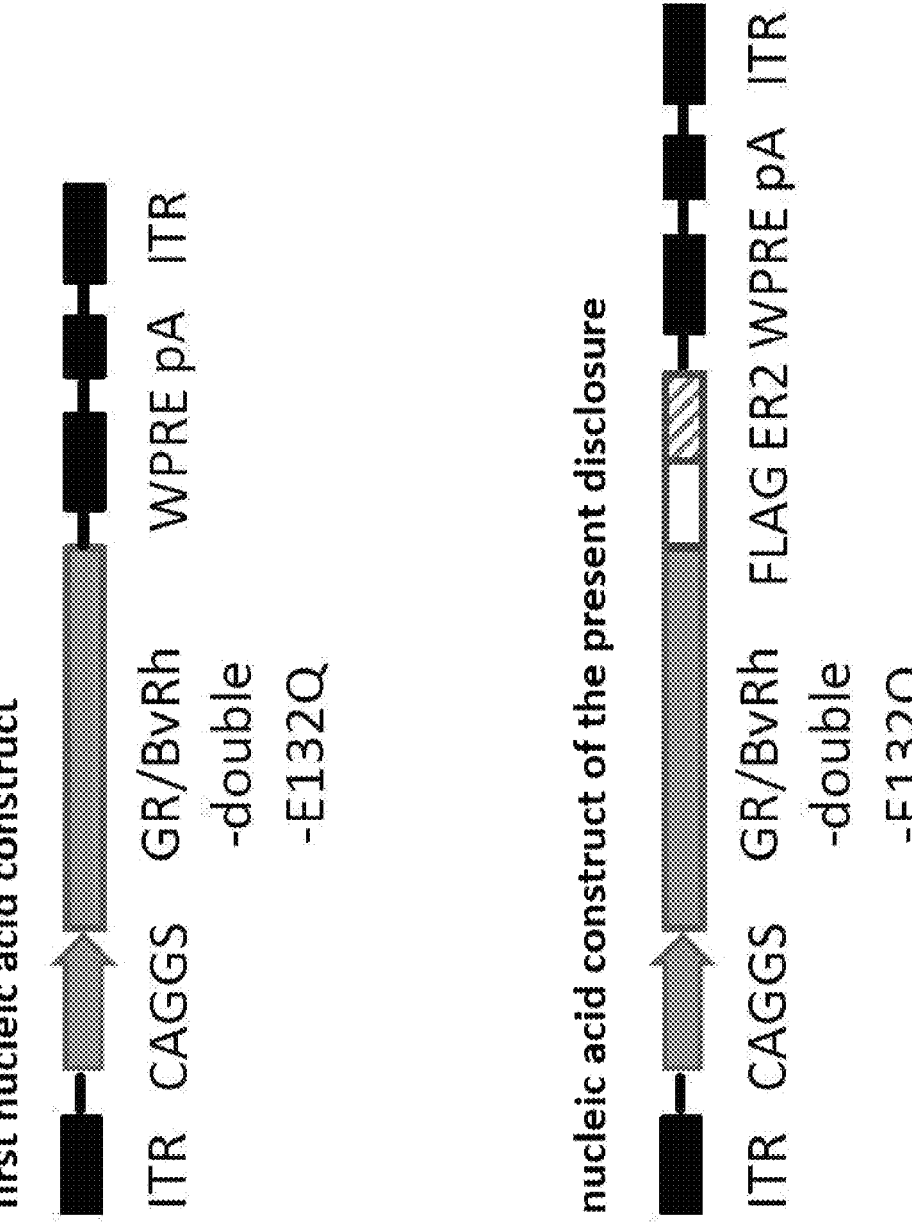
FIG. 1 is a diagram showing a configuration of a nucleic acid construct encoding a chimeric rhodopsin (the first nucleic acid construct) and a nucleic acid construct encoding a chimeric rhodopsin to which a signal sequence has been added (the nucleic acid construct of the present disclosure).

Hereinafter, the present disclosure will be described while showing the best mode. Throughout the present specification, it should be understood that the representation of a singular form also includes the concept of a plural form thereof, unless otherwise stated. It should thus be understood that singular articles (e.g., "a", "an", "the", etc. in the English language) also include the concept of a plural form thereof, unless otherwise stated. It should also be understood that the terms used herein are used in the meaning commonly used in the art, unless otherwise stated. Thus, unless otherwise defined, all technical terms and scientific terms used herein have the same meaning as commonly understood by those skilled in the art to which the present disclosure pertains. In case conflict, of the present specification (including definitions) takes precedence.

(Definitions etc.)

The definitions and/or basic technical contents of terms particularly used in the present specification will be described below as appropriate.

As used herein, a "rhodopsin" is a protein having a chromophore called retinal inside, which is activated by receiving light, thereby transmitting a visual signal to the brain. Ion-transporting receptor rhodopsins, typified by those of microbial origin, can be repeatedly activated by absorbing light because they do not release retinal by light irradiation; however, they are unable to activate a G protein like the G protein-coupled receptor rhodopsins as typified by those of animal origin. In contrast, the chimeric rhodopsin with an ion-transporting receptor rhodopsin and a G protein-coupled receptor rhodopsin, as provided in the present disclosure, is thought to have enhanced functions compared to the conventional rhodopsin. In particular, the ion-transporting receptor rhodopsin can preferably be of microbial origin, and those that can be repeatedly used are utilized. Furthermore, when the G protein-coupled receptor rhodopsin of animal origin, preferably of mammalian origin, is utilized, high activity via an endogenous G protein can be obtained while the function of repeated activation is retained. Without wishing to be bound by theory, the chimeric protein utilized in the present disclosure is expressed in mammals, such as rodents and primates, while retaining sufficient activity, as demonstrated by the animal models; thus, the chimeric protein is capable of achieving preventive and progress-suppressing effects diseases, for disorders or symptoms of the retina, and in particular, the prevention or suppression of progress of retinitis pigmentosa, or providing improvement in visual cognitive behavioral functions (e.g., improvement in light-dark determination functions, improvement in bright spot evading functions, and/or crisis avoidance functions), or exerting effects for augmenting visual functions, such as improvement in visual acuity.

As used herein, an "ion-transporting receptor rhodopsin" refers to any rhodopsin having a function of transporting ions, and examples thereof include an ion pumping receptor rhodopsin and an ion channeling receptor rhodopsin.

With regard to the ion-transporting receptor rhodopsin, the conformational compatibility and the membrane transfer efficiency with the G protein activation loop are considered to be important. In particular, the ion-transporting receptor rhodopsins of algal or microbial origin have good conformational compatibility and membrane transfer efficiency with the G protein activation loop, and among them, those pertaining to the genus Gloeobacter or genus Guillardia are preferable. In particular, Gloeobacter *violaceus*, among the microorganisms pertaining to the genus Gloeobacter, and Guillardia theta of the genus Guillardia are preferable. It is also preferable to combine and utilize the rhodopsin (e.g., SEQ ID NO: 14) of microorganisms pertaining to the genus Gloeobacter, or the rhodopsin (e.g., SEQ ID NO: 16) of microorganisms pertaining to the genus Guillardia, with a G protein-coupled receptor rhodopsin of mammalian origin, and preferably a G protein-coupled receptor rhodopsin of Artiodactyla, such as cow (e.g., SEQ ID NO: 12), or primates such as humans (e.g., SEQ ID NO: 10), among the G protein-coupled receptor rhodopsins of animal origin. The genus Gloeobacter, as well as the algae of the genus Guillardia etc., are also preferable in terms of having an important property of being expressed well in *E. coli*, which are eubacteria, and human cells, which are eukaryotes.

As used herein, an "ion pumping receptor rhodopsin" refers to any pumping rhodopsin having a function of transporting ions. When such a rhodopsin is sensitive to light, it functions by actively transporting ions, such as hydrogen ions, chloride ions or sodium ions, into cells.

As used herein, an "ion channeling receptor rhodopsin" refers to any channeling rhodopsin having a function of transporting ions. When such a rhodopsin is sensitive to light, it functions by allowing ions, such as hydrogen ions, chloride ions or sodium ions, to flow into cells.

As used herein, a "G protein-coupled receptor rhodopsin" refers to a rhodopsin classified as a G protein-coupled receptor, which is a type of receptor existing on the cytoplasmic membrane of eukaryotic cells or on the constituent membrane inside the cell. The G protein-coupled receptor is said to have seven α-helix structures that penetrate the cytoplasmic membrane, with the N-terminal side being extracellular and the C-terminal side being intracellular, and three extracellular loops (ECL1/2/3) and three intracellular loops (ICL1/2/3). The rhodopsin is composed of apoprotein and chromophore retinal, and retinal absorbs light to isomerize and cause structural changes in the protein part, driving the intracellular signal transduction system via the G protein.

As used herein, a "disease, disorder or symptom of the retina" refers to any disease, disorder or symptom related to the retina, and the examples include retinal degenerative diseases (retinitis pigmentosa, age-related macular degeneration, etc.), retinopathy (e.g., diabetic retinopathy, proliferative retinopathy, simple tear, retinal detachment retinopathy, etc.), floater, retinal (e.g., rhegmatogenous retinal detachment, non-rhegmatogenous retinal detachment, etc.), and the like. Herein, the present disclosure is capable of preventing, treating or suppressing the progress of retinal degenerative diseases, age-related macular degeneration, myopic maculopathy, macular dystrophy, diabetic retinopathy, retinal detachment, and the like. Examples of the disorder or symptom include disorders in visual acuity, contrast sensitivity, light-dark adaptation, color vision, etc., and symptoms associated therewith.

As used herein, a "visual cognitive behavioral function" refers to functioning of the visual information recognized by the visual organs (eyes, etc.) as the behavior of the target organism, where the visual cognitive behavioral function appears as actual behaviors, such as light-dark determination functions, bright spot evading functions and crisis avoidance functions. The visual cognitive behavioral function is such a function that can be confirmed, not only by confirming photosensitivity, but also by actually verifying it with an animal model.

As used herein, a "light-dark determination function" refers to an ability or function that can judge light and dark. The improvement therein may be any improvement in the light-dark determination function, the improvement of which also encompasses, for example, improvement in being able to determine what could not be determined as light or dark, and improvement in matters in which the difference between light and dark can be barely recognized.

As used herein, a "bright spot evading function" refers to the ability or function to move away from a light source or avoid bright light. The improvement therein refers to restoration or enhancement of the ability to avoid a bright spot.

As used herein, a "crisis avoidance function" refers to a function or ability to avoid a crisis based on a visual function. The improvement therein encompasses restoring crisis avoidance ability, and additionally, raising the levels thereof.

As used herein, the "enhancement" or "augmentation" of the "visual function" refers to improvement, enhancement or augmentation of any visual functions (e.g., visual acuity, color vision, contrast sensitivity, light-dark adaptation, etc.).

As used herein, an "improvement in visual acuity" refers to improving or recovering the visual acuity. In the case of humans, for example, the visual acuity can be measured by a Snellen chart or an E chart in addition to a visual acuity test using a Randold ring, and can be expressed by decimal visual acuity or fractional visual acuity. These can also be displayed with logMAR visual acuity. In the case of mice, the visual acuity can be measured using visual stimuli that manipulate the spatial frequencies of light and dark stripes. The visual acuity can also be determined experimentally by measuring the visual evoked potential.

As used herein, an "object recognition function" refers to a function or ability to visually recognize an object. The "object recognition function" requires a certain level of "visual acuity" in addition to the "light-dark determination function". The improvement therein may be any improvement in the object recognition function, encompassing, for example, improvement in being able to function to recognize what could not be recognized as an object, and improvement in the level at which one can barely recognize an object.

As used herein, a "retinal degenerative disease" refers to any disease caused by degeneration of the retina, and examples thereof include, for example, retinitis pigmentosa, age-related macular degeneration, and the like.

As used herein, "retinitis pigmentosa" is a hereditary disease with abnormalities in the retina, in which the photoreceptor and pigment epithelial cells of the retina are extensively degenerated. In the retinitis pigmentosa, three symptoms appear: night blindness (difficulty seeing things in the dark), narrowing of the visual field (narrow vision), and decreased visual acuity. The degeneration of only rod cells among the photoreceptor cells is called rod dystrophy, while the degeneration of both rod cells and cone cells, among the photoreceptor cells, is called rod cone dystrophy. Studies are being promoted on gene therapy, artificial retina, retinal restoration, photoreceptor protection therapy, etc., but no cure has been established for these diseases. Since these diseases are binocularly progressive and often lead to social blindness in childhood at the earliest, it is very significant to suppress their progress.

As used herein, the "retinitis pigmentosa" includes autosomal recessive inherited retinitis pigmentosa as well as autosomal dominant inherited retinitis pigmentosa and X-chromosome recessive inherited retinitis pigmentosa. The most common retinitis pigmentosa is the type showing autosomal recessive inheritance, which accounts for about 35% of the total. The next most common is the type showing autosomal dominant inheritance, which accounts for 10% of the total. The least common is the type showing X-linked inheritance (X-chromosome recessive inheritance), which accounts for about 5% of the total.

As used herein, "suppression of progress" refers to the suppression of progress of a disease (e.g., retinitis pigmentosa), where the suppression encompasses a reduction in the rate of exacerbations compared to the absence of treatment, as well as maintenance and improvement in the disease levels. If a certain disease has not developed, it falls under "prevention of onset". As used herein, the "onset" refers to appearance of a subjective symptom of disease from a state in which no such subjective symptom of the disease appears. Examples of the subjective symptoms include symptoms such as night blindness, narrowing of vision, photophobia, decreased visual acuity and defective color vision.

As used herein, "immediately after" the "onset" refers to within a certain period of time from the time when a subjective symptom appear in the patient, and examples thereof include, but not limited to, within 1 year, within 6 months, and within 3 months, for example.

As used herein, the terms, "protein," "polypeptide," "oligopeptide," and "peptide", are used interchangeably with the same meaning, and they refer to polymers of amino acids of any length. The polymer may be linear, branched or cyclic. The amino acids may be natural or non-natural, or may be modified amino acids. The term may also encompass those assembled into a complex of multiple polypeptide chains. The term also encompasses naturally or artificially modified amino acid polymers. Such modifications encompass, for example, disulfide bond formation, glycosylation, lipidation, acetylation, phosphorylation or any other manipulation or modification (e.g., conjugation with a labeling component). The subject definition also encompasses, for example, polypeptides including one or more analogs of amino acids (including, for example, unnatural amino acids), peptide-like compounds (e.g., peptoids) and other modifications known in the art. As used herein, an "amino acid" is a general term for organic compounds having an amino group and a carboxyl group. When the antibody according to the embodiment of the present disclosure includes a "specific amino acid sequence", any amino acid in the amino acid sequence may be a chemically-modified amino acid. Furthermore, any amino acid in the amino acid sequence may form a salt or a solvate. Furthermore, any amino acid in the amino acid sequence may be of L-type or D-type. Even in such cases, the protein according to the embodiment of the present disclosure is considered to include the above-mentioned "specific amino acid sequence". As for chemical modifications that amino acids included in proteins undergo in vivo, known are, for example, N-terminal modification (e.g., acetylation, myristoylation, etc.), C-terminal modification (e.g., amidation, glycosylphosphatidylinositol addition, etc.), side chain modifications (e.g., phosphorylation, glycosylation, etc.), or the like. It may be natural or non-natural as long as it satisfies the object of the present disclosure.

As used herein, a "chimera" (protein, rhodopsin) refers to a substance in a state in which genetic information derived from different organisms is mixed with each other in the same entity (in this case, protein, rhodopsin, etc.). The chimeric protein includes gene sequences derived from, for example, two or three or more organisms mixed therein. The sequence information contained in the chimeric protein may include a sequence other than the sequence derived from the organism to be mixed.

As used herein, the terms, "polynucleotide", "oligonucleotide" and "nucleic acid", are used interchangeably with the same meaning, and they refer to polymers of nucleotides of any length. The terms also include an "oligonucleotide derivative" or "polynucleotide derivative". The "oligonucleotide derivative" or "polynucleotide derivative" refers to an oligonucleotide or polynucleotide containing a derivative of a nucleotide or having an unusual bond between nucleotides, and the terms are used interchangeably. Specific examples of such oligonucleotides include, for example, 2'-O-methyl-ribonucleotide, an oligonucleotide derivative in which a phosphate diester bond in an oligonucleotide is converted to a phosphorothioate bond, an oligonucleotide derivative in which a phosphate diester bond in an oligonucleotide is converted into an N3'-P5'phospholoamidate bond, an oligonucleotide derivative in which ribose and a phosphodiester bond in an oligonucleotide are converted into a peptide nucleic acid bond, an oligonucleotide derivative in which uracil in an oligonucleotide is substituted by C-5 propynyl uracil, an oligonucleotide derivative in which uracil in an oligonucleotide is substituted by C-5 thiazole uracil, an oligonucleotide derivative in which cytosine in an oligonucleotide is substituted by C-5 propynylcytosine, an oligonucleotide derivative in which cytosine in an oligonucleotide is substituted by phenoxazine-modified cytosine, an oligonucleotide derivative in which ribose in DNA is substituted by 2'-O-propyl ribose, and an oligonucleotide derivative in which ribose in an oligonucleotide is substituted by 2'-methoxyethoxyribose, and the like. Unless otherwise indicated, particular base sequences are also intended to include conservatively modified variants (e.g., degenerate codon substitutes) and complementary sequences thereof, similarly to the explicitly indicated sequences. Note that the sequences of nucleic acids are also referred to as nucleic acid sequences, nucleotide sequences, etc., in addition to base sequences, but they all have the same meaning. Specifically, the degenerate codon substitute may be achieved by creating a sequence in which the third position of one or more selected (or all) codons is substituted by a mixed base and/or deoxyinosine residue (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). In accordance with the context, the "nucleic acid" is also used herein interchangeably with genes, DNA such as cDNA, RNA such as mRNA, oligonucleotides, and poly-nucleotides. The "nucleotide" herein may be natural or non-natural. The nucleic acids can be DNA or RNA herein.

As used herein, a "gene" refers to a factor that defines a trait, and the "gene" may refer to any genetic of a "poly-nucleotide", an "oligonucleotide" and a "nucleic acid".

As used herein, the terms, "nucleic acid construct", "construct" and "gene construct", are used interchangeably, and they are nucleic acid molecules containing a vector and nucleic acids isolated from naturally occurring genes or combined and juxtaposed in a non-naturally occurring man-ner.

As used herein, "homology" of a gene refers to the degree of identity of two or more gene sequences to each other, and the concept of having "homology" generally refers to having a high degree of identity or similarity. The term, "identity", refers to the equivalent degree of sequence of the same amino acid, while the term, "similarity", refers to the equiva-lent degree of sequence, including amino acids of similar nature, in addition to the same amino acid. Thus, as the degree of the homology of two certain genes increases, the degree of the identity or similarity of their sequences increases. Whether or not two different genes have homol-ogy can be examined by direct sequence comparison or, in the case of nucleic acids, hybridization under stringent conditions. In a direct comparison between two gene sequences, those genes are homologous when the DNA sequences are typically at least 50% identical, preferably at least 70% identical, and more preferably at least 80%, 90%, 95%, 96%, 97%, 98% or 99% identical, between the gene sequences thereof. Thus, as used herein, a "homologue" or "homologous gene product" means a protein in another species, preferably a mammal, that exerts the same biologi-cal functions as the protein components of the complex further described herein. Such homologues are also some-times referred to as "ortholog gene products". It is under-stood that such homologues, homologous gene products, ortholog gene products and the like can also be used as long as these substances meet the object of the present disclosure.

Amino acids can be referred to herein by either their generally known three-letter symbols or the one-letter sym-bols recommended by the IUPAC-IUB Biochemical Nomenclature Commission. Nucleotides can also be referred to by the generally recognized one-letter codes. Herein, comparison of similarity, identity and homology of amino acid sequences and base sequences is calculated with default parameters using a tool for sequence analysis, BLAST. The identity search can be performed using, for example, NCBI's BLAST 2.2.28 (issued on 4 Feb. 2013) (Proc. Natl. Acad. Sci. USA 90:5873-5877, 1993). The value of identity herein usually refers to the value obtained by performing alignment under the default conditions using the above BLAST. However, if a higher value is obtained by varying the parameters, the highest value obtained is set as the value for the identity. When identity is evaluated in multiple regions, the highest value among them is set as the value for the identity. Similarity refers to a numerical value that takes into account similar amino acids in addition to identity. Blastp can be used with default settings for the algorithm in the comparison between amino acid sequences in BLAST. The measurement results are quantified as Posi-tives or Identities. The homology of the amino acid sequence and base sequence can be determined by the algorithm BLAST by Karlin and Altschul. Based on this algorithm, programs called BLASTN and BLASTX have been devel-oped (Altschul et al. J. Mol. Biol. 215:403-410, 1990). When the base sequence is analyzed by BLASTN based on BLAST, the parameters are set as, for example, score=100 and world length=12. When the amino acid sequence is analyzed by BLASTX based on BLAST, the parameters are set as, for example, score=50 and worldlength=3. When BLAST and Gapped BLAST programs are used, the default parameters of each program are used. Specific techniques of these analysis methods are known.

The nucleic acid or protein as used herein may include a sequence in which one or more amino acids or nucleotides are substituted, deleted and/or added in the amino acid or base sequence of interest. In this regard, the term "one or more", in the chimeric protein full-length amino acid sequence, typically means 50 amino acids or less, preferably 30 amino acids or less, and still more preferably 10 amino acids or less (e.g., 5 amino acids or less, 3 amino acids or less, or one amino acid). Further, "one or more", in an amino acid sequence of a domain, typically means 6 amino acids or less, preferably 5 amino acids or less, and still more pref-erably 4 amino acids or less (e.g., 3 amino acids or less, 2 amino acids or less, and one amino acid). When maintaining the claimed biological activity of chimeric protein, it is desirable that an amino acid residue to be mutated be mutated to another amino acid which conserves the property of the amino acid side chain. Examples of properties of an amino acid side chain include hydrophobic amino acids (A, I, L, M, F, P, W, Y, V), hydrophilic amino acids (R, D, N, C, E, Q, G, H, K, S, T), amino acids with an aliphatic side chain (G, A, V, L, I, P), amino acids with a hydroxyl group containing side chain (S, T, Y), amino acids with a sulfur atom containing side chain (C, M), amino acids with a carboxylic acid and amide containing side chain (D, N, E, Q), amino acids with a base containing side chain (R, K, H), and amino acids with an aromatic containing side chain (H, F, Y, W) (each symbol within the parenthesis represents the one-letter code of an amino acid). These are also referred to herein as "conservative substitutions". Note that a protein having an amino acid sequence modified by deletion, addi-tion and/or substitution with another amino acid of one or more amino acid residues to the amino acid sequence, is known to maintain the biological activity thereof (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dal-badie-McFarland, G. et al., Proc. Natl. Acad. Sci. USA (1982) 79, 6409-6413). Therefore, in one embodiment of the present disclosure, "several" may be, for example, 10, 8, 6, 5, 4, 3, or 2, or may be less than or equal to any one of these numerical values. Chimeric protein with deletion etc. can be produced, for example, by a site-specific mutagenesis method, a random mutagenesis method, biopanning using an antibody phage library, or the like. As a site-specific muta-genesis method, KOD-Plus-Mutagenesis Kit (TOYOBO CO., LTD.), for example, can be used. It is possible to select an antibody having the same activity as the wild type, from the mutant-type antibody into which the deletion or the like has been introduced, by performing various characteriza-tions, such as FACS analysis and ELISA.

As used herein, a "signal sequence" refers to an amino acid sequence that, when functionally linked to a protein or peptide, promotes transport of the linked protein or peptide to a functional position. If the protein to which the signal sequence is linked is a membrane protein, an endoplasmic reticulum import signal peptide or an endoplasmic reticulum export signal peptide may be linked.

As used herein, an "endoplasmic reticulum import signal peptide" refers to amino acids mainly composed of hydrophobic amino acids of about 5 to 10 amino acids added to the amino terminus of the protein promoted for the transfer to the endoplasmic reticulum. If a particular amino acid sequence in a protein known to transfer to the endoplasmic reticulum is deleted or mutated and the transfer to the endoplasmic reticulum is significantly reduced, then that particular amino acid sequence can be determined as the endoplasmic reticulum import signal peptide.

As used herein, an "endoplasmic reticulum export signal peptide" refers to amino acids that promote the transport of a protein from the endoplasmic reticulum to other organelles such as the Golgi apparatus. ER2 sequences and the like are known. If a particular amino acid sequence is added to a protein known to remain in the endoplasmic reticulum and the protein is significantly transported from the endoplasmic reticulum compared to a protein without such addition, then that particular amino acid sequence can be determined as the endoplasmic reticulum export signal peptide.

In one embodiment of the present disclosure, the amino acid sequence and nucleic acid sequence of the chimeric protein of the present disclosure may have 70% or more, 80% or more, or 90% or more identity or similarity with the reference sequence. Regarding the amino acid sequence or base sequence herein, "70% or more" may be, for example, 70, 75, 80, 85, 90, 95, 96, 97, 98, 99% or more; "80% or more" may be, for example, 80, 85, 90, 95, 96, 97, 98, 99% or more; "90% or more" may be, for example, 90, 95, 96, 97, 98, 99% or more, or may be within the range of any two of the values. As for the "similarity", the proportion of homologous amino acids between two or more amino acid sequences may be calculated according to methods known in the art. Before calculating the proportion, the amino acid sequences of the group of amino acid sequences to be compared are aligned, and gaps are introduced in a portion of the amino acid sequences if necessary to maximize the proportion of identical amino acids. Methods for alignment, methods for calculating proportions, comparison methods, and computer programs related thereto have been well known in the art (e.g., BLAST, GENETYX, etc.). The proportion of the same amino acids is calculated in the case of "identity", whereas the proportion of similar amino acids is calculated in the case of "similarity". Similar amino acids include, but are not limited to, amino acids that can be conservatively substituted.

As used herein, a "polynucleotide that hybridizes under stringent conditions" refers to well-known conditions commonly used in the art. Such a polynucleotide can be obtained by using a polynucleotide selected from the polynucleotides of the present disclosure as a probe and using a colony hybridization method, a plaque hybridization method, a Southern blot hybridization method, or the like. Specifically, the polynucleotide as above means such polynucleotide that can be identified by performing hybridization at 65° C. in the presence of 0.7 to 1.0 M NaCl, using a filter with DNA immobilized from colonies or plaques, and then washing the filter under 65° C. conditions using a SSC (saline-sodiumcitrate) solution with a concentration of 0.1 to 2-fold (note that the composition of the 1-fold SSC solution is 150 mM sodium chloride and 15 mM sodium citrate). For the "stringent conditions", the following conditions, for example, can be adopted: (1) use of low ionic strength and high temperature for washing (e.g., 0.015 M sodium chloride/0.0015 M sodium citrate/0.1% sodium dodecyl sulfate, at 50° C.); (2) use of denaturing agents, such as formamide, during hybridization (e.g., 50% (v/v) formamide and 0.1% bovine serum albumin/0.1% ficoll/0.1% polyvinylpyrrolidone/50 mM sodium phosphate buffer with pH of 6.5, and 750 mM sodium chloride, 75 mM sodium citrate, at 42° C.); or (3) incubation in a solution containing 20% formamide, 5×SSC, 50 mM sodium phosphate (pH 7.6), 5×Denhardt's solution, 10% dextran sulfate and 20 mg/ml denatured shear salmon sperm DNA at 37° C. overnight, followed by washing the filter with 1×SSC at about 37-50° C. Note that the formamide concentration may be 50% or higher. The washing time may be 5, 15, 30, 60 or 120 minutes, or more. Multiple s such as temperature and salt concentration can be considered as factors that affect the stringency of the hybridization reaction, the details of which can be found in Ausubel et al., Current Protocols in Molecular Biology, Wiley Interscience Publishers, (1995). Examples of "highly stringent conditions" are 0.0015M sodium chloride, 0.0015M sodium citrate, at 65-68° C., or 0.015M sodium chloride, 0.0015M sodium citrate and 50% formamide at 42° C. As for hybridization, it can be carried out according to a method described in an experimental document, such as Molecular Cloning 2nd ed., Current Protocols in Molecular Biology, Supplement 1-38, DNA Cloning 1: Core Techniques, A Practical Approach, Second Edition, Oxford University Press (1995), or the like. Here, sequences containing only the A sequence or only the T sequence are preferably excluded from the sequences that hybridize under the stringent conditions. Moderately stringent conditions can be readily determined by one of ordinary skill in the art, based on, for example, the length of the DNA, as shown in Sambrook et al., Molecular Cloning: A Laboratory Manual, No. 3, Vol. 1, 7.42-7.45 Cold Spring Harbor Laboratory Press, 2001. Furthermore, with regard to nitrocellulose filters, included are use of hybridization conditions of 5×SSC, 0.5% SDS, 1.0 mM EDTA (pH 8.0) prewash solution, about 50% formamide at about 40-50° C., and 2×SSC-6×SSC (or other similar hybridization solution, such as Stark's solution, in about 50% formamide at about 42° C.), and washing conditions of about 60° C., 0.5×SSC and 0.1% SDS. Accordingly, the polypeptide used in the present disclosure also includes a polypeptide encoded by a nucleic acid molecule that hybridizes under highly or moderately stringent conditions to the nucleic acid molecule encoding the polypeptide specifically described in the present disclosure.

As used herein, a "purified" substance or biological factor (e.g., nucleic acid or protein) refers to one from which at least some of the factors naturally associated with the substance or biological factor have been removed. Therefore, the purity of the biological factor in the purified biological factor is usually higher (i.e., more enriched) than the purity of the biological factor in the state in which the biological factor is normally present. The term "purified" as used herein means that there are preferably at least 75% by weight, more preferably at least 85% by weight, even more preferably at least 95% by weight, and most preferably at least 98% by weight of biological factors of the same type. The substance or biological factor used in the present disclosure is preferably a "purified" substance. An "isolated" substance or biological factor (e.g., nucleic acid or protein) as used herein refers to one in which a factor naturally associated with the substance or biological factor has been substantially removed. The term "isolated" as used herein varies in accordance with its purpose and therefore does not necessarily have to be expressed in purity, but if necessary, the term means that there are preferably at least 75% by weight, more preferably at least 85% by weight, even more preferably at least 95% by weight, and most preferably at least 98% by weight of biological factors of the same type. The substance used in the present disclosure is preferably an "isolated" substance or biological factor.

As used herein, a "corresponding" amino acid or nucleic acid or moiety refers, in a polypeptide or polynucleotide molecule (e.g., rhodopsin), to an amino acid or nucleotide that has or is expected to have the same effect as a given amino acid or nucleotide or moiety in a polypeptide or polynucleotide that serves as a reference for comparison. In particular, as for an enzyme molecule, it refers to an amino acid that exists at a similar position in the active site and makes a similar contribution to catalytic activity, whereas as for a complex molecule, it refers to a corresponding moiety (e.g., heparan sulfate, etc.). In an antisense molecule, for example, it may be a similar moiety in the ortholog that corresponds to a particular moiety of the antisense molecule. The corresponding amino acid may be, for example, a specific amino acid that is cysteineized, glutathioneized, S—S bond formed, oxidized (e.g., methionine side chain oxidation), formylated, acetylated, phosphorylated, glycosylated, myristylated, and the like. Alternatively, the corresponding amino acid may be the amino acid responsible for dimerization. Such "corresponding" amino acids or nucleic acids may be regions or domains over a range. Thus, in such a case, they are referred to herein as a "corresponding" region or domain. Such a corresponding region or domain is useful when designing a complex molecule in the present disclosure.

As used herein, a "corresponding" gene (e.g., a polynucleotide sequence or molecule) refers, in a certain species, to a gene (e.g., a polynucleotide sequence or molecule) that has or is expected to have the same effect as a given gene in the species of reference for comparison. When there are multiple genes having such an action, those having the same evolutionary origin are referred to as the corresponding genes. Thus, the gene corresponding to a gene may be the ortholog of that gene. Thus, for each human rhodopsin, the corresponding rhodopsin can be found in other animals (particularly mammals). Such corresponding genes can be identified using techniques well known in the art. Thus, for example, with regard to a corresponding gene in a certain animal (e.g., a mouse), the gene of reference for the corresponding gene (e.g., rhodopsin, etc.) can be found by searching a database containing the sequences of the animal, with a sequence of SEQ ID NO: 9 to 16 or the like used as a query sequence.

As used herein, "part", "fragment", or "fragments" refers to a polypeptide or polynucleotide having a sequence length from 1 to n−1 with respect to a full-length polypeptide or polynucleotide (having the length of n). The length of the fragment can be appropriately varied in accordance with its purpose. For example, the lower limit of the length, in the case of a polypeptide, includes 3, 4, 5, 6, 7, 8, 9, 10, 15, 20, 25, 30, 40, 50 and more amino acids, and other lengths represented by integers not specifically listed here (e.g., 11) may also be appropriate as the lower limit. Furthermore, in the case of a polynucleotide, included are 5, 6, 7, 8, 9, 10, 15, 20, 25, 30, 40, 50, 75, 100 and more nucleotides, and other lengths represented by integers not specifically listed here (e.g., 11) may also be appropriate as the lower limit. It is understood herein that any fragment may fall within the scope of the present disclosure when the full length one, for example, functions as a marker or target molecule and the fragment itself also functions as a marker or target molecule.

According to the present disclosure, the term "activity" as used herein refers to the function of a molecule in the broadest sense. The activity generally includes, without intention of limitation, the biological, biochemical, physical or chemical function of the molecule. The activity includes, for example, enzyme activity, ability to interact with other molecules, ability to activate, promote, stabilize, inhibit, suppress or destabilize the function of other molecules, stability, and ability to localize to a specific intracellular location. Where applicable, the term also relates to the function of protein complexes in the broadest sense. As used herein, "biological activity" includes activation of photochemical reactions and the like.

As used herein, a "functional equivalent" refers to any entity having the same target function but a different structure with respect to the original entity of interest. It is thus understood that the functional equivalent of "rhodopsin" or a chimera thereof includes, not the rhodopsin or chimera thereof itself, but a mutant or variant (e.g., an amino acid sequence variant, etc.) of the rhodopsin or chimera thereof having the biological activity of the rhodopsin or chimera thereof, and further includes one that, at the time of action, can be transformed into rhodopsin or an antibody thereof or a mutant or variant of the rhodopsin or a chimera thereof (including, for example, a nucleic acid encoding rhodopsin or a chimera thereof or a mutant or variant of rhodopsin or a chimera thereof, and a vector, cell, etc., containing the nucleic acid). As the functional equivalent of the present disclosure, an amino acid sequence in which one or more amino acids are inserted, substituted and/or deleted, or added to one or both ends thereof can be used. As used herein, an "amino acid sequence in which one or more amino acids are inserted, substituted and/or deleted, or added to one or both ends thereof" means that it has been modified with substitution or the like of a plurality of amino acids that can occur naturally, by a well-known technical method such as site-specific mutagenesis, or by a natural mutation. The modified amino acid sequence can be, for example, one in which 1 to 30, preferably 1 to 20, more preferably 1 to 9, still more preferably 1 to 5, and particularly preferably 1 to 2 amino acids have been inserted, substituted or deleted, or added to one or both ends thereof. The modified amino acid sequence may preferably be such an amino acid sequence that has one or more (preferably one or several or 1, 2, 3, or 4) conservative substitutions in the rhodopsin amino acid sequence.

As used herein, an "agent", "-agent" or "factor" (any of which corresponds to the word, agent, in English) may be used interchangeably in a broad sense, may be any substance or other element (e.g., energy, such as light, radioactivity, heat and electricity) that is capable of achieving the intended objective thereof. Examples of such substances include, without limitation, proteins, polypeptides, oligopeptides, peptides, polynucleotides, oligonucleotides, nucleotides, nucleic acids (including, for example, CDNA, DNA such as genomic DNA, RNA such as mRNA), polysaccharides, oligosaccharides, lipids, organic small molecules (e.g., hormones, ligands, messenger substances, organic small molecules, molecules synthesized by combinatorial chemistry, small molecules that can be used as pharmaceuticals (for example, small molecule ligands), etc.).

For parenteral administration, the agent may be formulated to be contained in a unit dose ampule or multidose container or tube. An additive such as a stabilizer, buffer, preservative, or isotonizing agent may also be included. A formulation for parenteral administration may also be formulated into a powder form that can be dissolved in a suitable carrier (sterilized water or the like) upon use.

Examples of parenteral administration include intravitreal administration, subconjunctival administration, intra-anterior chamber administration, and eye drops, and intravitreal administration is preferred. The composition and the like according to the present disclosure can be used for the treatment, prevention, suppression of progress, and the like by administration to humans using the aforementioned method.

As used herein, "treatment" refers to preventing the exacerbation of a disease or disorder (e.g., retinal degenerative disease) in the event of such a condition, preferably maintaining the status quo, more preferably alleviating, and even more preferably resolving, of the disease or disorder, including the possible exertion of a symptom improving or preventing effect on the patient's disease or one or more symptoms associated with the disease. Conducting diagnosis in advance and appropriate treatment is called "companion treatment", and the diagnostic agent for that purpose is sometimes called "companion diagnostic agent". Since the present disclosure targets genetic disorders, the gene may be tested in advance to treat the patient.

As used herein, a "therapeutic drug (agent)" refers, in a broad sense, to any agent capable of treating a target condition (for example, retinal degenerative disease). In one embodiment of the present disclosure, the "therapeutic drug" may be a pharmaceutical composition comprising an active ingredient and one or more pharmacologically acceptable carriers. The pharmaceutical composition can be manufactured, for example, by mixing an active ingredient with the above carrier and using any method known in the technical field of pharmaceutics. Further, the therapeutic drug is not limited in the form of use as long as it is used for treatment, and may be an active ingredient alone or a mixture of an active ingredient and any component. Further, the shape of the carrier is not particularly limited, and may be, for example, a solid or a liquid (e.g., a buffer solution).

As used herein, "prevention" refers, with regard to a disease or disorder (e.g., retinal degenerative disease), to preventing one from having such a condition before being in such a condition. The agent of the present disclosure can be used for diagnosis, and if necessary, the agent of the present disclosure can be used to prevent, for example, retinal degenerative diseases, or to take preventive measures. As used herein, a "preventive drug (drug)" refers, in a broad sense, to any drug that can prevent a target condition (for example, a disease such as retinal degenerative disease).

As used herein, a "kit" refers to a unit that is usually divided into two or more compartments and provides portions to be provided (e.g., nucleic acids, nucleic acid constructs, cells into which the nucleic acid of interest has been gene-introduced, test agents, diagnostic agents, therapeutic agents, antibodies, labels, instruction manuals, etc.). The form of the present kit is preferable when the purpose thereof is to provide a composition that should not be mixed and provided, but is preferably mixed and used immediately prior to use, for stability reasons or the like. It is advantageous for such a kit to comprise preferably an instruction, or a written explanation, describing how to use the portions to be provided (e.g., nucleic acids, nucleic acid constructs, cells into which the nucleic acid of interest has been gene-introduced, test agents, diagnostic agents, or therapeutic agents) or how the reagent should be processed. When the kit is used as a reagent kit in the present specification, the kit usually includes an instruction or the like describing how to use a test agent, a diagnostic agent, a therapeutic agent, an antibody, and the like.

As used herein, an "active ingredient" refers to an ingredient contained in an amount necessary for the composition of the present disclosure to attain a target effect, such as treatment, prevention or suppression of progress, and may also contain other ingredients as long as the effect is not compromised below the desired level. Further, the pharmaceuticals, compositions and the like of the present disclosure may be those that are formulated. In addition, the route of administration of the pharmaceuticals, compositions, etc. of the present disclosure may be oral or parenteral, and can be appropriately set according to the form of the formulation or the like.

As used herein, an "instruction" (including package inserts, labels used by the US FDA, etc.) refers to such an instruction that describes to a physician or other user how to use a method that uses the present disclosure. The instruction contains words instructing a detection method according to the present disclosure, how to use a diagnostic agent, or administration of pharmaceuticals or the like. In addition, the instruction may include words instructing oral administration or administration to the retina (for example, by injection) as the administration site. This instruction is prepared in accordance with the format prescribed by the regulatory agency of the country in which the present disclosure is implemented (for example, the Ministry of Health, Labor and Welfare in Japan, the Food and Drug Administration (FDA) in the United States, etc.), and the instruction clearly states that it has been approved by the regulatory agency. The instruction is a so-called package insert or label and is usually provided in a paper medium; however, without limitation thereto, the instruction may also be provided in a form of, for example, an electronic medium (e.g., a website provided on the Internet, and e-mail).

Preferred Embodiments

Preferred embodiments of the present disclosure will be described below. It is understood that the embodiments provided below are provided for a better understanding of the present disclosure and the scope of the present disclosure should not be limited to the following description. Therefore, it is clear that those skilled in the art can appropriately make modifications within the scope of the present disclosure in consideration of the description in the present specification. It is also understood that the following embodiments of the present disclosure may be used alone or in combination.

(Novel Construct of Chimeric Rhodopsin)

The present disclosure provides novel nucleic acid constructs of chimeric rhodopsin. Any chimeric rhodopsin capable of achieving the objective of the present disclosure may be used as the chimeric rhodopsin of the present disclosure. The chimeric rhodopsin used in the present disclosure is typically a chimeric protein comprising at least part of an ion-transporting receptor rhodopsin and at least part of a G protein-coupled receptor rhodopsin. To explain a typical example, fusion of part of animal-derived G protein-coupled receptor rhodopsin with part of reusable microbial-derived ion-transporting receptor rhodopsin allows acquiring of high activity via the endogenous G protein by the G protein-coupled receptor while retaining the function of repeated activation possessed by the microbial-derived ion-transporting receptor or ion channeling receptor rhodopsin; and generation of a nucleic acid construct thereof according to the present disclosure allows further improvement of excellent treating, improving, preventing, and progress-suppressing effects on diseases, disorders and symptoms of the retina.

In one aspect, the present disclosure provides nucleic acid constructs encoding a chimeric rhodopsin comprising at least part of an ion-transporting receptor rhodopsin and at least part of a G protein-coupled receptor rhodopsin and a signal sequence. In another aspect, the present disclosure provides nucleic acid constructs of a chimeric rhodopsin comprising at least part of an ion channeling receptor rhodopsin and at least part of a G protein-coupled receptor rhodopsin. As the ion channeling receptor rhodopsin, algal rhodopsins can be used. The algae may be Guillardia theta. In a preferred embodiment, the chimeric rhodopsin according to the present disclosure is such a chimeric rhodopsin in which the amino acid sequences of the second loop on the cytoplasm side and/or the third loop on the cytoplasm side of the amino acid sequences of a Guillardia theta rhodopsin are substituted by the amino acid sequences of the second loop on the cytoplasm side and/or the third loop on the cytoplasm side of the G protein-coupled receptor rhodopsin.

In one embodiment, as the ion-transporting receptor rhodopsin used in the chimeric protein of the present disclosure, an ion pumping receptor rhodopsin and an ion channeling receptor rhodopsin can be used. In a preferred embodiment, the ion-transporting receptor is preferably derived from microorganisms, and those from cyanobacteria (blue-green bacteria), for example, are typical ones. Examples thereof include rhodopsin derived from microorganisms belonging to eubacteria, such as the genus Gloeobacter, and eukaryotes, such as the genus Volvox, genus *Chlamydomonas*, and genus Guillardia. Examples of the genus Gloeobacter include Gloeobacter *violaceus* and the like. Examples of the genus Volvox include Volvox *carteri* and the like. Examples of the genus *Chlamydomonas* include *Chlamydomonas reinhardtii* and the like. Examples of the genus Guillardia include Guillardia theta and the like.

In one embodiment, the G protein-coupled receptor rhodopsin used in the chimeric protein of the present disclosure is typically derived from animals, and rhodopsin derived from rodents, artiodactyls, cloven-hoofed animals, primates, carnivores, and the like is preferable, rhodopsin derived from artiodactyls or primates is more preferable, and rhodopsin derived from primates is still more preferable. In addition, preferable G protein-coupled receptor rhodopsin includes, for example, rhodopsin derived from bovine, human, mouse, rat, cat, dog, pig, sheep, horse and the like. Of these, bovine or human-derived rhodopsin is particularly preferable.

In a certain embodiment, the chimeric protein that the nucleic acid construct etc. of the present disclosure encodes is a chimeric protein comprising part of an ion-transporting receptor rhodopsin and part of a G protein-coupled receptor rhodopsin, and having a seven transmembrane structure. In the present disclosure, the chimeric protein comprising part of an ion-transporting receptor rhodopsin and part of a G protein-coupled receptor rhodopsin is preferably designed to highly exert both: a function of repeatedly activating the ion-transporting receptor rhodopsin; and the G protein activity by the G protein-coupled receptor rhodopsin. From this point of view, the chimeric protein of the present disclosure maintains high activity of both, and particularly exhibits high visual function restoration ability, and thus, the chimeric protein that the nucleic acid construct of the present disclosure preferably encodes a chimeric protein in which the amino acid sequences of the second loop on the cytoplasm side and/or the third loop on the cytoplasm side of the amino acid sequences of the ion-transporting receptor rhodopsin are substituted by the amino acid sequences of the second loop on the cytoplasm side and/or the third loop on the cytoplasm side of the G protein-coupled receptor rhodopsin. Note that the "second loop on the cytoplasm side" and the "third loop on the cytoplasm side" refer to loops located second from the N-terminal side and third from the N-terminal side of the seven loops, respectively.

In one embodiment, it is advantageous for the chimeric protein that the nucleic acid construct of the present disclosure encodes, to have an amino acid sequence in which glutamic acid corresponding to position 132 of the amino acid sequence of SEQ ID NO: 14 (GR) is substituted by glutamine. Examples of glutamine-substituted amino acid sequences include, but are not limited to, the amino acid sequences set forth in SEQ ID NO: 5 and the like.

The method for obtaining a nucleic acid, such as DNA, of the present disclosure is not particularly limited, and examples thereof include a method of obtaining cDNA by reverse transcription from mRNA (for example, RT-PCR method), a method of preparation from genomic DNA, a method of synthesis by chemical synthesis, a method of isolation from a genomic DNA library or a CDNA library, and other known methods (see, for example, Japanese Laid-Open Publication No. Hei 11-29599).

Herein, the chimeric protein that the nucleic acid construct of the present disclosure encodes can be prepared, for example, by using a transformant into which an expression vector comprising the nucleic acid construct etc. of the present disclosure has been introduced. For example, first, this transformant is cultured under appropriate conditions to synthesize a chimeric protein encoded by the nucleic acid construct etc. of the present disclosure. Then, the synthesized protein is recovered from the transformant or the culture medium, thereby acquiring the chimeric protein of the present disclosure.

More specifically, the chimeric protein can be prepared by inserting the nucleic acid construct etc. of the present disclosure as described above into an appropriate expression vector. An "appropriate expression vector" may be any vector that can replicate, retain or self-proliferate in various hosts of prokaryotes and/or eukaryotes, and can be appropriately selected in accordance with the purpose of use. For example, a high copy vector can be selected when a large amount of nucleic acid, such as the nucleic acid construct etc. of the present disclosure, is to be obtained, while an expression vector can be selected when a polypeptide (chimeric protein) is to be obtained. Specific examples thereof include, without particular limitation, known vectors described in Japanese Laid-Open Publication No. Hei 11-29599.

In addition, the expression vector can be used, not only for the synthesis of chimeric proteins, but also for the composition of the present disclosure or the like. Specifically, the composition of the present disclosure or the like may contain an expression vector in which the nucleic acid construct etc. of the present disclosure described above is incorporated, as an active ingredient. The direct introduction of such an expression vector into humans can be used for the treatment, prevention and suppression of progress of diseases, disorders or symptoms of the retina. As the vector in this case, a vector that can be introduced into human cells is used. As such a vector, preferable are, for example, an adeno-associated virus vector (AAV vector) and a lentiviral vector.

The method for introducing the vector can be appropriately selected in accordance with the type of vector and host, and the like. Specific examples thereof include, but are not limited to, known methods such as a protoplast method and a competent method when a bacterium is used as a host (see, for example, Japanese Laid-Open Publication No. Hei11-29599). When the expression vector is used as an active ingredient of the visual function restoring agent or the visual function deterioration preventing agent of the present disclosure, the introduction can be achieved by injecting the above AAV vector or the like into the eye, for example.

The hosts into which the expression vector is introduced may be any hosts that are compatible with the expression vector and can be transformed. Specific examples thereof include, but are not particularly limited to, bacteria, yeast, animal cells, insect cells, and other known natural cells or artificially established cells (see Japanese Laid-Open Publication No. Hei 11-29599), or humans, mice and other animals. The culturing of transformants can be performed by appropriately selecting a medium form from known nutrient media, and by appropriately adjusting the temperature, pH of the nutrient medium, culture time and the like, in accordance with the type of transformant, and the like (see, for example, Japanese Laid-Open Publication No. Hei 11-29599).

The methods for isolating and purifying the chimeric protein are not particularly limited, and examples of such methods include known methods such as methods that utilize solubility, methods that utilize a difference in molecular weights, and methods that utilize electric charges (see, for example, Japanese Laid-Open Publication No. 11-29599).

In one embodiment, the nucleic acid construct etc. of the present disclosure is a polynucleotide that may include any of the following:

(A) a base sequence including a nucleotide sequence set forth in SEQ ID NO: 1, 3 or 26;

(B) a polynucleotide including a nucleic acid sequence including one or more nucleotide substitutions, additions, deletions or a combination thereof, in the nucleic acid sequence set forth in (A);

(C) a polynucleotide including a nucleic acid sequence having at least 70%, at least 80%, at least 90% or at least 95% or more sequence identity with a nucleic acid sequence set forth in (A) or (B), and encoding a polypeptide having biological activity;

(D) a polynucleotide including a nucleic acid sequence that hybridizes with a polynucleotide including a nucleic acid sequence set forth in any one of (A) to (C) or a complementary sequence thereof under stringent conditions, and encoding a polypeptide with biological activity;

(E) a polynucleotide that is an allelic mutant of a nucleic acid sequence of any one of (A) to (D), encoding a polypeptide with biological activity;

(F) a polynucleotide encoded by a polypeptide including an amino acid sequence set forth in SEQ ID NO: 2, 4 or 27;

(G) a polynucleotide including an amino acid sequence including one or more amino acid substitutions, additions, deletions or a combination thereof in the amino acid sequence of (F), and encoding a polypeptide with biological activity;

(H) a polynucleotide having at least 70%, at least 80%, at least 90%, at least 95% or more sequence identity with a nucleic acid sequence set forth in (F) or (G), and encoding a polypeptide with biological activity; or (I) a polynucleotide including a fragment of a nucleic acid sequence set forth in (F) to (H), and the chimeric protein encoded by the polynucleotide has biological activity.

In a specific embodiment, the nucleic acid construct etc. of the present disclosure includes a polypeptide that may encode any of the following polypeptides comprising the following amino acid sequences:

(a) an amino acid sequence set forth in SEQ ID NO: 2, 4 or 27 or a fragment thereof;

(b) a polypeptide including an amino acid sequence including one or more amino acid substitutions, additions, deletions or a combination thereof in the amino acid sequence of (a), and having biological activity;

(c) a polypeptide having at least 70%, at least 80%, at least 90%, at least 95% or more sequence identity with a nucleic acid sequence set forth in (a) or (b), and having biological activity;

(d) a polypeptide including an amino acid sequence set forth in SEQ ID NO: 2, 4 or 27;

(e) a polypeptide encoded by an amino acid sequence including one or more nucleotide substitutions, additions, deletions or a combination thereof in the amino acid sequence of (d) and having biological activity;

(f) a polypeptide encoded by a nucleic acid sequence having at least 70%, at least 80%, at least 90%, at least 95% or more sequence identity with a nucleic acid sequence set forth in (d) or (e), and having biological activity;

(g) a polypeptide encoded by a nucleic acid sequence that hybridizes with a polynucleotide including a nucleic acid sequence set forth in any one of (d) to (f) or a complementary sequence thereof under stringent conditions, and having biological activity;

(h) a polypeptide encoded by an allelic mutant of a nucleic acid sequence of any one of (d) to (g), and having biological activity; or (i) a polypeptide including a fragment of an amino acid sequence set forth in (a) to (h), and the nucleic acid construct etc., with biological activity; or the chimeric protein of the present disclosure may include an amino acid sequence encoded by any of the following nucleic acids:

(aa) a nucleic acid having a base sequence encoding an amino acid sequence set forth in SEQ ID NO: 2, 4 or 27 or a base sequence set forth in SEQ ID NO: 1, 3 or 26;

(bb) a nucleic acid having a base sequence that can hybridize under stringent conditions with a base sequence encoding an amino acid sequence set forth in SEQ ID NO: 2, 4 or 27 or a base sequence complementary to a base sequence set forth in SEQ ID NO: 1, 3 or 26;

(cc) a nucleic acid having a base sequence encoding an amino acid sequence in which one or more amino acids are substituted, deleted and/or added in the amino acid sequence set forth in SEQ ID NO: 2, 4 or 27, and having biological activity;

(dd) a nucleic acid consisting of a base sequence encoding an amino acid sequence having 90% or more homology with an amino acid sequence set forth in SEQ ID NO: 2, 4 or 27, and having biological activity; or (aaa) a base sequence set forth in SEQ ID NO: 1, 3 or 26 or a fragment thereof;

(bbb) a nucleic acid having at least 70%, at least 80%, at least 90%, or at least 95% identity to (aaa);

(ccc) a base sequence with one or more nucleotides substituted, added and/or deleted with respect to (aaa) or (bbb); and (ddd) a base sequence that hybridizes to any of (aaa) to (ccc) under stringent conditions, and the chimeric protein also has biological activity.

In a particular embodiment, the nucleic acid of the present disclosure may be a nucleic acid sequence at least six or more triplets in common with the nucleic acid sequence set forth in SEQ ID NO: 1, 3 or 26. In another embodiment, the nucleic acid construct of the present disclosure may include a nucleic acid sequence having at least one of the triplets encoding amino acids 6, 9-13, 15, 16, 18-22, 27-29, 31-36, 39, 40, 43, 45, 48, 50, 51, 53-55, 58, 59, 61, 65-73, 75-84, 86, 88, 89, 93, 97, 98, 100, 101, 104, 106-108, 110, 112, 114, 115, 122, 123, 125, 128, 131, 133, 139, 143, 145, 146, 155, 157, 162, 165, 167, 169-171, 174, 176, 179, 182, 183, 186-189, 193-198, 204, 205, 207, 209, 212, 215, 216, 218-220, 224, 225, 227, 228, 230, 231, 233-235, 238, 240, 242, 243, 246, 247, 249, 251, 253-255, 257-259, 261-264, 266-270, 272, 273, 275, 276, 279, 281-287, 289-291, 296-299, 302-305, 307-316, 318, 319, and 321-330 in common with the nucleic acid sequence set forth in SEQ ID NO: 1, 3 or 26, of the nucleic acid sequences encoding the same amino acids as SEQ ID NO: 1, 3 or 26.

The nucleic acid sequence encoding the second loop on the cytoplasmic side of the G protein-coupled receptor rhodopsin described above is preferably the one having any of the following nucleic acid sequences:

(A) a base sequence including a nucleotide sequence set forth in SEQ ID NO: 17 or 18;

(B) a polynucleotide comprising a nucleic acid sequence including substitutions, additions, deletions or a combination thereof of one or more nucleotides, in the nucleic acid sequence set forth in (A);

(C) a polynucleotide comprising a nucleic acid sequence having at least 70%, at least 80%, at least 90% or at least 95% or more sequence identity with a nucleic acid sequence set forth in (A) or (B), and encoding a polypeptide having biological activity;

(D) a polynucleotide comprising a nucleic acid sequence that hybridizes with a polynucleotide including a nucleic acid sequence set forth in any one of (A) to (C) or a complementary sequence thereof under stringent conditions, and encoding a polypeptide having biological activity;

(E) a polynucleotide that is an allelic mutant of a nucleic acid sequence of any one of (A) to (D), encoding a polypeptide having biological activity;

(F) a polynucleotide encoded by a polypeptide including an amino acid sequence set forth in SEQ ID NO: 19 or 25;

(G) a polynucleotide including an amino acid sequence including one or more amino acid substitutions, additions, deletions or a combination thereof in the amino acid sequence of (F), and encoding a polypeptide having biological activity;

(H) a polynucleotide having at least 70%, at least 80%, at least 90%, at least 95% or more sequence identity with a nucleic acid sequence set forth in (F) or (G), and encoding a polypeptide with biological activity; or (I) a polynucleotide comprising a fragment of a nucleic acid sequence set forth in (F) to (H).

In a particular embodiment, the nucleic acid sequence encoding the second loop on the cytoplasmic side of the G protein-coupled receptor rhodopsin described above is preferably a nucleic acid sequence having at least two triplets in common with the nucleic acid sequence set forth in SEQ ID NO: 17.

Alternatively, the second loop on the cytoplasm side of the G protein-coupled receptor rhodopsin described above is preferably a loop having an amino acid sequence encoded by any of the nucleic acids described below:

(i) a nucleic acid having a base sequence encoding an amino acid sequence set forth in SEQ ID NO: 19 or 25;

(ii) a nucleic acid having a base sequence that can hybridize under stringent conditions with a base sequence complementary to a base sequence encoding an amino acid sequence set forth in SEQ ID NO: 19 or 25;

(iii) a nucleic acid having a base sequence encoding an amino acid sequence in which one or more amino acids are substituted, deleted and/or added in an amino acid sequence set forth in SEQ ID NO: 19 or 25; and (iv) a nucleic acid consisting of a base sequence encoding an amino acid sequence having 70% or more homology with an amino acid sequence set forth in SEQ ID NO: 19 or 25, or the nucleic acid encoding the second loop on the cytoplasm side of the G protein-coupled receptor rhodopsin is preferably any of the below.

In a particular embodiment, the nucleic acid sequence encoding the third loop on the cytoplasmic side of the G protein-coupled receptor rhodopsin described above is preferably a nucleic acid sequence having at least one triplet in common with the nucleic acid sequence set forth in SEQ ID NO: 19 or 25.

(i) a nucleic acid having a base sequence encoding an amino acid sequence set forth in SEQ ID NO: 19 or 25;

(ii) a nucleic acid having a base sequence that can hybridize under stringent conditions with a base sequence complementary to a base sequence encoding an amino acid sequence set forth in SEQ ID NO: 19 or 25;

(iii) a nucleic acid having a base sequence encoding an amino acid sequence in which one or more amino acids are substituted, deleted and/or added in an amino acid sequence set forth in SEQ ID NO: 19 or 25; and (iv) a nucleic acid consisting of a base sequence encoding an amino acid sequence having 90% or more homology with an amino acid sequence set forth in SEQ ID NO: 19 or 25;

(x) a nucleic acid having a base sequence set forth in SEQ ID NO: 19 or 25 or a fragment thereof;

(y) a nucleic acid having at least 70%, at least 80%, at least 90% or at least 95% identity to (x);

(z) a nucleic acid with one or more nucleotides substituted, added and/or deleted with respect to (x) or (y); and (w) a nucleic acid that hybridizes to any of (x) to (z) under stringent conditions, and the loop also has biological activity.

The nucleic acid sequence encoding the third loop on the cytoplasmic side of the G protein-coupled receptor rhodopsin described above is preferably the one having any of the following nucleic acid sequences:

(A) a base sequence including a nucleotide sequence set forth in SEQ ID NO: 20 or 21;

(B) a polynucleotide including a nucleic acid sequence including substitutions, additions, deletions or a combination thereof of one or more nucleotides, in the nucleic acid sequence set forth in (A);

(C) a polynucleotide including a nucleic acid sequence having at least 70%, at least 80%, at least 90% or at least 95% or more sequence identity with a nucleic acid sequence set forth in (A) or (B), and encoding a polypeptide having biological activity;

(D) a polynucleotide including a nucleic acid sequence that hybridizes with a polynucleotide including a nucleic acid sequence set forth in any one of (A) to (C) or a complementary sequence thereof under stringent conditions, and encoding a polypeptide having biological activity;

(E) a polynucleotide that is an allelic mutant of a nucleic acid sequence of any one of (A) to (D), encoding a polypeptide having biological activity;

(F) a polynucleotide encoded by a polypeptide including an amino acid sequence set forth in SEQ ID NO: 22;

(G) a polynucleotide including an amino acid sequence including one or more amino acid substitutions, additions, deletions or a combination thereof in the amino acid sequence of (F), and encoding a polypeptide having biological activity;

(H) a polynucleotide having at least 70%, at least 80%, at least 90% or more sequence identity with a nucleic acid sequence set forth in (F) or (G), and encoding a polypeptide with biological activity; or (I) a polynucleotide including a fragment of a nucleic acid sequence set forth in (F) to (H).

The third loop on the cytoplasm side of the G protein-coupled receptor rhodopsin described above is preferably a loop having an amino acid sequence encoded by any of the following nucleic acids:

(l) a nucleic acid having a base sequence encoding the amino acid sequence set forth in SEQ ID NO: 22;

(k) a nucleic acid having a base sequence that can hybridize under stringent conditions with a base sequence complementary to a base sequence encoding the amino acid sequence set forth in SEQ ID NO: 22;

(m) a nucleic acid having a base sequence encoding an amino acid sequence in which one or more amino acids are substituted, deleted and/or added in the amino acid sequence set forth in SEQ ID NO: 22; and (n) a nucleic acid consisting of a base sequence encoding an amino acid sequence having at least 70%, at least 80%, at least 90% or at least 95% or more homology with the amino acid sequence set forth in SEQ ID NO: 22.

Alternatively, the nucleic acid encoding the third loop on the cytoplasm side of the G protein-coupled receptor rhodopsin is preferably any of the following:

(l) a nucleic acid having a base sequence encoding the amino acid sequence set forth in SEQ ID NO: 22;

(k) a nucleic acid having a base sequence that can hybridize under stringent conditions with a base sequence complementary to a base sequence encoding the amino acid sequence set forth in SEQ ID NO: 22;

(m) a nucleic acid having a base sequence encoding an amino acid sequence in which one or more amino acids are substituted, deleted and/or added in the amino acid sequence set forth in SEQ ID NO: 22;

(n) a nucleic acid consisting of a base sequence encoding an amino acid sequence having at least 70%, at least 80%, at least 90% or at least 95% or more homology with the amino acid sequence set forth in SEQ ID NO: 22;

(xx) a nucleic acid having a base sequence set forth in SEQ ID NO: 20 or a fragment thereof;

(yy) a nucleic acid having at least 70%, at least 80%, at least 90% or at least 95% identity to (xx);

(zz) a nucleic acid with one or more nucleotides substituted, added and/or deleted with respect to (xx) or (yy); or (ww) a nucleic acid that hybridizes to any of (xx) to (zz) under stringent conditions, and the loop also has biological activity.

The present disclosure also provides a nucleic acid having one of the following:

(A) a base sequence encoding an amino acid sequence set forth in SEQ ID NO: 2, 4 or 27 or a fragment thereof;

(B) a base sequence set forth in SEQ ID NO: 1, 3 or 26 or a fragment thereof;

(C) a nucleic acid having at least 70%, at least 80%, at least 90% or at least 95% identity to (A) or (B);

(D) a base sequence with one or more nucleotides substituted, added and/or deleted with respect to any of (A) to (C); and (E) a base sequence that hybridizes to any of (A) to (D) under stringent conditions, where the protein encoded by the nucleic acid has biological activity.

In one aspect, the present disclosure provides a nucleic acid including a nucleic acid sequence encoding a chimeric protein of an ion channeling receptor rhodopsin and a G protein-coupled receptor rhodopsin. Examples of the ion channeling receptor rhodopsin include, without limitation, rhodopsin derived from microorganisms belonging to eubacteria, such as the genus Volvox, genus *Chlamydomonas*, and genus Guillardia. In a preferable embodiment, the ion channeling receptor rhodopsin is a rhodopsin of Guillardia theta as the genus Guillardia, and the G protein-coupled receptor rhodopsin is a bovine rhodopsin.

In one embodiment, the nucleic acid construct etc. of the present disclosure is a polynucleotide that may any of the following:

(A) a base sequence including the nucleotide sequence set forth in SEQ ID NO: 7;

(B) a polynucleotide including a nucleic acid sequence including one or more nucleotide substitutions, additions, deletions or a combination thereof, in the nucleic acid sequence set forth in (A);

(C) a polynucleotide including a nucleic acid sequence having at least 70%, at least 80%, at least 90% or at least 95% or more sequence identity with a nucleic acid sequence set forth in (A) or (B), and encoding a polypeptide having biological activity;

(D) a polynucleotide including a nucleic acid sequence that hybridizes with a polynucleotide including a nucleic acid sequence set forth in any one of (A) to (C) or a complementary sequence thereof under stringent conditions, and encoding a polypeptide having biological activity;

(E) a polynucleotide that is an allelic mutant of a nucleic acid sequence of any one of (A) to (D), encoding a polypeptide having biological activity;

(F) a polynucleotide encoded by a polypeptide including an amino acid sequence set forth in SEQ ID NO: 8;

(G) a polynucleotide including an amino acid sequence including one or more amino acid substitutions, additions, deletions or a combination thereof in the amino acid sequence of (F), and encoding a polypeptide having biological activity;

(H) a polynucleotide having at least 70%, at least 80%, at least 90%, at least 95% or more sequence identity with a nucleic acid sequence set forth in (F) or (G), and encoding a polypeptide with biological activity; or (I) a polynucleotide including a fragment of a nucleic acid sequence set forth in (F) to (H), and the chimeric protein encoded by the polynucleotide has biological activity.

In a particular embodiment, the nucleic acid of the present disclosure may be a nucleic acid sequence having at least fourteen or more triplets in common with the nucleic acid sequence set forth in SEQ ID NO: 7. In another embodiment, the nucleic acid construct of the present disclosure may include a nucleic acid sequence having at least one of the triplets encoding amino acids 1, 2, 4-9, 11-17, 21, 22, 27-30, 33, 34, 36-41, 43, 45, 48, 49, 51, 54, 56-58, 60, 63, 65, 68, 70, 71-75, 77-78, 81, 83, 84, 86, 89, 90, 92, 93, 95, 97-99, 102, 103, 111, 113, 114, 123, 125, 130, 131-137, 139, 142, 143, 146, 148-153, 156, 160, 161, 165, 167, 168, 170, 171, 174-176, 180, 182, 183, 187, 188, 190, 191, 196, 197, 199, 200, 202, 204, 208, 212-214, 217, 219, 226, 229, 232, 236-238, 240, 242, 243, 247, 248, 251, 252, 258, 263-265, 267, 269, 271, 272, 274, 276-280, 282-284, 289, 290, 291, 294, 297-299, 302, 304, 307 and 310 in common with the nucleic acid sequence set forth in SEQ ID NO: 7, of the nucleic acid sequences encoding the same amino acids as SEQ ID NO: 7.

In a specific embodiment, the nucleic acid construct etc. of the present disclosure includes a polypeptide that may encode any of the following polypeptides including amino acid sequences:

(a) an amino acid sequence set forth in SEQ ID NO: 8 or a fragment thereof;

(b) a polypeptide including an amino acid sequence including one or more amino acid substitutions, additions, deletions or a combination thereof in the amino acid sequence of (a), and having biological activity;

(c) a polypeptide having at least 70%, at least 80%, at least 90%, at least 95% or more sequence identity with a nucleic acid sequence set forth in (a) or (b), and having biological activity;

(d) a polypeptide including an amino acid sequence set forth in SEQ ID NO: 8;

(e) a polypeptide encoded by an amino acid sequence including one or more nucleotide substitutions, additions, deletions or a combination thereof in the amino acid sequence of (d) and having biological activity;

(f) a polypeptide encoded by a nucleic acid sequence having at least 70%, at least 80%, at least 90%, at least 95% or more sequence identity with a nucleic acid sequence set forth in (d) or (e), and having biological activity;

(g) a polypeptide encoded by a nucleic acid sequence that hybridizes with a polynucleotide including a nucleic acid sequence set forth in any one of (d) to (f) or a complementary sequence thereof under stringent conditions, and having biological activity;

(h) a polypeptide encoded by an allelic mutant of a nucleic acid sequence of any one of (d) to (g), and having biological activity; or (i) a polypeptide including a fragment of an amino acid sequence set forth in (a) to (h), and the nucleic acid construct etc. also has biological activity; or the chimeric protein of the present disclosure may include an amino acid sequence encoded by any of the following nucleic acids:

(aa) a nucleic acid having a base sequence encoding an amino acid sequence set forth in SEQ ID NO: 8 or a base sequence set forth in SEQ ID NO: 7;

(bb) a nucleic acid having a base sequence that can hybridize under stringent conditions with a base sequence encoding an amino acid sequence set forth in SEQ ID NO: 8 or a base sequence complementary to a base sequence set forth in SEQ ID NO: 7;

(cc) a nucleic acid having a base sequence encoding an amino acid sequence in which one or more amino acids are substituted, deleted and/or added in the amino acid sequence set forth in SEQ ID NO: 8, and having biological activity;

(dd) a nucleic acid consisting of a base sequence encoding an amino acid sequence having 90% or more homology with an amino acid sequence set forth in SEQ ID NO: 8, and having biological activity; or (aaa) a base sequence set forth in SEQ ID NO: 7 or a fragment thereof;

(bbb) a nucleic acid having at least 70%, at least 80%, at least 90%, or at least 95% identity to (aaa);

(ccc) a base sequence with one or more nucleotides substituted, added and/or deleted with respect to (aaa) or (bbb); and (ddd) a base sequence that hybridizes to any of (aaa) to (ccc) under stringent conditions, and the chimeric protein also has biological activity.

The present disclosure also provides a nucleic acid having one of the following:

(A) a base sequence encoding an amino acid sequence set forth in SEQ ID NO: 8 or a fragment thereof;

(B) a base sequence set forth in SEQ ID NO: 7 or a fragment thereof;

(C) a nucleic acid having at least 70%, at least 80%, at least 90% or at least 95% identity to (A) or (B);

(D) a base sequence with one or more nucleotides substituted, added and/or deleted with respect to any of (A) to (C); and (E) a base sequence that hybridizes to any of (A) to (D) under stringent conditions, where the protein encoded by the nucleic acid has biological activity.

As used herein, typical examples of "biological activity" can include the function of the G protein-coupled receptor (e.g., membrane transfer efficiency) that the loop thereof has, and in addition, the prevention and suppression of progress of retinal diseases (e.g., retinitis pigmentosa), the visual cognitive improvement in light-dark behavioral functions (e.g., determination functions, improvement in bright spot evading functions, and/or crisis avoidance functions), and the function capable of exerting effects for augmenting visual acuity. The biological activity in the case of loops can include, but are not limited to, functions such as conformational compatibility and membrane transfer efficiency. Alternatively, the functions of the loop may be evaluated by the functions of the incorporated protein as a whole (herein, rhodopsin).

In the present disclosure, the chimeric protein of the present disclosure and the nucleic acid encoding the same have been found to be used for the purpose of preventing or suppressing the progress of diseases, disorders or symptoms of the retina, for the purpose of improving visual cognitive behavioral functions (e.g., improvement in light-dark determination functions, improvement in bright spot evading functions, and/or crisis avoidance functions) or object recognition functions, and for the purpose of providing visual function augmenting effects, such as improving the visual acuity.

While one of the eye diseases for which there is no cure to date is retinitis pigmentosa, atrophic age-related macular degeneration, and other retinal degenerative diseases, radical cures for these diseases may be provided by the present disclosure. Globally, the total number of patients with these diseases is said to exceed 130 million, while retinitis pigmentosa is the third leading cause, and age-related macular degeneration is the fourth leading cause, of acquired blindness in Japan. The development of a therapeutic method has been long desired due to the large number of such patients and the severity of visual impairment, which may be solved by the present disclosure.

Like the central nervous system, the photoreceptor cells, which are the primary neurons of vision, cannot be regstored once they are lost. In retinitis pigmentosa and atrophic age-related macular degeneration, however, bipolar cells and retinal ganglion cells, which are the secondary and tertiary neurons of vision, are retained, which is considered to be one of the factors for the effectiveness of the present disclosure. The present disclosure is a gene transfer therapy using optogenetics, which can be expected to have a safe and long-term visual sense restoration effect with little invasiveness. Highly efficient and safe visual sense restoration has become possible by using the original, more physiological phototransmission pathways the that utilize endogenous G protein signal cascade and channels, which is completely different from the conventional method of introducing photoactivated ion channels. The conventional method of introducing photoactivated ion channels has been restoration for patients with already advanced retinal degeneration, whereas the present method does not require the metabolic restoration system of retinal called Visual Cycle, which is necessary for normal light transmission. Accordingly, the present method can also be expected to have an effect of suppressing the progress of retinal degeneration. This has proved that the present disclosure can be applied, not only to patients with advanced retinal degeneration, but also to the prevention of progress in patients in the early stage.

In one aspect, the present disclosure provides a nucleic acid including: a nucleic acid sequence encoding a chimeric protein of an ion-transporting receptor rhodopsin and a G protein-coupled receptor rhodopsin; and a nucleic acid sequence encoding a signal sequence. In one embodiment, the signal sequence is an endoplasmic reticulum transfer signal sequence or an endoplasmic reticulum export signal sequence. In a particular embodiment, the signal sequence is an endoplasmic reticulum export signal sequence. In a further particular embodiment, an endoplasmic reticulum export signal is an ER2 signal.

The endoplasmic reticulum export signal has been reported to have a positive effect on protein membrane transport (FEBS Lett. 2001 Mar. 30; 493 (2-3): 129-33). Although the evaluation with ER2 alone has not been performed, it has been reported that the peak current increases by about 1.7 times. On the other hand, in Nature. 2010 Jan. 7; 463 (7277); 98-102, the current enhancing effect by adding the signal sequence has not been found.

In one embodiment, the nucleic acid of the present disclosure includes or consists of a nucleic acid sequence set forth in SEQ ID NO: 1 or 26. In some embodiments, the nucleic acid of the present disclosure includes or consists of a nucleic acid sequence having at least 80%, 85%, 90%, 91%, 92%, 93%, 94%, 95%, 96%, 97%, 98% or 99% sequence identity to the nucleic acid sequence set forth in SEQ ID NO: 1 or 26.

In one embodiment, the nucleic acid of the present disclosure may further include a nucleic acid sequence encoding a FLAG tag. In one embodiment, the nucleic acid of the present disclosure includes a nucleic acid sequence set forth in SEQ ID NO: 3. In some embodiments, the nucleic acid of the present disclosure includes a nucleic acid sequence having at least 808, 85%, 90%, 91%, 92%, 93%, 94%, 95%, 96%, 97%, 98% or 99% sequence identity to the nucleic acid sequence set forth in SEQ ID NO: 3.

In one aspect, the present disclosure provides a polypeptide including: a chimeric protein of an ion-transporting receptor rhodopsin and a G protein-coupled receptor rhodopsin; and a signal sequence. In some embodiments, the polypeptide of the present disclosure consisting of a chimeric protein of an ion-transporting receptor rhodopsin and a G protein-coupled receptor rhodopsin and a signal sequence. In another embodiment, the signal sequence is an endoplasmic reticulum import signal sequence or an endoplasmic reticulum export signal sequence. In a particular embodiment, the signal sequence is an endoplasmic reticulum export signal sequence.

In one embodiment, the polynucleotide of the present disclosure includes or consists of a sequence encoding an amino acid sequence set forth in SEQ ID NO: 2 or 27. In a particular embodiment, the polynucleotide of the present disclosure includes or consists of a polynucleotide having at least 80%, 858, 90%, 91%, 92%, 93%, 94%, 95%, 96%, 97%, 98% or 99% sequence identity to the nucleotide sequence set forth in SEQ ID NO: 2 or 27.

In one embodiment, the present disclosure includes or consists of a polypeptide encoded by the polynucleotide of the present disclosure. In some embodiments, the polypeptide of the present disclosure includes or consists of an amino acid sequence set forth in SEQ ID NO: 2 or 27. In a particular embodiment, the polypeptide encoded by the polypeptide of the present disclosure includes or consists of a sequence having at least 80%, 85%, 90%, 91%, 92%, 93%, 94%, 95%, 96%, 97%, 98% or 99% sequence identity to the amino acid sequence set forth in SEQ ID NO: 2 or 27.

In one embodiment, the present disclosure includes or consists of the nucleotide sequence of the present disclosure. In some embodiments, the nucleic acid of the present disclosure includes or consists of a nucleotide sequence set forth in SEQ ID NO: 4. In a particular embodiment, the nucleic acid of the present disclosure includes or consists of a nucleic acid having at least 80%, 85%, 90%, 918, 92%, 93%, 94%, 95%, 96%, 97%, 98% or 99% sequence identity to the amino acid sequence set forth in SEQ ID NO: 4.

In one aspect, the present disclosure provides a nucleic acid including a nucleic acid sequence encoding a chimeric protein of an ion channeling receptor rhodopsin and a G protein-coupled receptor rhodopsin. In one embodiment, the nucleic acid of the present disclosure may include a nucleic acid sequence encoding a signal sequence. In a particular embodiment, the signal sequence is an endoplasmic reticulum transfer signal sequence or an endoplasmic reticulum import signal sequence. In a particular embodiment, the signal sequence is an endoplasmic reticulum export signal sequence.

In one embodiment, the nucleic acid of the present disclosure includes or consists of the nucleic acid sequence set forth in SEQ ID NO: 7. In some embodiments, the nucleic acid of the present disclosure includes or consists of a nucleic acid sequence having at least 80%, 85%, 90%, 91%, 92%, 93%, 94%, 95%, 96%, 978, 98% or 99% sequence identity to the amino acid sequence set forth in SEQ ID NO: 7.

In one embodiment, the nucleic acid of the present disclosure may include a nucleic acid sequence encoding any FLAG tag.

In one aspect, the present disclosure provides a polypeptide including: a chimeric protein of an ion channeling receptor rhodopsin and a G protein-coupled receptor rhodopsin; and a signal sequence. In some embodiments, the polypeptide of the present disclosure consisting of: a chimeric protein of an ion channeling receptor rhodopsin and a G protein-coupled receptor rhodopsin; and a signal sequence. In another embodiment, the signal sequence is an endoplasmic reticulum import signal sequence or an endoplasmic reticulum export signal sequence. In a particular embodiment, the signal sequence is an endoplasmic reticulum export signal sequence.

In one embodiment, the polypeptide of the present disclosure includes or consists of the amino acid sequence set forth in SEQ ID NO: 8. In a particular embodiment, the polypeptide of the present disclosure includes or consists of a polypeptide having at least 80%, 85%, 90%, 91%, 92%, 93%, 94%, 95%, 96%, 97%, 98% or 99% sequence identity to the amino acid sequence set forth in SEQ ID NO: 8.

In one embodiment, the present disclosure includes or consists of a nucleic acid encoding the polypeptide of the present disclosure. In some embodiments, the nucleic acid of the present disclosure includes or consists of a nucleic acid encoding the amino acid sequence set forth in SEQ ID NO: 8. In a particular embodiment, the nucleic acid of the present disclosure includes or consists of a nucleic acid encoding a polypeptide having at least 80%, 85%, 90%, 91%, 92%, 93%, 94%, 95%, 96%, 97%, 98% or 99% sequence identity to the amino acid sequence set forth in SEQ ID NO: 8.

In one aspect, the present disclosure provides a nucleic acid construct including: a nucleic acid of the present disclosure; and a nucleic acid operably linked to the nucleic acid to enable expression in a cell. In one embodiment, the nucleic acid construct of the present disclosure further includes j a vector. In some embodiments, the vector is selected from the group consisting of a viral vector, a plasmid vector, a cosmid vector, an artificial chromosome vector and a phosmid vector. In a particular embodiment, the vector is a viral vector. In another embodiment, the viral vector is selected from the group consisting of an adenovirus vector, an adeno-associated virus vector (AAV), a retro viral vector and a lentiviral vector. In a particular embodiment, the viral vector is an adeno-associated virus vector (AAV).

In one embodiment, the AAV is AAV-DJ, AAV-2 or AAV-6. In a particular embodiment, the AAV may be AAV-DJ or AAV-6. The efficiency of infection of bipolar cells is higher in the DJ-type and type 6 AAV than in type 2 AAV.

In one aspect, the present disclosure provides a composition use in gene-introduction including a nucleic acid or a nucleic acid construct of the present disclosure. In one embodiment, the composition use in gene-introduction of the present disclosure is administered by injection. In another embodiment, the composition use in gene-introduction of the present disclosure is administered intravitreally. In a particular embodiment, the composition use in gene-introduction of the present disclosure may be provided together with a storage solution. In some embodiments, the storage solution may be a buffer solution. In other embodiments, the composition use in gene-introduction of the present disclosure may be provided in a state of being stored in a container. In a particular embodiment, the container for storing the composition use in gene-introduction of the present disclosure may be a syringe.

In another aspect, the present disclosure provides a cell including the nucleic acid, polypeptide or nucleic acid construct of the present disclosure. In some embodiments, the cell of the present disclosure may be a retinal cell. In another embodiment, the cell of the present disclosure may be provided as a cell preparation. The cell preparation includes a cell and a cell-preserving solution. In some embodiments, the cell-preserving solution may be a culture medium or a buffer. In other embodiments, the cell of the present disclosure may be provided in a state of being stored in a container. In a particular embodiment, the container for storing the cell of the present disclosure may be a syringe.

In other aspects, the present disclosure provides a pharmaceutical composition including the nucleic acid, polypeptide, nucleic acid construct, composition use in gene-introduction or cell of the present disclosure. In one embodiment, the pharmaceutical composition of the present disclosure may be a pharmaceutical composition for use in treating, preventing or suppressing the progress of a disease, disorder or symptom of the retina. In one embodiment, the pharmaceutical composition of the present disclosure may be a pharmaceutical composition for use in improving a visual cognitive behavioral function. In one embodiment, the pharmaceutical composition of the present disclosure may be a pharmaceutical composition for use in enhancing a visual function. In one embodiment, the pharmaceutical composition of the present disclosure may be a pharmaceutical composition for use in improving an object recognition function. The prevention or suppression of progress of diseases, disorders or symptoms of the retina, represented by the suppression of the progress of retinitis pigmentosa, in the present disclosure, has been confirmed by the demonstration in the experiments shown in Examples 1 to 10.

(Improvement in Visual Cognitive Behavioral Function)

Functions such as improving visual cognitive behavioral functions (e.g., improvement in light-dark determination functions, improvement in bright spot evading functions, and/or crisis avoidance functions) have been verified with experimental models in the present disclosure, where the present disclosure is considered to exert significant effects. The effects for the visual cognitive behavioral functions (e.g., improvement in light-dark determination functions, improvement in bright spot evading functions, and/or crisis avoidance functions) have been demonstrated as a result of the testing by the light-dark box selection test (LDT) demonstrated in Example 5. The visual cognitive behavioral functions are such functions that can be confirmed by, not only confirming the photosensitivity of visual organs, but also verifying whether the functions actually appear as actions in animal models, etc. One of the achievements of the present disclosure is considered to be the verification achieved by the experiment as in Example 5. The improvement in the visual cognitive behavioral functions includes improvement, enhancement, augmentation or the like of visual acuity, contrast sensitivity, light-dark adaptation, color vision, etc.

(Visual Function Enhancement and Visual Acuity Improvement)

The function of improving visual acuity has been verified with experimental models in the present disclosure, where the present disclosure is considered to exert significant effects. The enhancement of visual functions, such as improvement in visual acuity, has been confirmed by the demonstration in the experiments of the visual evoked potential VEP represented by Example 4.

(Improvement in Object Recognition Functions)

Functions such as improving object recognition functions have been verified with experimental models in the present disclosure, where the present disclosure is considered to exert significant effects. The functions such as improving object recognition functions have been confirmed by the demonstration in the experiments of the object recognition test ORT represented by Example 6. It can be seen that, in the visual evoked potential VEP experiment, the input of the light stimulus reached the central nervous system (brain), and it was output to the behavior as a repellent reaction in the LDT. However, it was not known whether or not the visual acuity of the level at which an object could be recognized was restored. In the results shown in Example 6, it is very clinically significant that the recovery of visual acuity at a level at which an object can be recognized was confirmed.

In one aspect, the present disclosure provides a method for treating, preventing or suppressing the progress of an eye disease, disorder or symptom of a subject, the method including administering a therapeutically effective amount of the nucleic acid, polypeptide, nucleic acid construct, gene-introducing composition, cell or pharmaceutical composition of the present disclosure to a subject.

In one embodiment, the disease, disorder or symptom is retinal degenerative disease. As the retinal degenerative disease, for example, retinitis pigmentosa and age-related macular degeneration are preferably advantageous, and retinitis pigmentosa is more preferably advantageous.

In a preferred embodiment, the retinitis pigmentosa targeted by the present disclosure is autosomal dominantly inherited and is preferably RHO autosomal preferentially inherited.

In a preferred embodiment, the present disclosure is used for the purpose of preventing or suppressing the progress of retinitis pigmentosa.

In a preferred embodiment, the present disclosure is preferably, but not limited to, administered to a subject before or immediately after the onset of a disease, disorder or symptom, such as, within 1 year, preferably within 6 months, within 3 months or within 1 month, from the onset (e.g., when subjective symptoms appear), for example.

In one particular embodiment, the composition or vector of the present disclosure is administered once. It has been confirmed that the present disclosure is effective when administered once, where the compliance with patients is considered to be favorable.

In one particular embodiment, the amount of the vector used in the present disclosure is $0.1 \times 10^{11}$ to $10 \times 10^{11}$ vg/eye unit dose, where the lower limit thereof may be, for example, $0.01 \times 10^{11}$ vg/eye, $0.02 \times 10^{11}$ vg/eye, $0.03 \times 10^{11}$ vg/eye, $0.04 \times 10^{11}$ vg/eye, $0.05 \times 10^{11}$ vg/eye, $0.06 \times 10^{11}$ vg/eye, $0.07 \times 10^{11}$ vg/eye, $0.08 \times 10^{11}$ vg/eye, $0.09 \times 10^{11}$ vg/eye, $0.1 \times 10^{11}$ vg/eye, $0.2 \times 10^{11}$ vg/eye, $0.3 \times 10^{11}$ vg/eye, $0.4 \times 10^{11}$ vg/eye, $0.5 \times 10^{11}$ vg/eye or the like, while the upper limit thereof may be, for example, $2 \times 10^{11}$ vg/eye, $3 \times 10^{11}$ vg/eye, $4 \times 10^{11}$ vg/eye, $5 \times 10^{11}$ vg/eye, $6 \times 10^{11}$ vg/eye, $7 \times 10^{11}$ vg/eye, $8 \times 10^{11}$ vg/eye, $9 \times 10^{11}$ vg/eye, $10 \times 10^{11}$ vg/eye, $15 \times 10^{11}$ vg/eye, $20 \times 10^{11}$ vg/eye, $30 \times 10^{11}$ vg/eye, $40 \times 10^{11}$ vg/eye, $50 \times 10^{11}$ vg/eye or the like.

In another aspect, the present disclosure provides a method for improving a visual cognitive behavioral function, the method including administering a therapeutically effective amount of the nucleic acid, polypeptide, nucleic acid construct, gene-introducing composition, cell or pharmaceutical composition of the present disclosure to a subject.

In still another aspect, the present disclosure provides a method for enhancing a visual function, the method including administering a therapeutically effective amount of the nucleic acid, polypeptide, nucleic acid construct, gene-introducing composition, cell or pharmaceutical composition of the present disclosure to a subject.

In a particular aspect, the present disclosure provides a method for improving an object recognition function, the method including administering a therapeutically effective amount of the nucleic acid, polypeptide, nucleic acid construct, gene-introducing composition, cell or pharmaceutical composition of the present disclosure to a subject.

In one aspect, the present disclosure provides use of the nucleic acid, polypeptide, nucleic acid construct, gene-introducing composition, cell or pharmaceutical composition of the present disclosure, in the manufacture of a pharmaceutical for treating, preventing or suppressing the progress of an eye disease, disorder or symptom of a subject.

In another aspect, the present disclosure provides use of the nucleic acid, polypeptide, nucleic acid construct, gene-introducing composition, cell or pharmaceutical composition of the present disclosure, in the manufacture of a pharmaceutical for improving a visual cognitive behavioral function.

In still another aspect, the present disclosure provides use of the nucleic acid, polypeptide, nucleic acid construct, gene-introducing composition, cell or pharmaceutical composition of the present disclosure, in the manufacture of a pharmaceutical for enhancing a visual function.

In a particular aspect, the present disclosure provides use of the nucleic acid, polypeptide, nucleic acid construct, gene-introducing composition, cell or pharmaceutical composition of the present disclosure, in the manufacture of a pharmaceutical for improving an object recognition function.

(General Technology)

The molecular biology approaches, biochemical approaches, and microbiological approaches as used herein are those well known and commonly practiced in the art, which are described in documents such as Current Protocols in Molecular Biology and Molecular Cloning: A Laboratory Manual (Fourth Edition, the relevant parts (which may be all the parts) of which are incorporated herein by reference.

As used herein, the term, "or", is used when "at least one or more" of the matters listed in the sentences can be employed. When explicitly described herein as "within the range of two of the values", the range also includes the two values themselves.

Reference literatures such as scientific literatures, patents, and patent applications cited herein are incorporated herein by reference to the same extent that the entirety of each document is specifically described.

As described above, the present disclosure has been explained while showing preferred embodiments to facilitate understanding. The present disclosure is explained hereinafter based on Examples. The above explanation and the following Examples are not provided to limit the present disclosure, but for the sole purpose of exemplification. Thus, the scope of the present disclosure is not limited to the embodiments or the Examples specifically described herein and is limited only by the scope of claims.

EXAMPLES

Examples will be described hereinafter. The handling of animals used in the following examples was carried out, if necessary, based on the Declaration of Helsinki, in compliance with the standards and other relevant ethical standards and guidelines as stipulated by Keio University and others. As for reagents, while those specifically described in Examples were used, these reagents can be substituted by equivalent products of other manufacturers (such as, Sigma-Aldrich, Wako Pure Chemical, Nacalai, R & D Systems and USCN Life Science Inc.).

(Example 1: Vector Preparation)

The DNA encoding the chimeric protein (GR/BvRh) was produced as follows. The sequence corresponding to the 137th to 145th amino acids from the N-terminal, which corresponds to the second loop on the cytoplasm side of Gloeobacter *violaceus* Rhodopsin (GR) (SEQ ID NO: 14), was substituted by the sequence corresponding to the 137th to 145th amino acids of bovine rhodopsin (BvRh) (SEQ ID NO: 12), and the sequence corresponding to 198th to 206th amino acids from the N-terminal, which corresponds to the third loop on the cytoplasm side of GR, was substituted by the sequence corresponding to the 225th to 252nd amino acids of the bovine rhodopsin. Furthermore, DNA encoding a chimeric protein, in which glutamic acid, or the 132nd amino acid of GR, was substituted by glutamine, was inserted into the pCDNA3.1 vector. Alternatively, nucleic acids having the base sequence set forth in SEQ ID NO: 23 were generated and inserted, as the DNA encoding the chimeric protein, into the pCDNA3.1 vector HindIII/XbaI site. The base sequence set forth in SEQ ID NO: 23 was generated as follows: the sequence corresponding to the 137th to 145th amino acids from the N-terminal, which corresponds to the second loop on the cytoplasm side of Gloeobacter *violaceus* Rhodopsin (GR) (SEQ ID NO: 14), was substituted by the base sequence set forth in SEQ ID NO: 18 corresponding to the second loop of bovine rhodopsin (BvRh) (SEQ ID NO: 12) (the encoding of the amino acid sequence set forth in SEQ ID NO: 19), and the sequence corresponding to 198th to 206th amino acids from the N-terminal, which corresponds to the third loop on the cytoplasm side of GR, was substituted by the base sequence set forth in SEQ ID NO: 20 corresponding to the third loop of the bovine rhodopsin (the encoding of the amino acid sequence set forth in SEQ ID NO: 22), thereby producing the base sequence. In addition, the base sequence set forth in SEQ ID NO: 3 was prepared by changing part of the base without changing the amino acids to be encoded. Specifically, the preparation was performed by mutating the nucleic acids encoding the amino acids 6, 9-13, 15, 16, 18-22, 27-29, 31-36, 39, 40, 43, 45, 48, 50, 51, 53-55, 58, 59, 61, 65-73, 75-84, 86, 88, 89, 93, 97, 98, 100, 101, 104, 106-108, 110, 112, 114, 115, 122, 123, 125, 128, 131, 133, 139, 143, 145, 146, 155, 157, 162, 165, 167, 169-171, 174, 176, 179, 182, 183, 186-189, 193-198, 204, 205, 207, 209, 212, 215, 216, 218-220, 224, 225, 227, 228, 230, 231, 233-235, 238, 240, 242, 243, 246, 247, 249, 251, 253-255, 257-259, 261-264, 266-270, 272, 273, 275, 276, 279, 281-287, 289-291, 296-299, 302-305, 307-316, 318, 319, and 321-330, without changing the amino acids to be encoded. The production of the mutant was conducted using the quick change method. Note that the sequence portion adopted for bovine rhodopsin completely matches the amino acid sequence of human rhodopsin, and thus, the sequence portion may be referred to as human rhodopsin without any problem.

The EGFP or GR/BvRh gene was subcloned into the AAV2 shuttle plasmid, and AAV2-CAGGS-EGFP-WPRE-pA (vector for the expression of EGFP) and AAV2-CAGGS-GR/BvRh-WPRE-pA (vector for the expression of chimeric protein) were produced as virus expression constructs. Viral vector packaging was performed by transfecting HEK293 cells with three types of plasmids, vector plasmid, AAV vector plasmid and adenovirus helper plasmid; and the cesium chloride method was used to purify the viral vector. Note that, with regard to the vector, the "ITR" is an abbreviation for "Inverted Terminal Repeat". The "CAGGS" is a sequence of regions of the CAG promoter. The "WPRE" is an abbreviation for "woodchuck hepatitis virus post-transcriptional regulatory element". The "pA" means a peptide tag. The "EGFP" is an abbreviation for "enhanced green fluorescent protein".

FIG. 1 shows the configurations of a nucleic acid construct encoding chimeric rhodopsin (hereinafter, first nucleic acid construct) and nucleic acid construct encoding chimeric rhodopsin to which a signal sequence has been added (hereinafter, the nucleic acid construct of the present disclosure). ER2 shown in FIG. 1 is a type of the endoplasmic reticulum export signals.

(Example 2: Multi-Electrode Array (Multiple Electrode Array: MEA) Test Using the Nucleic Acid Construct of the Present Disclosure)

The effect of the nucleic acid construct of the present disclosure on the optical response was measured. The descriptions thereof will be provided hereinafter.

Materials and Methods (Animals)

A model of retinitis pigmentosa, rd1 mouse (Pde6b$^{rd1/rd1}$), was used. A C3H/HeJ Jcl mouse having the above mutation was purchased from Japan Claire Co., Ltd.

(Multi-Electrode Array)

Herein, the multi-electrode array is schematically an approach for investigating the type of activated cells, the timing and size of the activity, and the like by placing nerve cells on an element with a large number of electrodes, recording the electrical response of the nerve cells from outside the cells, and analyzing the waveform of the electrical response.

(Vector Administration)

Blind rd1 mice at the age of 10 weeks or older were administered 1 μl of AAV DJ-CAGGS-Chimeric rhodopsin (GR/BvRh)-WPRE-pA vector (the first nucleic acid construct), or AAV DJ-CAGGS-Chimeric rhodopsin-sm (GR/BvRh-sm)-WPRE-pA (the nucleic acid construct of the present disclosure) to which a signal sequence had been added, at a concentration of 1.0×10⁹ vg/μl by intravitreal injection.

(Measurements)

The optical response of the mice was measured at or after the 4th week after the injection, at which gene expression peaked. In the multi-electrode array (multi-electrode array: MEA) tests, the optical response of retinal ganglion cells was measured ex vivo by changing the light stimulation intensity of the white LED.

Results

Figure 2A:
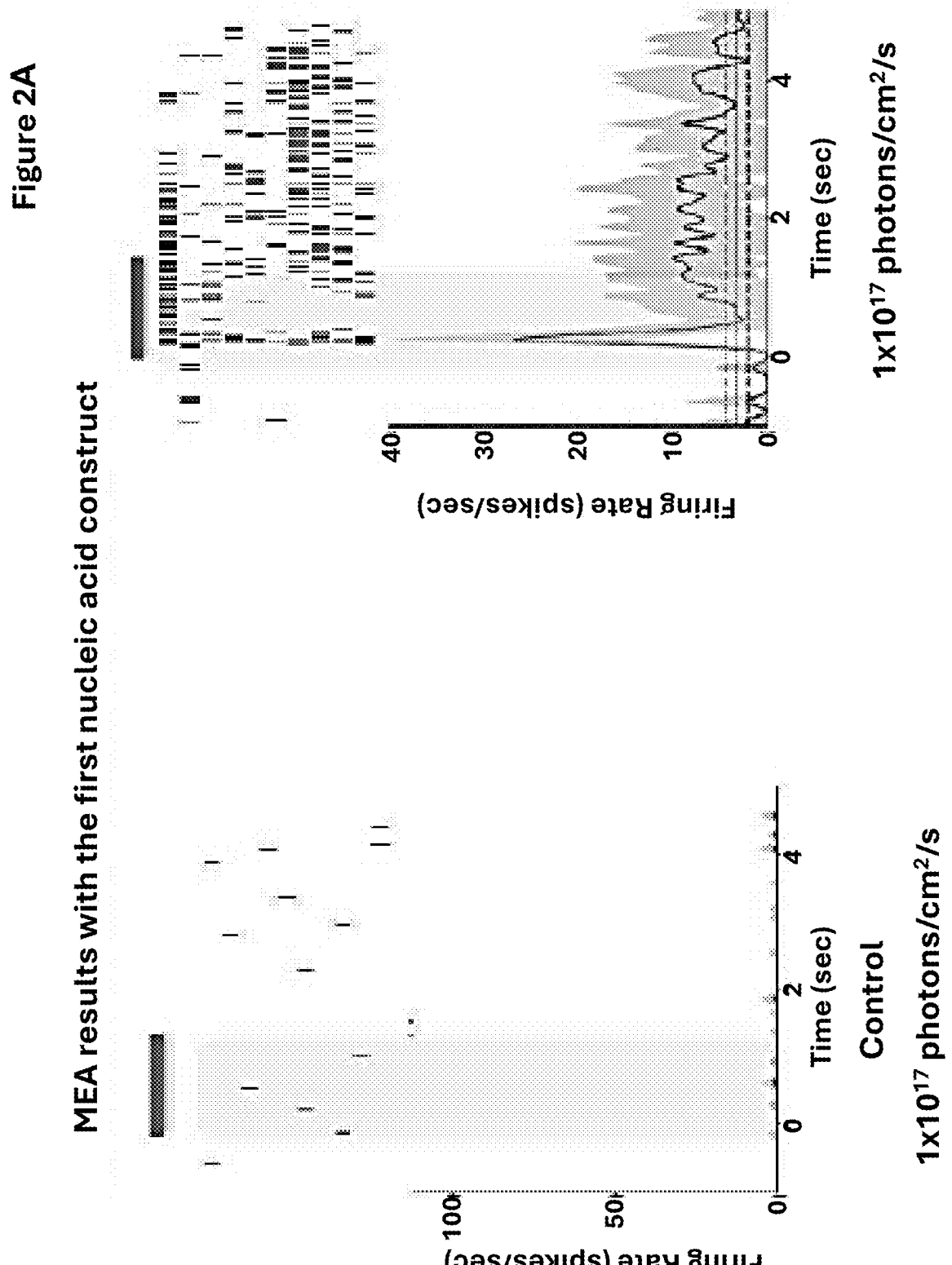
Figure 2B:
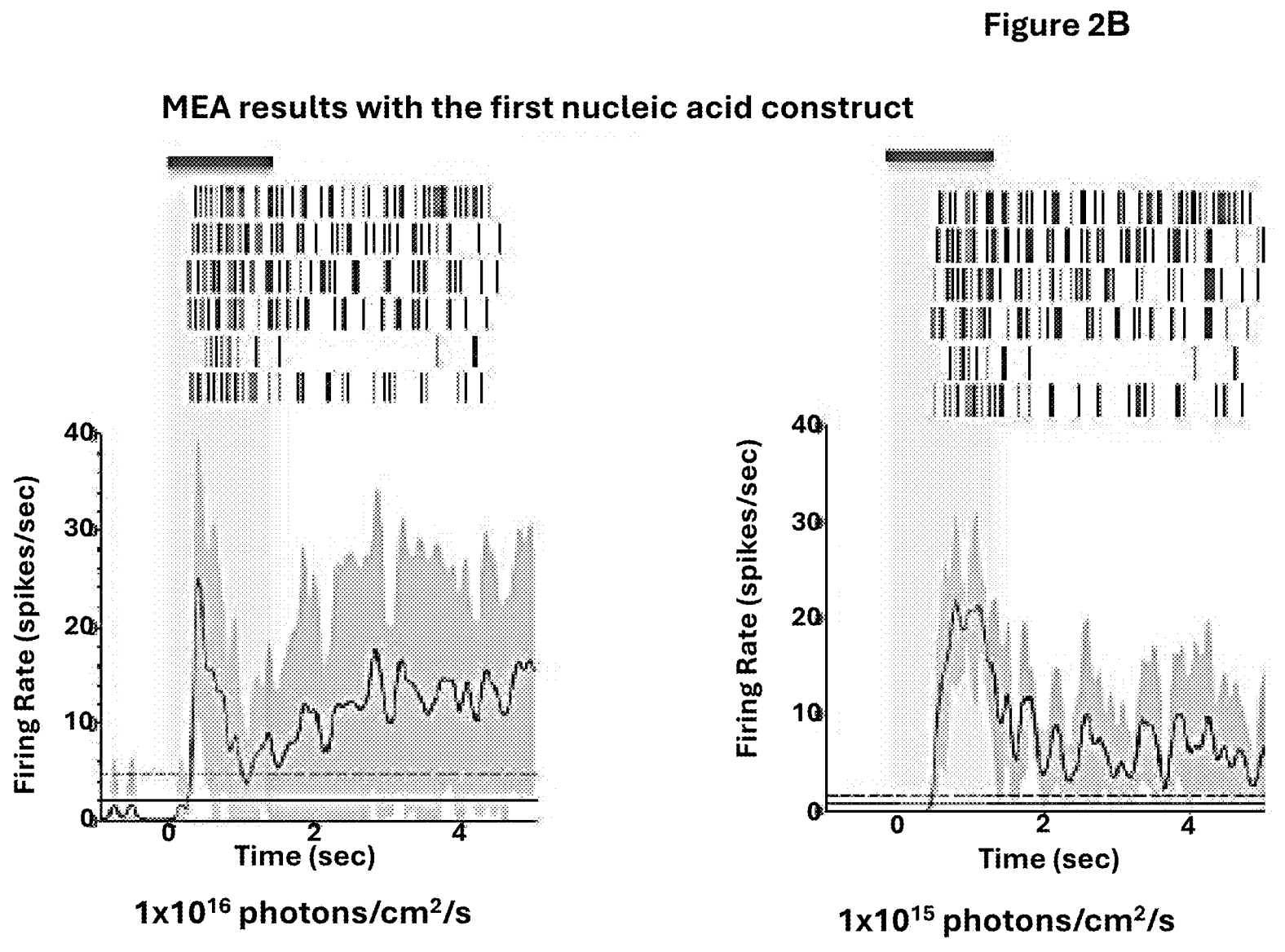
Figure 2C:
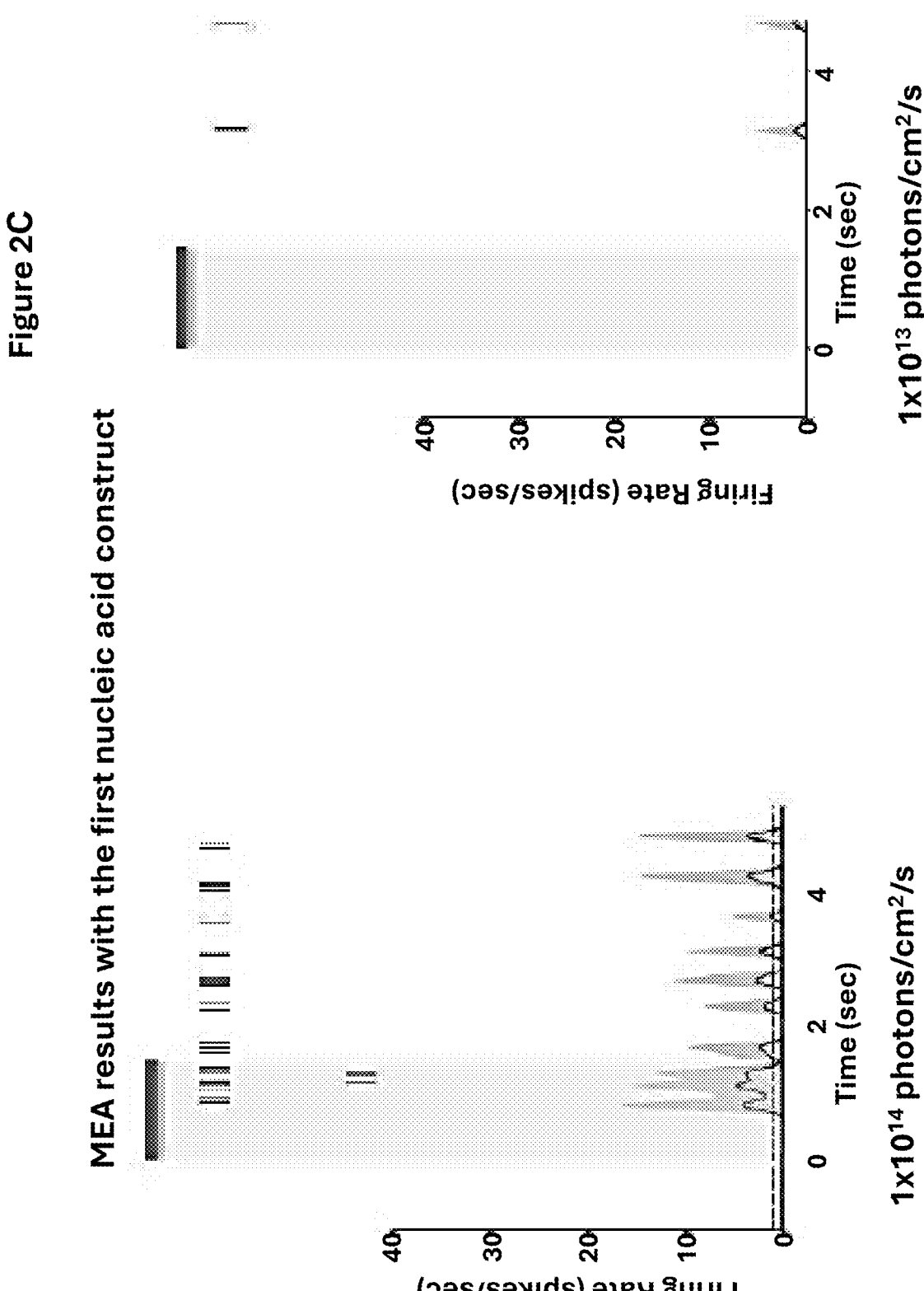
Figure 3A:
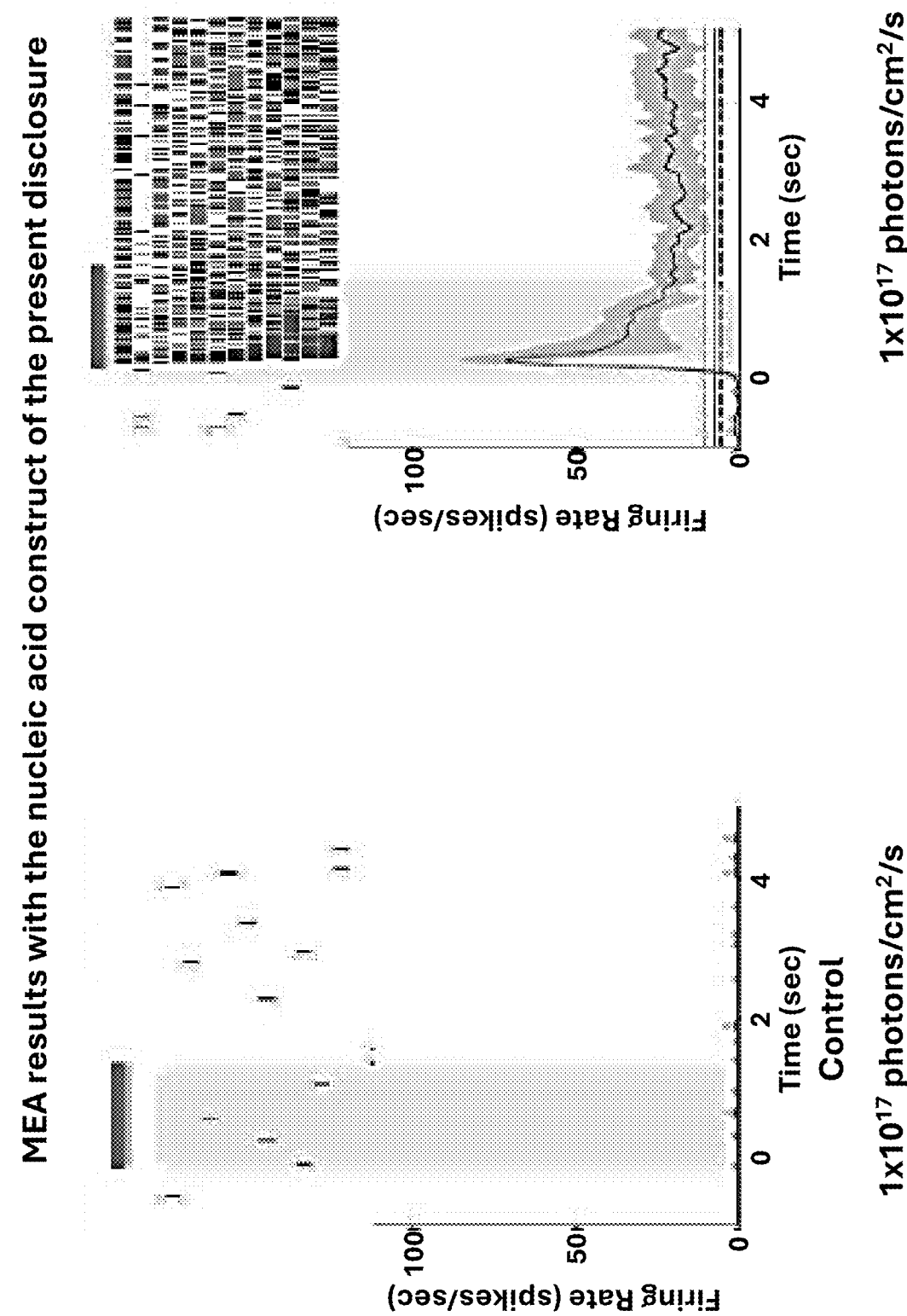
Figure 3B:
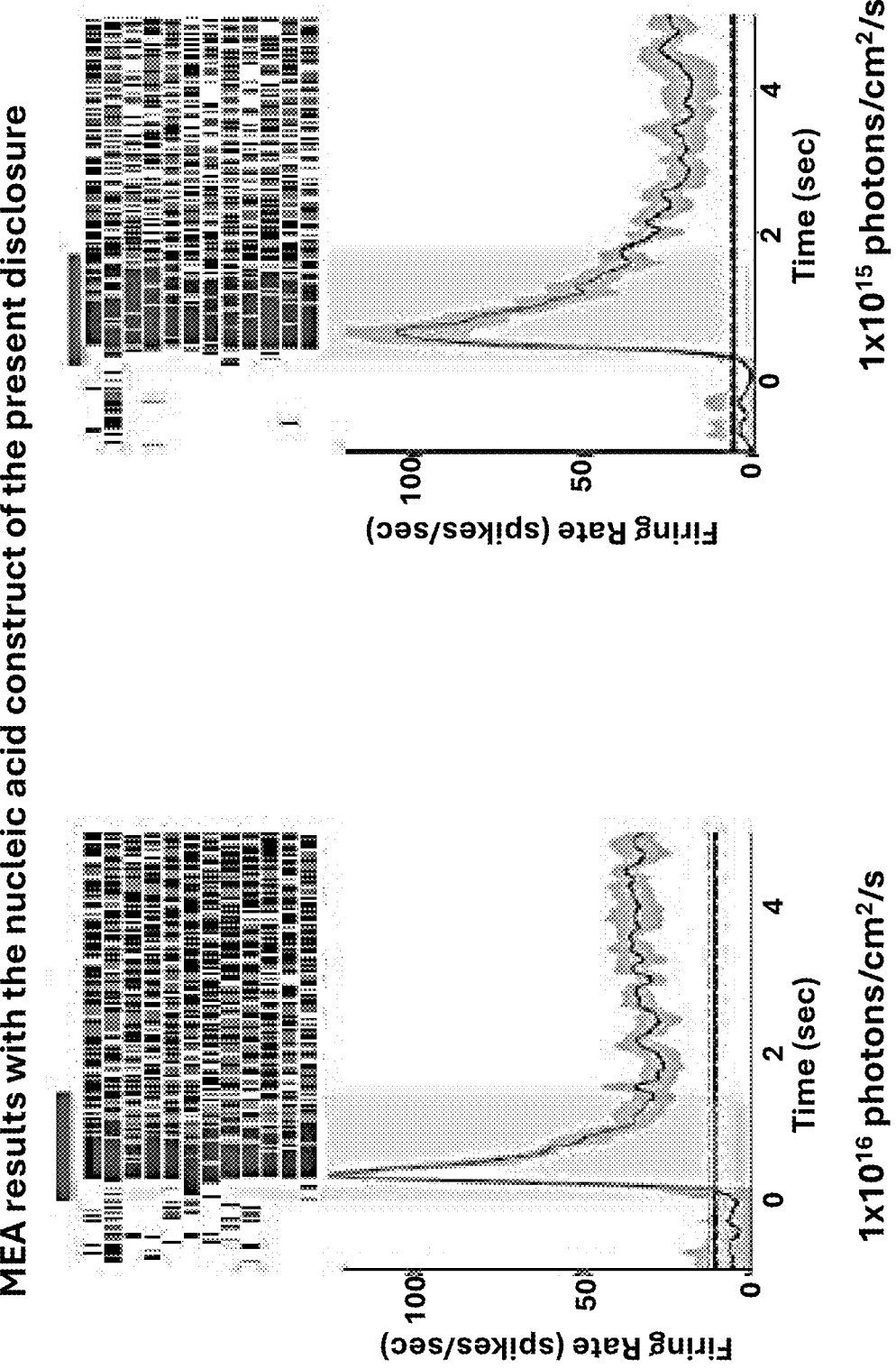
Figure 3C:
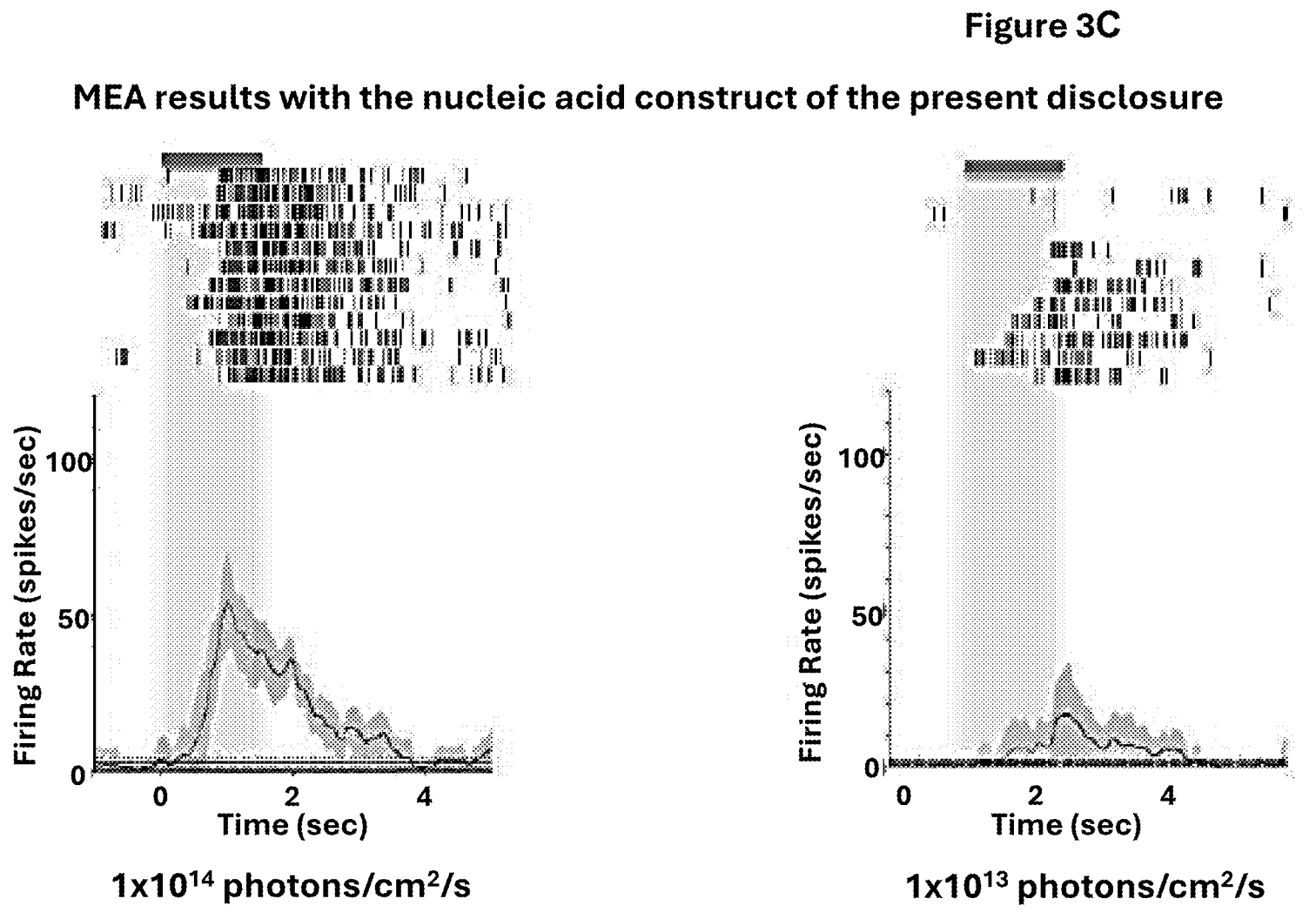
Figure 4:
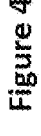
FIG. 4 is a diagram quantifying the results of FIGS. 2 and 3. In the stimulus intensity range of $1\times10^{14-16}$ photons/cm$^2$/s, the nucleic acid construct of the present disclosure has a significantly higher firing frequency.
Figure 5:
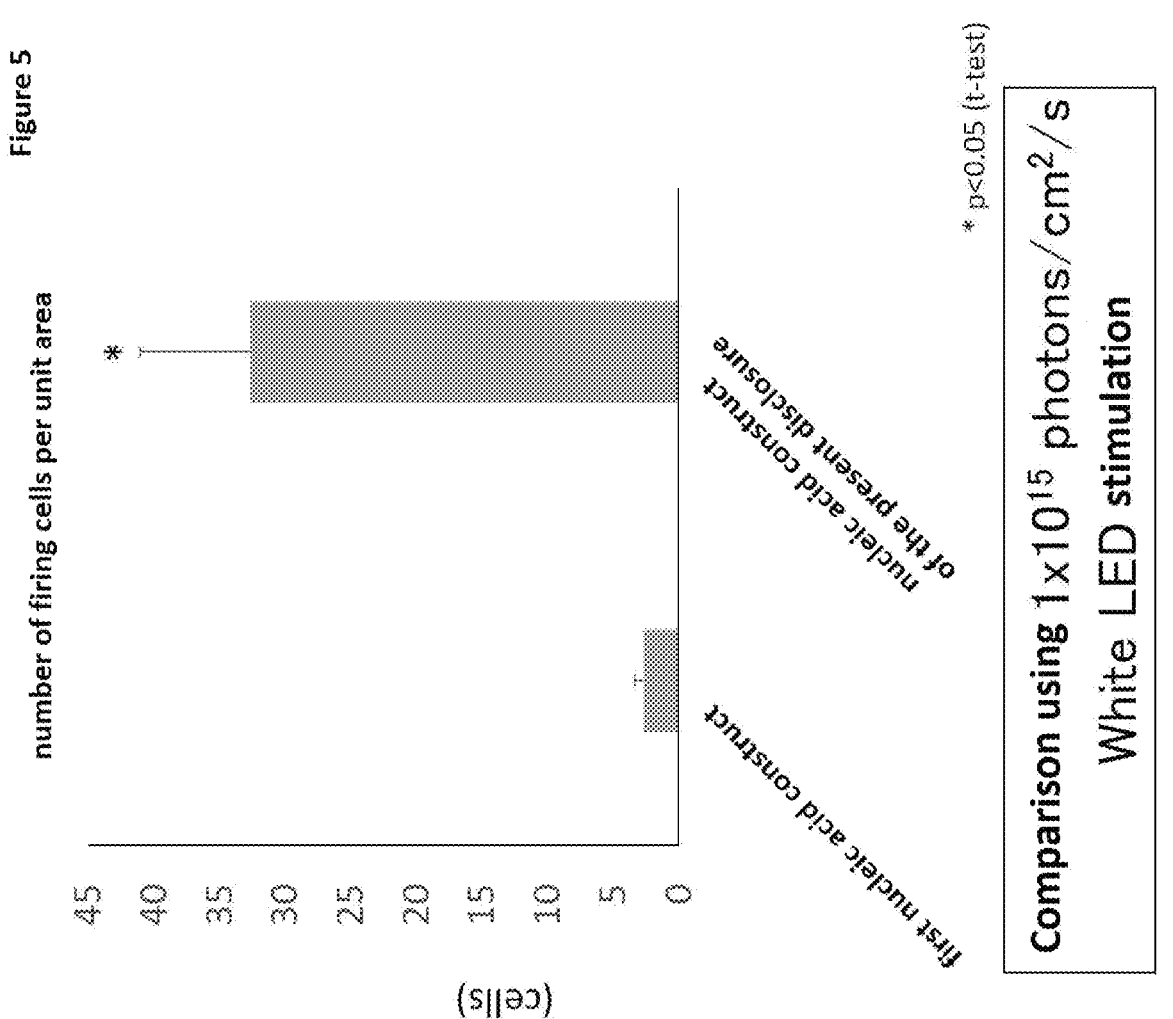
FIG. 5 is a diagram quantifying the results of FIGS. 2 and 3. At the stimulation intensity of $1\times10^{15}$ photons/cm$^2$/s, the nucleic acid construct of the present disclosure has a significantly higher number of firing cells per unit area.

The results of carrying out the multi-electrode array are shown with the light intensity of 1×10¹⁷ photons/cm²/s, 1×10¹⁶ photons/cm²/s, 1×10¹⁵ photons/cm²/s, 1×10¹⁴ photons/cm²/s and 1×10¹³ photons/cm²/s. The upper part of FIGS. 2 and 3 shows a raster plot display of firing of retinal ganglion cells, and each graph shows a histogram showing the firing frequency per second on the vertical axis. The horizontal axis of the graph shows the time (seconds). The lower part of each graph shows the construct of the introduced chimeric protein and the light intensity. Note that: the light intensity of 1×10¹³ photons/cm²/s corresponds to the light intensity of the night road with street lights and a corridor at home at night; the light intensity of 1×10¹⁴ photons/cm²/s corresponds to the light intensity in a home room; the light intensity of $1 \times 10^{15}$ photons/cm$^2$/s corresponds to the light intensity in a store; the light intensity of $1 \times 10^{16}$ photons/cm$^2$/s corresponds to the light intensity of outdoors in cloudy weather; and the light intensity of $1 \times 10^{17}$ photons/cm$^2$/s corresponds to the light intensity of outdoors in fine weather. The first nucleic acid construct obtained a response only at a light intensity of up to $1 \times 10^{14}$ photons/cm$^2$/s (FIG. 2), whereas the nucleic acid construct of the present disclosure obtained a response up to a light intensity of $1 \times 10^{13}$ photons/cm$^2$/s (FIG. 3). When the first nucleic acid construct was expressed in mice model of retinitis pigmentosa, electrical signals were emitted more frequently than negative controls up to a light intensity of $1 \times 10^{15}$ photons/cm$^2$/s, whereas when the nucleic acid construct of the present disclosure was expressed in mice model of retinitis pigmentosa, firing of ganglion cells was obtained with a higher frequency than the firing of negative controls up to a light intensity of $1 \times 10^{13}$ photons/cm$^2$/s. Furthermore, at each light intensity, the retinal ganglion cells when the nucleic acid construct of the present disclosure was introduced tended to fire more frequently than when the first nucleic acid construct was introduced. Especially at the light intensity of $1 \times 10^{15}$ photons/cm$^2$/s, the nucleic acid construct of the present disclosure was found to fire about three times more frequently than the first nucleic acid construct. In addition, at the light intensity of $1 \times 10^{13}$ photons/cm$^2$/s, the first nucleic acid construct showed little firing, while the nucleic acid construct of the present disclosure resulted in firing of retinal ganglion cells. Thus, expression of the chimeric protein from the nucleic acid construct of the present disclosure was demonstrated to result in unexpectedly significantly superior photosensitivity to the expression of the chimeric protein from the first nucleic acid construct. Furthermore, in the stimulus intensity range of $1 \times 10^{14}$-16 photons/cm$^2$/s, the nucleic acid construct of the present disclosure had a significantly higher firing frequency (FIG. 4). In addition, the result of carrying out the multi-electrode array per unit area in $1 \times 10^{15}$ photons/cm$^2$/s is shown. The number of firing cells per unit area was also significantly higher at the stimulation intensity of $1 \times 10^{15}$ photons/cm$^2$/s (FIG. 5). The vertical axis of the graph shows the number of retinal ganglion cells that fired around 2.6 mm$^2$. The retinal ganglion cells into which the first nucleic acid construct was introduced fired only about 2.7 cells against light having an intensity of $1 \times 10^{15}$ photons/cm$^2$/s, while about 33 cells, among the retinal ganglion cells into which the nucleic acid construct of the present disclosure was introduced, were fired. Thus, the nucleic acid construct of the present disclosure was demonstrated to provide unexpectedly superior photosensitivity, which is more than 12 times the photosensitivity of the first nucleic acid construct.

(Example 3: Wavelength Sensitivity Evaluation)

Figure 6:
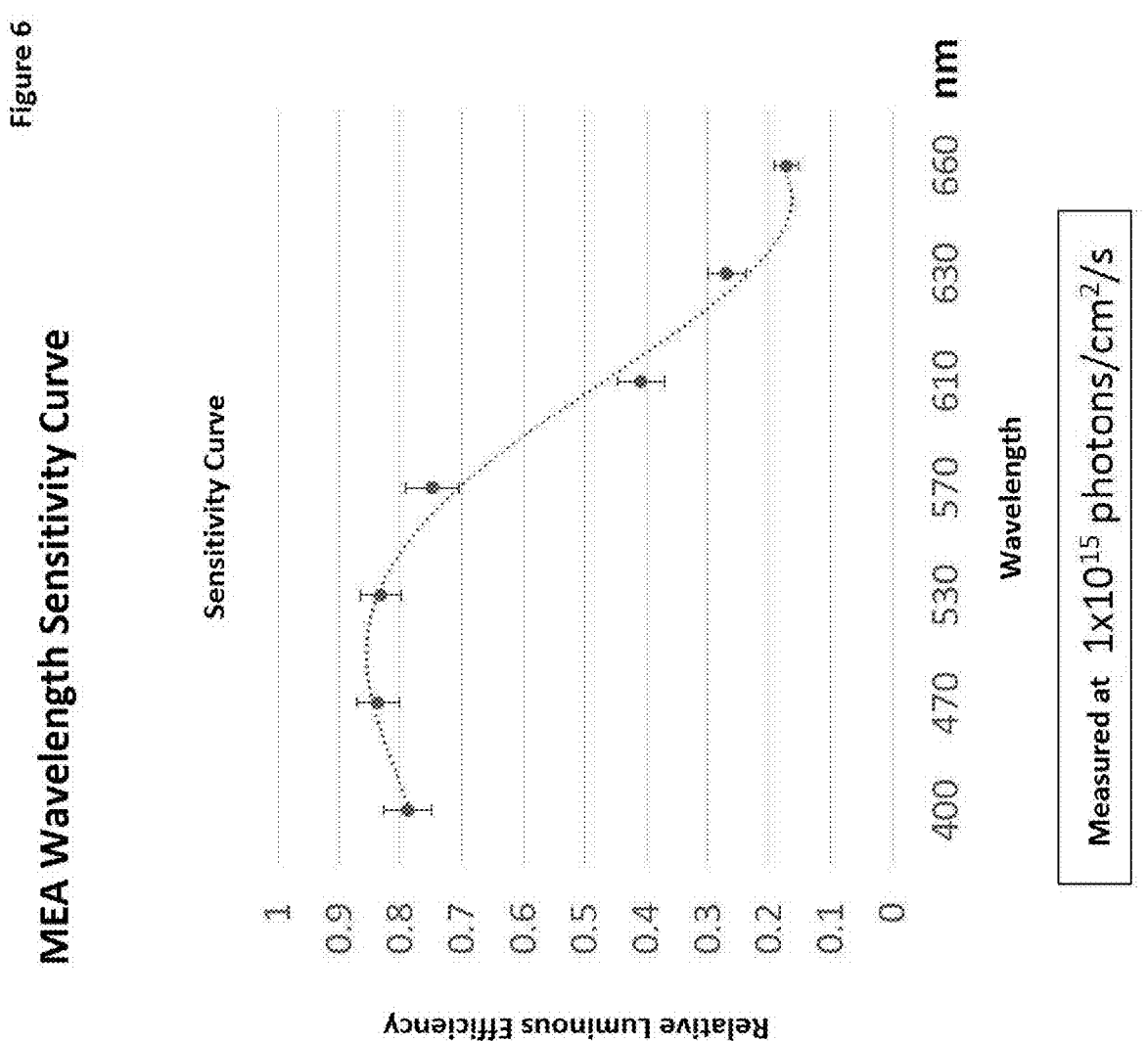
FIG. 6 is a diagram of evaluation of the wavelength sensitivity of mice injected with the nucleic acid construct of the present disclosure.

Relative luminous efficiency of each wavelength of male rd1 mice at the age of 11 weeks or older, seven weeks after the injection of the nucleic acid construct of the present disclosure, was measured. Light stimulation was performed with a wavelength-specific LED, and the peak firing frequency (Peak Firing Rate (spikes/sec)) of the 25 cells for which a reaction was obtained was measured at each wavelength. The most responsive value among all wavelengths was set as 1 and the ratio was set, and the average was measured. The measurement was performed with a light stimulation intensity of $1 \times 10^{14}$ photons/cm$^2$/s. As a result of the measurement, it was found that the mice injected with the nucleic acid construct of the present disclosure showed the expected wavelength sensitivity (FIG. 6). Since protein expression level is proportional to the number of firing cells, it was considered that the expression level of the chimeric rhodopsin protein was also increased to the same extent as the number of firing cells. It was considered that the sensitivity increased as the protein expression level increased.

(Example 4: Evaluation of Visual Evoked Potential)

The effect of the nucleic acid construct of the present disclosure on the visual evoked potential (VEP) was measured. The descriptions thereof will be provided hereinafter.

Materials and Methods (Animals)

A model of retinitis pigmentosa, rd1 mouse (Pde6b$^{rd1/rd1}$), was used. A C3H/HeJ Jcl mouse having the above mutation was purchased from Japan Claire Co., Ltd.

(Evaluation Method of Visual Evoked Potential)

Electrical signals emitted from the retina are transmitted to the primary visual cortex (V1 area) of the brain, which activates nerve cells in this area. Accordingly, in order to confirm the visual sense restoration effect at the central level, experiments were also conducted in which electrodes were implanted in the brain and neural activity was recorded extracellularly. Specifically, the prepared vector was injected intravitreally into retinitis pigmentosa model mice (rd1) and anesthetized. Then, the evoked potential for a flash stimulus of 0.1 cds/m$^2$ (this light intensity roughly corresponds to the light intensity of a night road with street lights or a corridor at home at night.) from a white LED installed 3 cm in front of the eyes was measured using a PuREC acquisition system (manufactured by Mayo Co., Ltd.). A flash stimulus of 0.1 cds/m$^2$ was measured.

(Vector Administration)

Blind rd1 mice at the age of 10 weeks or older were administered 1 µl of the first nucleic acid construct or the nucleic acid construct of the present disclosure, at a concentration of $1.0 \times 10^9$ vg/µl by intravitreal injection. The control group was administered the same amount of AAV DJ-CAGGS-EGFP-WPRE-pA vector.

Measurements

The VEP was measured at or after the 4th week after the injection, at which gene expression peaked. One week before the measurement, the mice were sedated by administration of three types of mixed anesthesia a (midazolam, medetomidine, and butorphanol tartrate were administered at 4 mg/kg, 0.75 mg/kg and 5 mg/kg body weight, respectively), and measurement electrodes were placed in the skull near the visual cortex (1.5 mm forward and 1.5 mm lateral to the lambda suture). After sedating the mice again with the three-types anesthesia, the evoked potential for a flash stimulus of 0.1 cds/m$^2$ was measured from a white LED installed 3 cm in front of the eyes. As the measuring device, PuREC acquisition system (Mayo, Inazawa, Japan) was used.

Results

Figure 7:
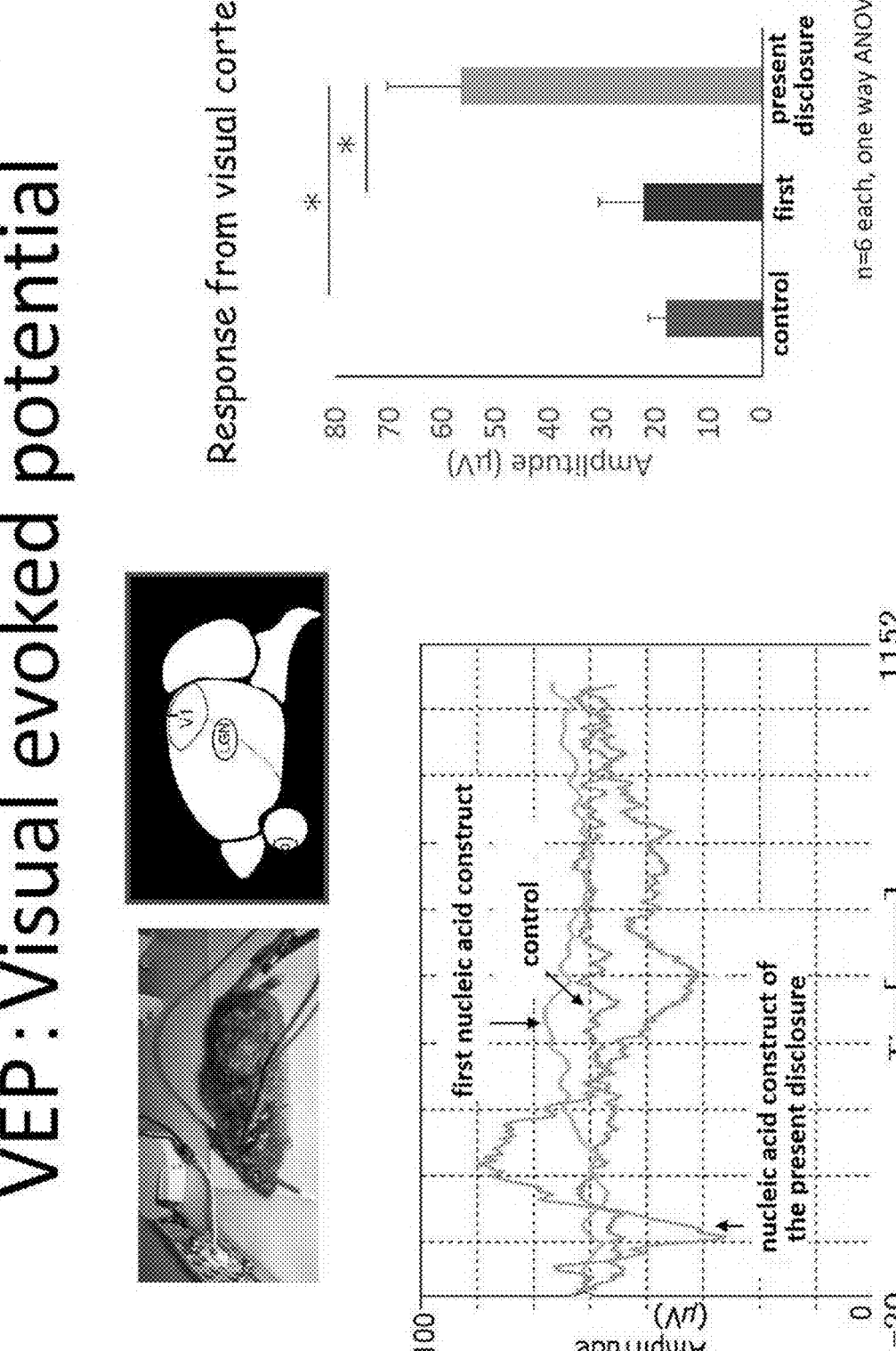
FIG. 7 is a diagram showing the results of a total evaluation of visual evoked potentials of a mouse injected with the first nucleic acid construct and a mouse injected with the nucleic acid construct of the present disclosure.

In FIG. 7, the vertical axis shows amplitude (µV) of the visual evoked potential obtained from the visual cortex by light stimulation. The lower part of the graph shows the construct of the introduced chimeric protein. A significant increase in amplitude was observed in the mice treated with the nucleic acid construct of the present disclosure (56.4±14.0 µV) with respect to the control (17.86±3.37 µV) and the mice treated with the first nucleic acid construct (22.13±8.38 µV). Treatment with the improved construct also showed a visually significant restoration effect at the central level (FIG. 7). Thus, the expression of the chimeric protein from the nucleic acid construct of the present disclosure was demonstrated to result in significantly better photosensitivity than the expression of the chimeric protein from the first nucleic acid construct.

(Example 5: Evaluation of Light-Dark Recognition Function)

The effect of the nucleic acid construct of the present disclosure on the light-dark recognition function was measured. The descriptions thereof will be provided hereinafter.

Materials and Methods (Animals)

A model of retinitis pigmentosa, rd1 mouse (Pde6b$^{rd1/rd1}$), was used. A C3H/HeJ Jcl mouse having the above mutation was purchased from Japan Claire Co., Ltd.

(Vector Administration)

Blind rd1 mice at the age of 10 weeks or older were administered 1 µl of the first nucleic acid construct or the nucleic acid construct of the present disclosure, at a concentration of 1.0×10$^9$ vg/µl by intravitreal injection. The control group was administered the same amount of AAV DJ-CAGGS-EGFP-WPRE-pA vector.

Measurements

A light-dark transition test (LDT) was conducted at or after the 4th week after the injection, at which gene expression peaked, to evaluate the light-dark recognition function. Mice were placed in a light-dark box (an acrylic case with the width: 415 mm, height: 300 mm, and depth: 250 mm, which is divided into two by a partition, one half of which receives 20 lux of light and the other half of which is a dark room, and the two are connected by a 5×5 mm window) and a video of their 10-minute action was taken. The ratio of staying time in the bright and dark halves was measured and compared.

Results

Healthy mice avoided the bright spot, so that their time spent in the bright spot was shorter, while blind mice (controls) had a staying time ratio of about half, 0.5. Furthermore, it can be seen that the mice treated by injecting the nucleic acid construct of the present disclosure had a significantly shorter staying time than the mice treated by injecting the first nucleic acid construct.

(Example 6: Evaluation of Object Recognition Function)

The effect of the nucleic acid construct of the present disclosure on the object recognition function was measured. The descriptions thereof will be provided hereinafter.

Materials and Methods (Animals)

A model of retinitis pigmentosa, rd1 mouse (Pde6b$^{rd1/rd1}$), was used. A C3H/HeJ Jcl mouse having the above mutation was purchased from Japan Claire Co., Ltd.

(Evaluation Method of Object Recognition Function)

In order to evaluate the object recognition function, the prepared vector was injected intravitreally into retinitis pigmentosa model mice (rd1), and the difference in behavior depending on whether or not the video was played was observed. Tablet terminals were installed on both side of the space in which the mice were placed, where, at a brightness of 10 lux, one tablet terminal played a mouse video and the other tablet terminal played an empty mouse cage. The staying time was measured in the area where the video of the mouse was played and the area where the video of the empty mouse cage was played, respectively. The measurement target time was set to be fifteen minutes immediately after the central partition was removed.

(Vector Administration)

Figure 8:
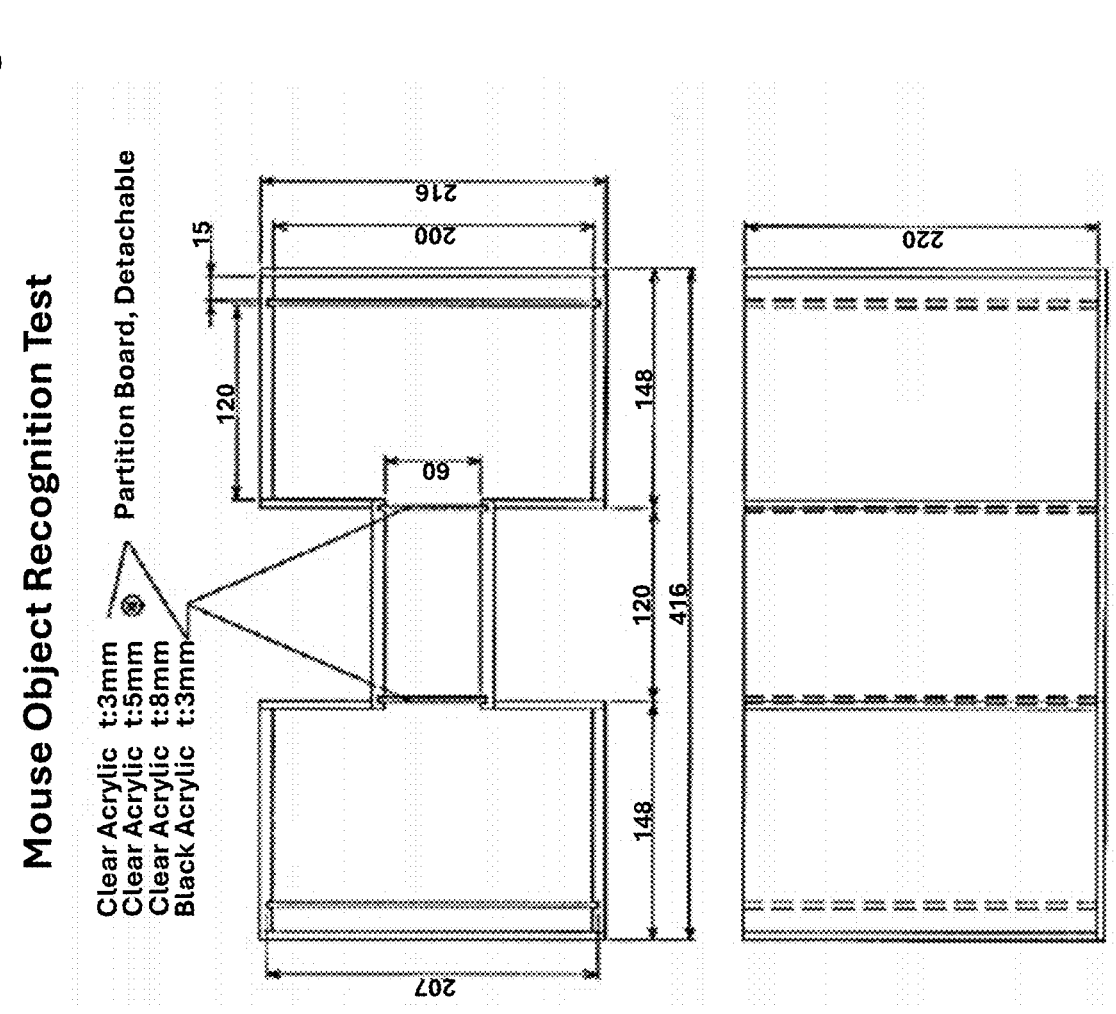
FIG. 8 is a diagram showing a space designed for an evaluation experiment of the object recognition function. The space was designed such that tablet terminals were installed on both sides of the space in which the mice were placed, where, at a brightness of 10 lux, one tablet terminal played a mouse video and the other tablet terminal played an empty mouse cage.

Blind rd1 mice at the age of 10 weeks or older were administered 1 µl of the nucleic acid construct of the present disclosure (AAV (2/6/DJ)-CAGGS-Chimeric rhodopsin (GR/BvRh)-WPRE-pA vector) at a concentration of 1.0×10$^9$ vg/µl by intravitreal injection. The blind control group was administered the same amount of AAV DJ-CAGGS-EGFP-WPRE-pA vector. Furthermore, a group to which AAV DJ-C1V1, a microbial rhodopsin with low sensitivity, was administered was also prepared as a control group. Tablet terminals were installed on both side of the space in which the mice were placed, where, at a brightness of 10 lux, one tablet terminal played a mouse video and the other tablet terminal played an empty mouse cage. The space designed for the experiment is shown in FIG. 8.

Measurements

The staying time was measured in the area where the video of the mouse was played and the area where the video of the empty mouse cage was played, respectively. The measurement target time was set to be fifteen minutes immediately after the central partition was removed.

Results

Figure 9:
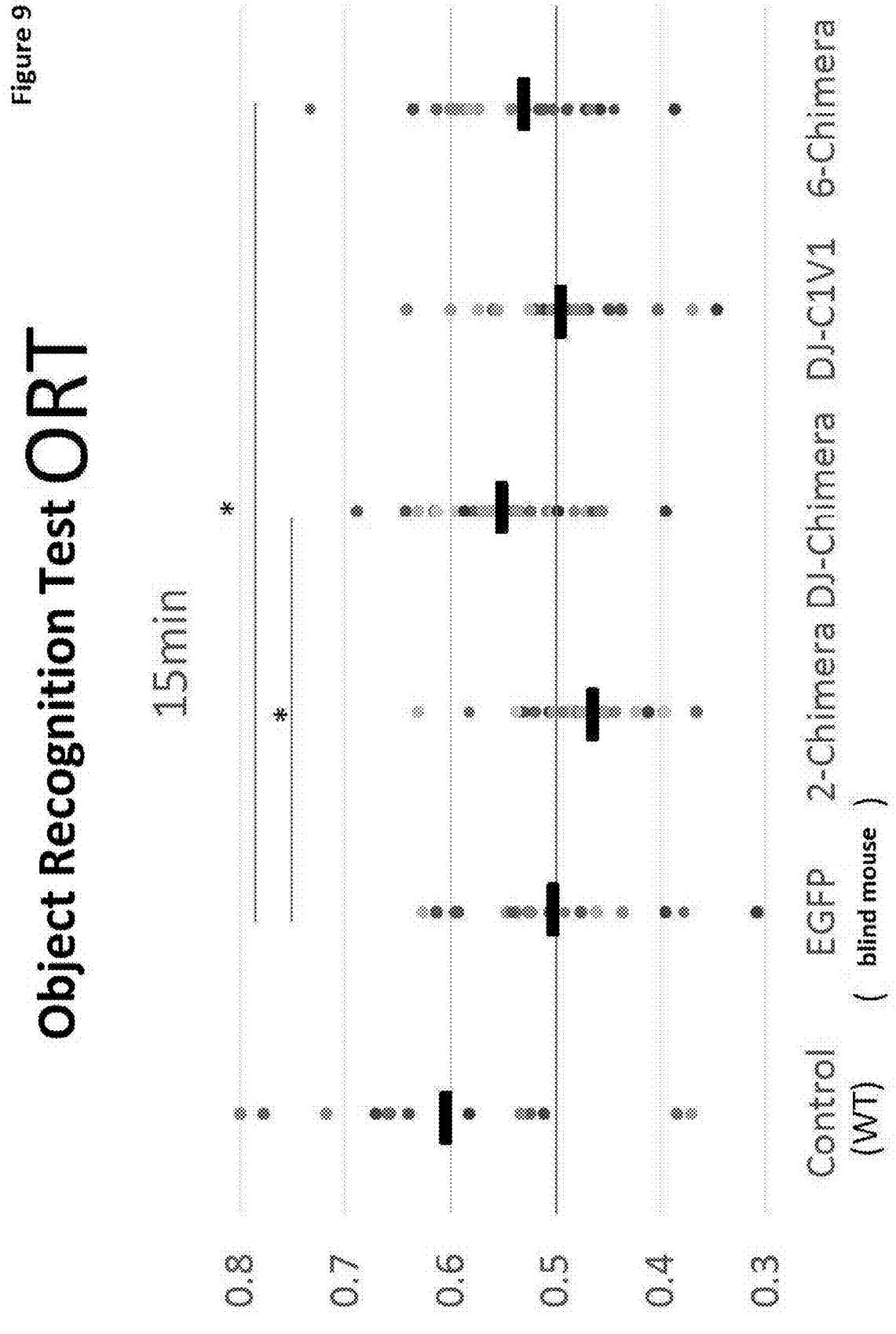
FIG. 9 is a diagram showing the evaluation test results of the object recognition function.

The object video side staying time ratio of the blind control group (EGFP) (time spent in the area where the mouse video is played/measurement time) was 0.495±0.019, while it was 0.555±0.06 for the DJ-type AAV chimera injection, and 0.538±0.015 for the type 6 AAV chimera injection, which were significantly higher (FIG. 9).

In the experimental result of FIG. 9, the vertical axis shows the object video side staying time ratio (time spent in the area where the mouse video is played/measurement time). The object video side staying time ratio of 0.5 indicates no mouse movement; and as the time ratio deviates from 0.5, it is interpreted as having an object recognition function that is directly linked to visual ability.

The object video side staying time ratio of the blind control group (EGFP) was 0.495±0.019, while it was 0.555±0.06 for the DJ-type AAV chimera injection, and 0.538±0.015 for the type 6 AAV chimera injection, where significantly high results were obtained. Note that the time staying in the cage in which the video was played tended to decrease, with the vector (2-Chimera) incorporated into AAV2; however, this result suggested the possibilities of the illusion of a repellent object such as a natural enemy due to the unusual appearance due to changes in the vector.

From the above results, it was demonstrated that the visual acuity is restored to a level at which an object can be recognized by expressing the construct of the present disclosure.

DISCUSSION

It is considered that the recovery of visual acuity at a level that can recognize an object was confirmed in the DJ type and the type 6. In type 2, the expression level in the target bipolar cell is low, it is considered that the object is not visible and that, although visual reproduction is occurring, the appearance is different because the expression pattern is different, and consequently, the mouse video was avoided. (Example 7: Preparation Method of Chimeric Protein of Ion Channeling Receptor Rhodopsin and G Protein-Coupled Receptor Rhodopsin (GtACR2/BvRh))

A chimeric protein of an ion channeling receptor rhodopsin and a G protein-coupled receptor rhodopsin (GtACR2/BvRh) was prepared using the same method as Example 1. A DNA encoding a chimeric protein in which the sequence corresponding to the amino acid corresponding to the second loop on the cytoplasmic side of Guillardia theta (GT) (SEQ ID NO: 15) was substituted by the amino acid corresponding sequence of bovine rhodopsin (BvRh) (SEQ ID NO: 12) and in which the sequence corresponding to the amino acid corresponding to the third loop on the cytoplasmic side of GT was substituted by the amino acid corresponding sequence of bovine rhodopsin, was inserted into the pCDNA3.1 vector. Alternatively, a nucleic acid having the base sequence set forth in SEQ ID NO: 6 was generated, which was inserted, as a DNA encoding the chimeric protein, into the pCDNA3.1 vector HindIII/XbaI site. A specific mutation was added to the prepared nucleic acid sequence to prepare the nucleic acid sequence set forth in SEQ ID NO: 7. Specifically, the base encoding the amino acids 1, 2, 4-9, 11-17, 21, 22, 27-30, 33, 34, 36-41, 43, 45, 48, 49, 51, 54, 56-58, 60, 63, 65, 68, 70, 71-75, 77-78, 81, 83, 84, 86, 89, 90, 92, 93, 95, 97-99, 102, 103, 111, 113, 114, 123, 125, 130, 131-137, 139, 142, 143, 146, 148-153, 156, 160, 161, 165, 167, 168, 170, 171, 174-176, 180, 182, 183, 187, 188, 190, 191, 196, 197, 199, 200, 202, 204, 208, 212-214, 217, 219, 226, 229, 232, 236-238, 240, 242, 243, 247, 248, 251, 252, 258, 263-265, 267, 269, 271, 272, 274, 276-280, 282-284, 289, 290, 291, 294, 297-299, 302, 304, 307 and 310 were changed without changing the amino acids to be encoded. (Example 8: Measurement of GPCR Activity of Nucleic Acid Construct of the Present Disclosure)

GPCR activity was measured by observing the fluorescence of GloSensor™ (Promega), which is used as an indicator of intracellular CAMP concentration.

Methods

Materials

ND7/23 cells were cultured, and a GR/BvRh-double-EQ-linker-Venus-ER2 vector, in which Venus was inserted into the nucleic acid construct of the present disclosure, and a pGloSensor™ (Promega) vector were gene-introduced. The same amount of pcDNA3.1 (empty vector) and pGloSensor (Promega) vector was gene-introduced into the control group. The gene-introduced cells were cultured and washed with PBS. Then, the cells were stripped with trypsin and EDTA and collected in a centrifuge tube. The cells were precipitated by centrifugation, and fresh DMEM culture medium was added and suspended. Based on the cell concentration, the cells were re-seeded at a concentration suitable for observation with a fluorescence microscope. (Measurement of G Protein-Coupled Receptor (GPCR) Activity)

An experimental system for analyzing signal transduction by light stimulation in cells was constructed. The details of the signal transduction pathway are as follows. Specifically, the photoreceptor cells express rhodopsin, which is a type of G protein-coupled receptor (GPCR), on the cell membrane, and rhodopsin binds to retinal. When the photoreceptor cells are exposed to light, the structure of retinal changes, which activates rhodopsin. The activated rhodopsin activates a G protein (Gt in the retina) distributed near the cell membrane, which activates CGMP phosphodiesterase. The CGMP phosphodiesterase is an enzyme that degrades intracellular CGMP, and thus, the activation thereof reduces intracellular CGMP concentration.

Here, the photoreceptor cells have a CGMP-dependent ion channel on the cell membrane thereof. When the intracellular cGMP concentration decreases, the ion permeability of this CGMP-dependent ion channel changes, and the membrane potential of the photoreceptor cells changes, which generates an electric signal. In this way, the photoreceptor cells convert optical signals into electrical signals.

Here, since it is difficult to measure the cGMP concentration in pathway mediated by the Gt-type G protein, the present disclosure measures the activation of the G protein by measuring changes in intracellular CAMP concentration caused by a pathway mediated by the same G protein family, Gi-type G protein. Since it is well known to those skilled in the art that Gt-type G protein and Gi-type G protein have crossing properties (for example, Xiang Li et al., "Fast noninvasive activation and inhibition of neural and network activity by vertebrate rhodopsin and green algae channelrhodopsin", PNAS, Dec. 6, 2005, Vol. 102, No. 49, pp. 17816-17821, and the document on page 17817 fourth paragraph of left column states, "vertebrate rhodopsin couples to the G protein transducin, the $\alpha$ subunit of which belongs to the Gi subfamily (15), thus raising the possibility that mammalian rhodopsins would couple to other Gi/o family members"). As such, it has been common practice to measure changes in intracellular CAMP concentration mediated by Gi-type G protein in order to measure the activation of Gt in the retina. To supplement, it is known that there are a plurality of types of G proteins and that the G protein present in photoreceptor cells is Gt (G$\alpha$t). Gt-type G proteins are present only in some cells such as photoreceptor cells, while Gs, Gi and Gq-type G proteins are present in general nerve cells. Among them, Gs-type G protein activates adenylate cyclase to increase the intracellular CAMP concentration, and in contrast, Gi-type G protein suppresses adenylate cyclase and reduces intracellular CAMP concentration.

In this experiment, changes in intracellular CAMP concentration mediated by Gi-type G protein were measured in order to analyze intracellular signal transduction pathways in response to light stimuli. The specific experimental approach is as follows.

The GR/BvRh-double-EQ-linker-Venus-ER2 vector and control vector were expressed in HEK293T cells using Lipofectamine® 2000 as instructed by the manufacturer. An experiment in which the vector was introduced into HEK293T cells was also performed in parallel. In these cultured cells, light stimulation was applied for one minute at a light intensity of $10^{16}$ photons/cm$^2$/s at 525 nm, and the intracellular CAMP concentration was measured using CAMP Gi kit (Cisbio), according to the manufacturer's instructions.

Measurements

The gene-introduced cells were transferred into a CO2-independent culture medium containing retinal (including 10% FBS, 2% eGloSensor™ stock solution). Changes in intracellular CAMP concentration were measured by recording changes in fluorescence intensity of GloSensor™. The measurements were performed according to the standard GloSensor™ assay protocol using a plate reader with a light irradiator. Forskolin (final concentration 3.5 µM) that activates adenylyl cyclase was administered to increase the intracellular CAMP concentration in advance. After the brightness of GloSensor™ was confirmed to reach a steady state, light having a wavelength of 510 nm (about 0.27 mW) was irradiated for 2 minutes from about 35 minutes after administration of Forskolin. Further, light having a wavelength of 464 nm (about 2.8 mW) was irradiated for 2 minutes from about 50 minutes after the administration of Forskolin. This experiment was performed twice, and the change in brightness of GloSensor™ in each experiment was graphed (FIG. 10).

Results

Figure 10A:
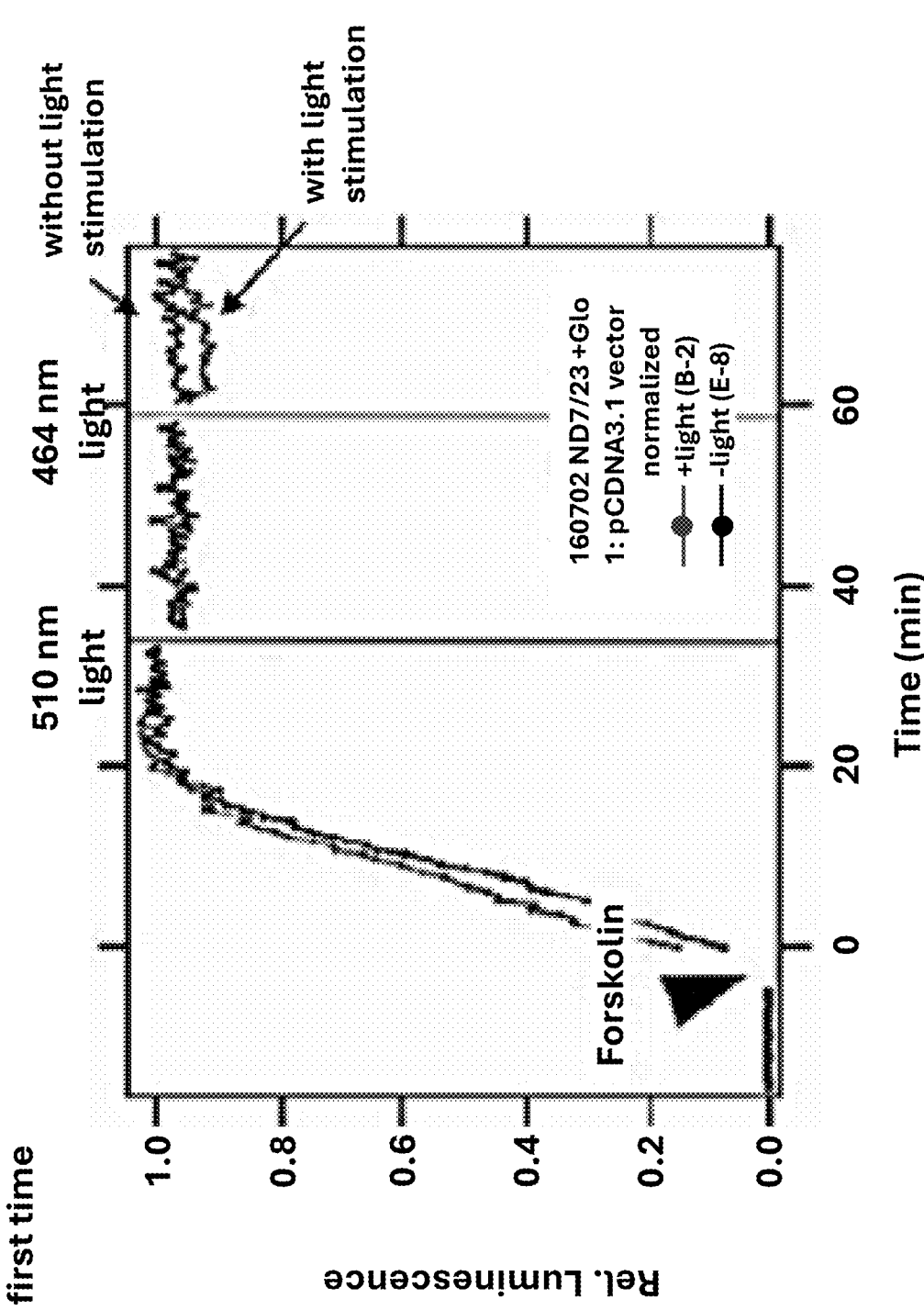
FIGS. 10A to 10D are diagrams of measuring the GPCR activity of the protein encoded by the nucleic acid construct of the present disclosure (FIGS. 10C and 10D) compared to a control vector (FIGS. 10A and 10B) using GloSensor™.
Figure 10:
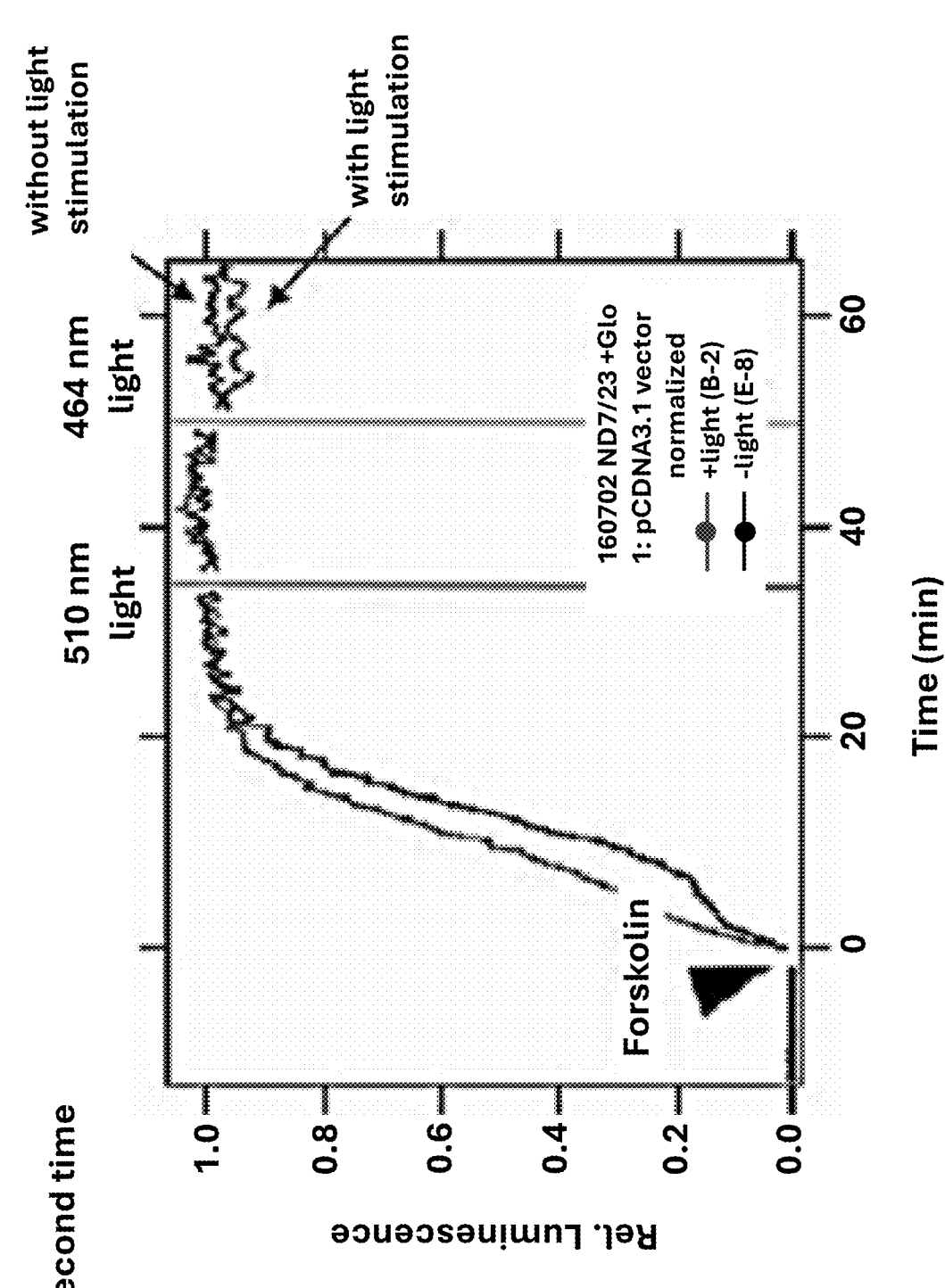
Figure 10C:
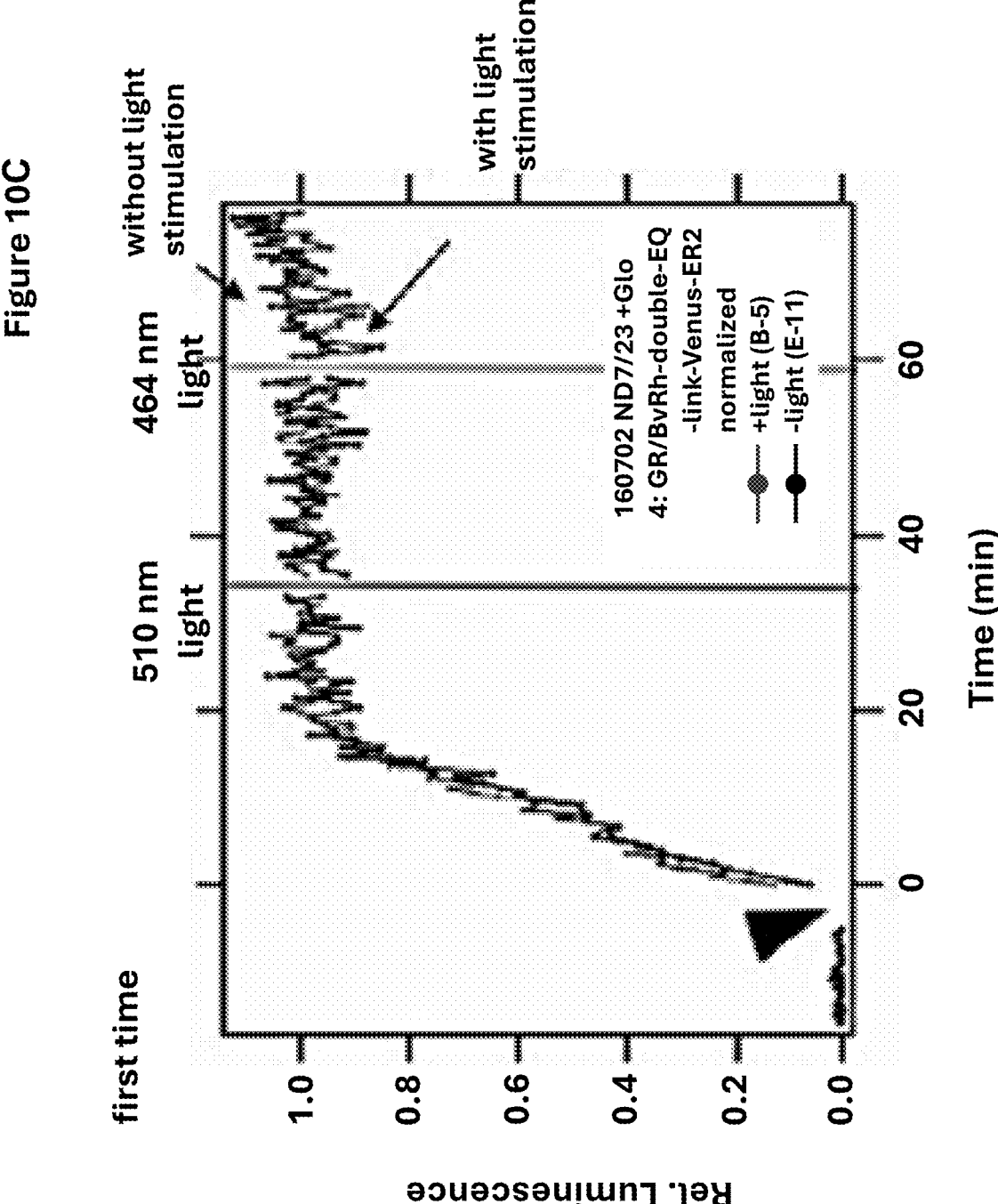
Figure 10:
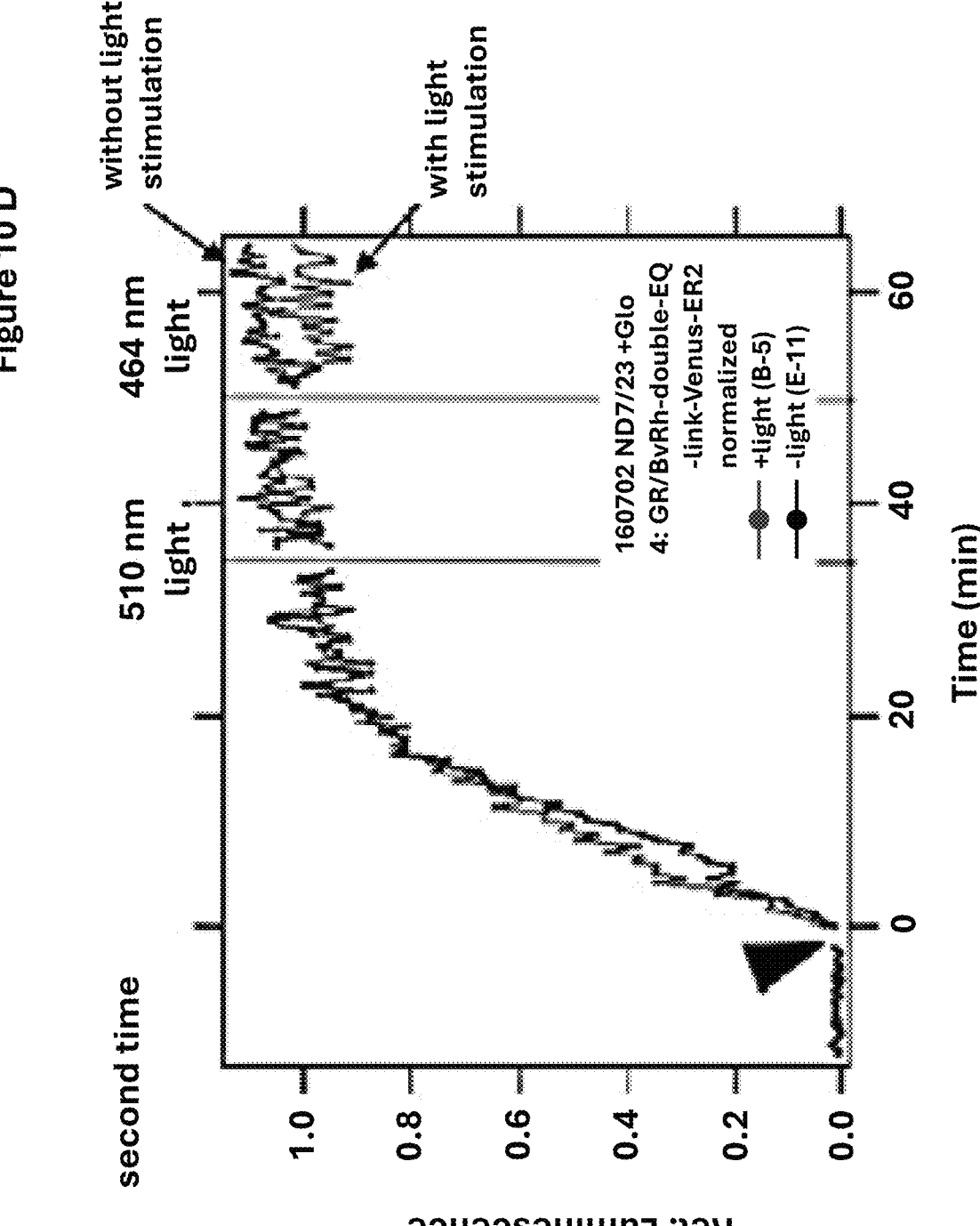

In the control group, no difference in brightness was observed between with and without light irradiation (FIG. 10A). On the other hand, in the group to which the GR/BvRh-double-EQ-linker-Venus-ER2 vector was administered, a decrease in the brightness of GloSensor™ was observed after irradiation with light of 464 nm as compared with the case without irradiation with light (FIG. 10B). The brightness of GloSensor™ is known to correspond to a decrease in intracellular CAMP concentration, which indicates that the intracellular CAMP concentration decreased by light stimulation in the group to which the GR/BvRh-double-EQ-linker-Venus-ER2 vector was administered. Thus, it can be seen that the GR/BvRh-double-EQ-linker-Venus-ER2 in which Venus was inserted into the nucleic acid construct of the present disclosure has GPCR activity and can lead to treatment, prevention or suppression of the progress of diseases, disorders or symptoms of the retina, improvement in the visual cognitive behavioral function, and enhancement of the visual function.

Figure 13:
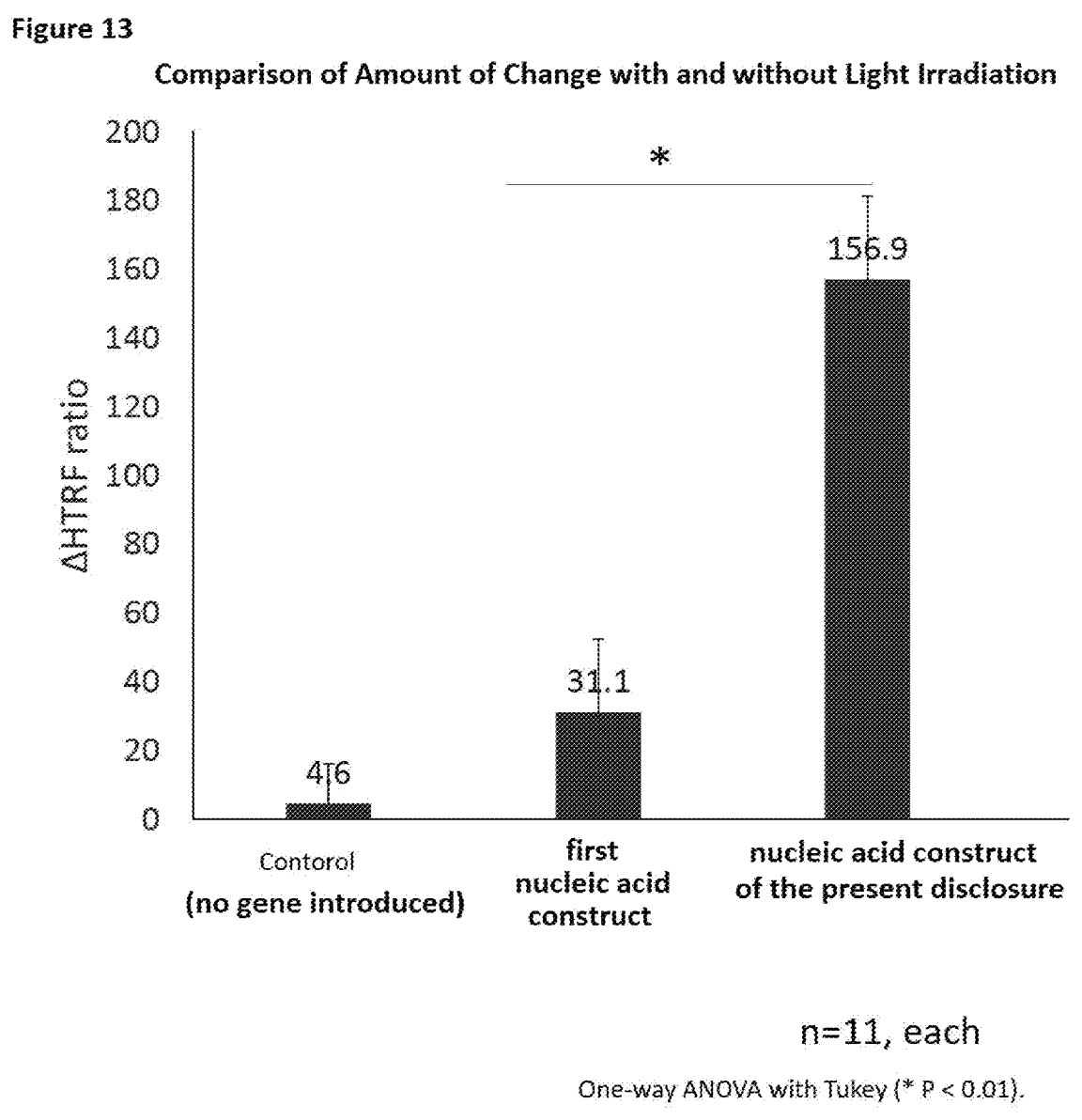

FIG. 13 shows experimental data of inducible expression of each gene in HEK293T cells using the lipofection method and the measurement of the change in CAMP concentration with and without light stimulation. The vertical axis shows the ΔHTRF ratio, and the horizontal axis shows the results for each gene. HTRF (Homogeneous Time-Resolved Fluorescence) is the ratio of exogenous reference CAMP to endogenous CAMP measured using a fluorescent antibody of CAMP (HTRF ratio). As the endogenous CAMP increases, the HTRF ratio decreases, which is inversely proportional to the CAMP concentration. The ΔHTRF ratio is the difference in HTRF ratio with and without light irradiation, and the larger this is, the more CAMP decreases by light stimulation, that is, the G protein (Gi) is indicated as being activated.

In FIG. 13, as a result of conducting the experiment using eleven individuals, the expression of the chimeric protein with the first nucleic acid construct was 31.1±21.4, and the expression of the chimeric protein with the nucleic acid construct of the present disclosure was 156.9±24.2, against 4.6±11.5 of the negative control.

Accordingly, it was demonstrated that the expression of the nucleic acid construct of the present disclosure results in significantly better photosensitivity than the expression of the chimeric protein of the first nucleic acid construct.

(Example 9: Measurement of GPCR Activity of Nucleic Acid Construct Encoding the Chimeric Protein of Ion Channeling Receptor Rhodopsin and G Protein-Coupled Receptor Rhodopsin)

GPCR activity was measured by observing the fluorescence of GloSensor™ (Promega), which is used as an indicator of intracellular CAMP concentration.

Methods

Materials

ND7/23 cells were cultured, and the GtACR2tr/BvRh-double vector and the pGloSensor™ (Promega) vector were gene-introduced. The same amount of pcDNA3.1 (empty vector) and pGloSensor (Promega) vector was gene-introduced into the control group. The gene-introduced cells were cultured and washed with PBS. Then, the cells were stripped with trypsin and EDTA and collected in a centrifuge tube. The cells were precipitated by centrifugation, and fresh DMEM culture medium was added and suspended. Based on the cell concentration, the cells were re-seeded at a concentration suitable for observation with a fluorescence microscope.

Measurements

The gene-introduced cells were transferred into a CO2-independent culture medium containing retinal (including 10% FBS, 2% GloSensor™ stock solution). Changes in intracellular CAMP concentration were measured by recording changes in fluorescence intensity of GloSensor™. The measurements were performed according to the standard GloSensor™ assay protocol using a plate reader with a light irradiator. Forskolin (final concentration 3.5 µM) that activates adenylyl cyclase was administered to increase the intracellular CAMP concentration in advance. After the brightness of GloSensor™ was confirmed to reach a steady state, light having a wavelength of 510 nm (about 0.27 mW) was irradiated for 2 minutes from about 35 minutes after administration of Forskolin. Further, light having a wavelength of 464 nm (about 2.8 mW) was irradiated for 2 minutes from about 50 minutes after the administration of Forskolin. This experiment was performed twice, and the change in brightness of GloSensor™ in each experiment was graphed (FIG. 11).

Results

Figure 11A:
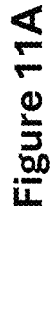
FIGS. 11A to 11D are diagrams of measuring the GPCR activity of a chimeric protein of an ion channeling receptor rhodopsin and a G protein-coupled receptor rhodopsin (FIGS. 11C and 11D) compared to a control vector (FIGS. 11A and 11B) using GloSensor™.
Figure 11B:
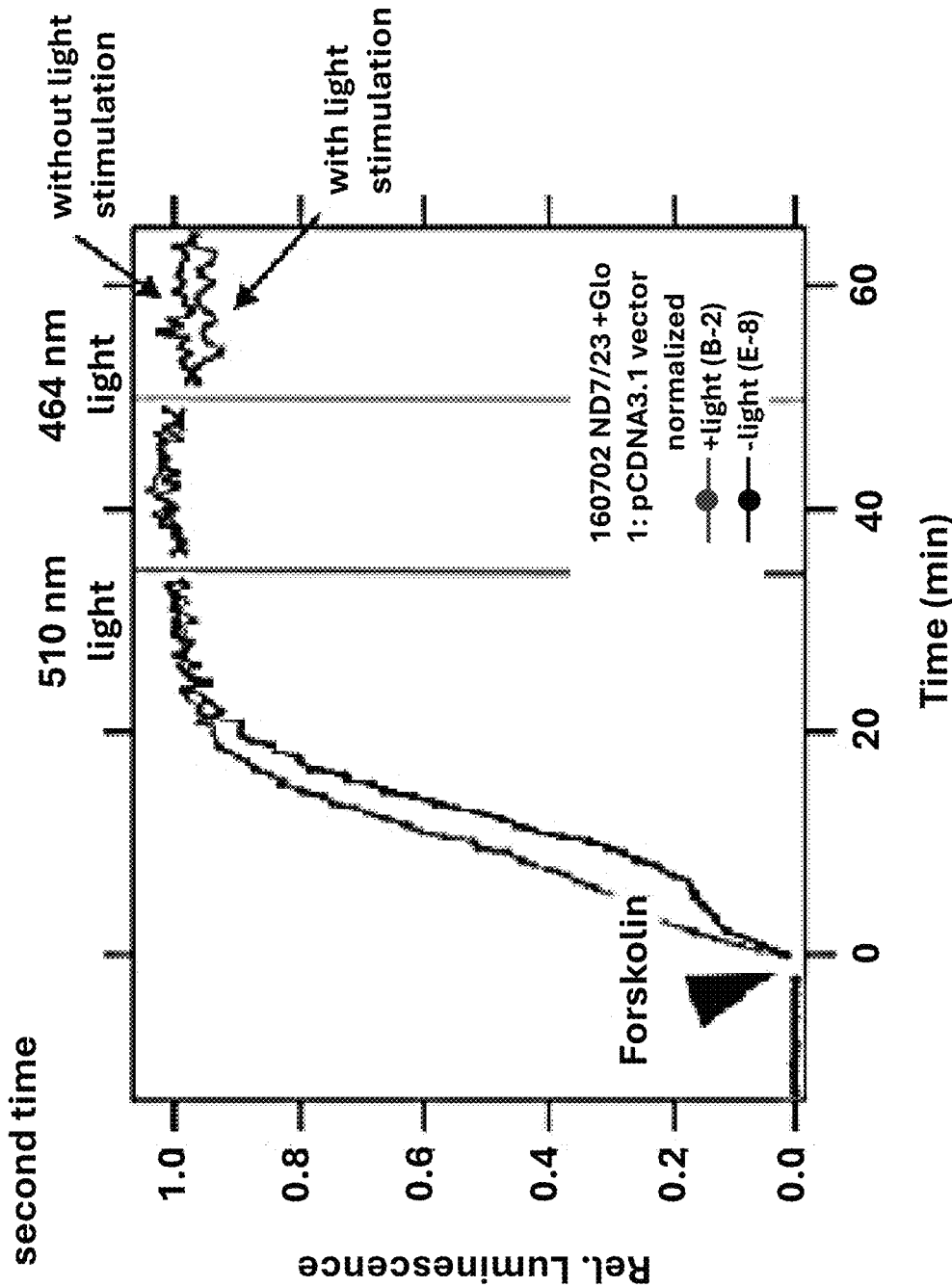
Figure 11C:
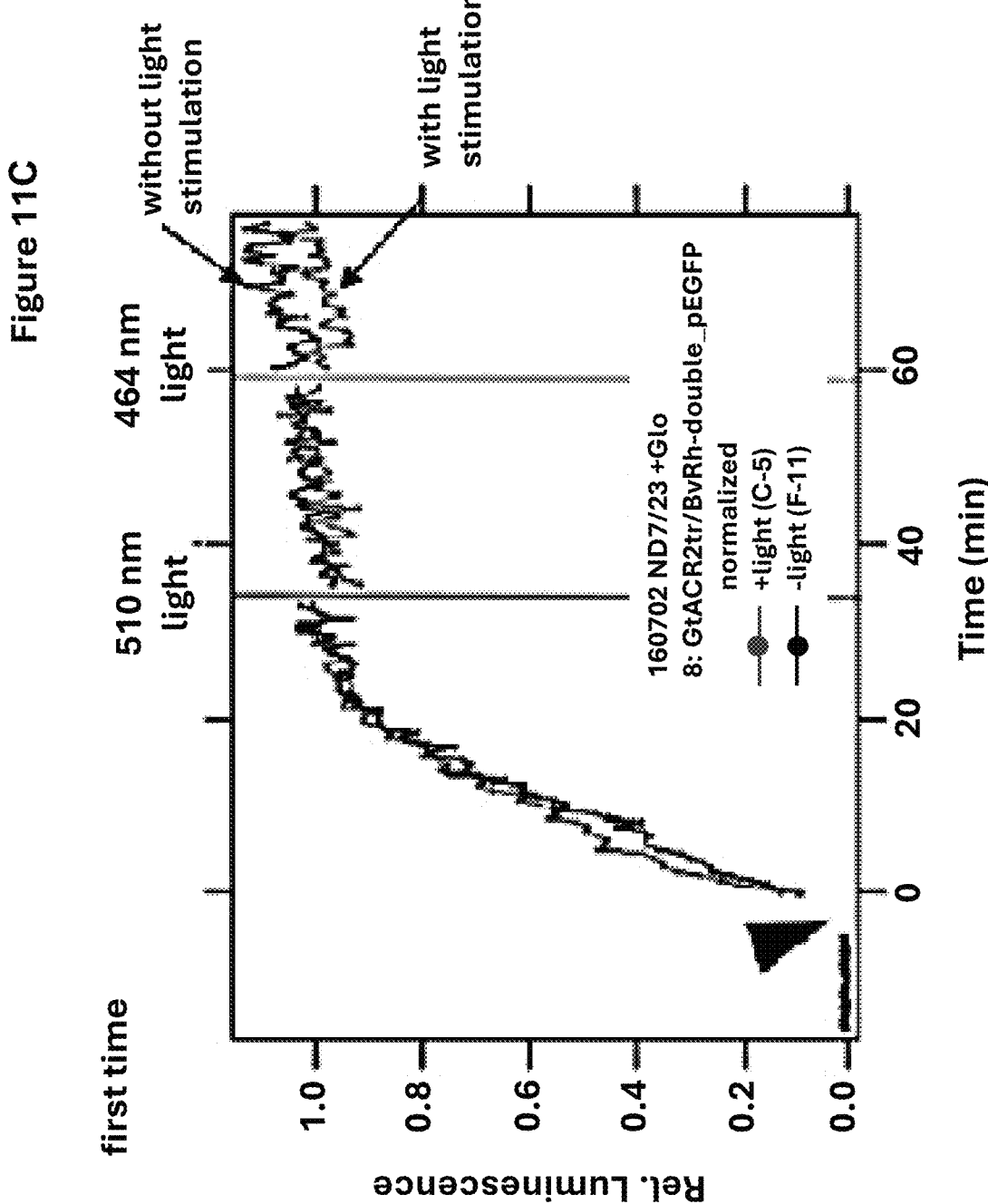
Figure 11D:
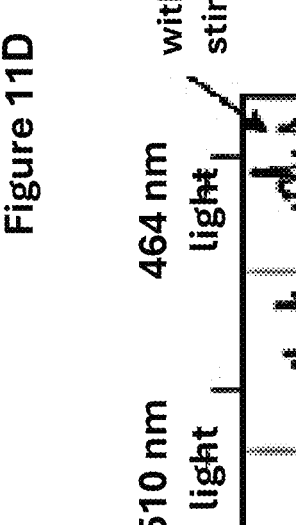

In the control, no difference in brightness was observed between with and without light irradiation (FIG. 11A). On the other hand, in the group to which the GtACR2tr/BvRh-double vector was administered, a decrease in the brightness of GloSensor™ was observed after irradiation with light of 464 nm as compared with the case without irradiation with light (FIG. 11B). The brightness of GloSensor™ is known to correspond to a decrease in intracellular CAMP concentration, which indicates that the intracellular CAMP concentration decreased by light stimulation in the group which to the GtACR2tr/BvRh-double vector was administered. Thus, it can be seen that the GtACR2tr/BvRh-double in which Venus was inserted into the nucleic acid construct of the present disclosure has GPCR activity and can lead to treatment, prevention or suppression of the progress of diseases, disorders or symptoms of the retina, improvement in the visual cognitive behavioral function, and enhancement of the visual function.

(Example 10: Measurement of Ion Transport Capacity of Nucleic Acid Construct Encoding the Chimeric Protein of Ion Channeling Receptor Rhodopsin and G Protein-Coupled Receptor Rhodopsin)

The ion transport capacity was measured by the patch clamp method.

Materials

ND7/23 cells were cultured, and the GtACR2tr/BvRh-double vector, which encodes a chimeric protein of an ion channeling receptor rhodopsin and a G protein-coupled receptor rhodopsin, was gene-introduced. The same amount of GtACR1 vector, which encodes a wild-type Guillardia theta anion channel rhodopsin, was gene-introduced into the control group. The gene-introduced cells were cultured in a culture medium containing retinal.

Measurements

Whole cell patch clamp recording was performed using a patch clamp device, micro glass electrodes, and standard extracellular fluid and intraelectrode fluid. The light irradiation was performed by irradiating light of 500 nm or 480 nm for about 400 ms with a light irradiation device installed in a microscope, and the current response at the time of light irradiation was recorded as a photocurrent. At the time of measurement, the membrane potential was fixed at a potential of −80 mV to 20 mV (20 mV interval) and recording was performed.

Results

Figure 12:
FIG. 12 shows the results of measuring the ion transport capacity of a chimeric protein of an ion channeling receptor rhodopsin and a G protein-coupled receptor rhodopsin using a patch clamp method.

In the control group, photocurrent was generated by light irradiation (FIG. 12). This photocurrent was attenuated over about 2000 ms after the end of light irradiation. In the group into which the GtACR2tr/BvRh-double vector was gene-introduced, a large photocurrent was generated by light irradiation. This photocurrent attenuated in about 1000 ms. From these results, it was further found that GtACR2tr/BvRh-double has a larger ion transport capacity and faster kinetics than the control group.

Since the resting membrane potential of photoreceptor cells is −30 mV to −50 mV, GtACR2tr/BvRh-double is able to hyperpolarize the membrane potential by photostimulation, which can lead to treatment, prevention or suppression of the progress of diseases, disorders or symptoms of the retina, improvement in the visual cognitive behavioral function, and enhancement of the visual function.
(Example 11: Preparation of Nucleic Acid Construct Including Nucleic Acid Sequence Encoding Signal Sequence)

A nucleic acid construct is prepared, which includes a nucleic acid sequence encoding a chimeric protein in which an endoplasmic reticulum export signal different from the endoplasmic reticulum export signal inserted in Example 2 is inserted into the nucleic acid sequence encoding the chimeric protein prepared in Example 1.
(Example 12: Multi-Electrode Array (Multiple Electrode Array: MEA) Test Using Nucleic Acid Construct Including Nucleic Acid Sequence Encoding Signal Sequence)

The effect of a nucleic acid construct including a nucleic acid sequence encoding a signal sequence of Example 11 on the optical response is measured. The descriptions thereof will be provided hereinafter.

Materials and Methods (Animals)
A model of retinitis pigmentosa, rd1 mouse (Pde6b$^{rd1/rd1}$), is used. A C3H/HeJ Jcl mouse having the above mutation is purchased from Japan Claire Co., Ltd.
(Vector Administration)
Blind rd1 mice at the age of 10 weeks or older are administered 1 μl of AAV DJ-CAGGS-Chimeric rhodopsin (GR/BvRh)-WPRE-pA vector (the first nucleic acid construct) or the nucleic acid construct including the nucleic acid sequence encoding a signal sequence of Example 11, at a concentration of $1.0 \times 10^9$ vg/μl by intravitreal injection.

Measurements

The optical response of the mice is measured at or after the 4th week after the injection, at which gene expression peaks. In the multi-electrode array (multi-electrode array: MEA) tests, the optical response of retinal ganglion cells is measured ex vivo by changing the light stimulation intensity of the white LED.

Results

A response is obtained only with light intensity up to $1 \times 10^{14}$ photons/cm$^2$/s stimulation with the first nucleic acid construct, while an improved response is obtained with the nucleic acid construct including a nucleic acid sequence encoding a signal sequence of Example 11. Furthermore, in the stimulus intensity range of $1 \times 10^{14-16}$ photons/cm$^2$/s, the nucleic acid construct including a nucleic acid sequence encoding a signal sequence of Example 11 has a significantly higher firing frequency. In addition, at a stimulus intensity of $1 \times 10^{15}$ photons/cm$^2$/s, the number of firing cells per unit area is also significantly higher.
(Example 13: Wavelength Sensitivity Evaluation Using Nucleic Acid Construct Including Nucleic Acid Sequence Encoding Signal Sequence)

The wavelength sensitivity of the nucleic acid construct including a nucleic acid sequence encoding a signal sequence of Example 11 is evaluated.

The relative luminous efficiency of each wavelength of 11-week-old male rd1 mice, 7 weeks after injection of the nucleic acid construct including a nucleic acid sequence encoding a signal sequence of Example 11, is measured. Light stimulation is performed with a wavelength-specific LED, and the peak firing frequency (Peak Firing Rate (spikes/sec)) of the 25 cells obtained for the reaction is measured at each wavelength. The most responsive value of all wavelengths is set to 1 and the average is measured. The measurement is performed with the light stimulation intensity of $1 \times 10^{14}$ photons/cm/s. As a result of the measurement, it can be seen that the mice injected with the nucleic acid construct including a nucleic acid sequence encoding a signal sequence of Example 11 exhibits the expected wavelength sensitivity.
(Example 14: Evaluation of Visual Evoked Potential Using Nucleic Acid Construct Including Nucleic Acid Sequence Encoding Signal Sequence)

The effect of the nucleic acid construct including a nucleic acid sequence encoding a signal sequence of Example 11 on the visual evoked potential (VEP) is measured. The descriptions thereof will be provided hereinafter.

Materials and Methods (Animals)
A model of retinitis pigmentosa, rd1 mouse (Pde6b$^{rd1/rd1}$), is used. A C3H/HeJ Jcl mouse having the above mutation is purchased from Japan Claire Co., Ltd.
(Vector Administration)
Blind rd1 mice at the age of 10 weeks or older are administered 1 μl of the first nucleic acid construct or the nucleic acid construct including the nucleic acid sequence encoding a signal sequence of Example 11, at a concentration of $1.0 \times 10^9$ vg/μl by intravitreal injection. The control group is administered the same amount of AAV DJ-CAGGS-EGFP-WPRE-pA vector.

Measurements

The VEP is measured at or after the 4th week after the injection, at which gene expression peaks. One week before the measurement, the mice are sedated by administration of three types of mixed anesthesia (midazolam, medetomidine, and butorphanol tarrate are administered at 4 mg/kg, 0.75 mg/kg and 5 mg/kg body weight, respectively), and measurement electrodes are placed in the skull near the visual cortex (1.5 mm forward and 1.5 mm lateral to the lambda suture). After sedating the mice again with the three-anesthesia mix, the evoked potential for a flash stimulus of 0.1 $cds/m^2$ is measured from a white LED installed 3 cm in front of the eyes. As the measuring device, PuREC acquisition system (Mayo, Inazawa, Japan) is used.

Results

A significant increase in amplitude is observed in the mice treated with the nucleic acid construct including the nucleic acid sequence encoding a signal sequence of Example 11 with respect to the control and the mice treated with the first nucleic acid construct. Treatment with the improved construct also shows a visually significant restoration effect at the central level.

(Example 15: Evaluation of Light-Dark Recognition Function Using Nucleic Acid Construct Including Nucleic Acid Sequence Encoding Signal Sequence)

The effect of the nucleic acid construct including a nucleic acid sequence encoding a signal sequence of Example 11 on the light-dark recognition function is measured. The descriptions thereof will be provided hereinafter.

Materials and Methods (Animals)

A model of retinitis pigmentosa, rd1 mouse (Pde6b$^{rd1/rd1}$), is used. A C3H/HeJ Jcl mouse having the above mutation is purchased from Japan Claire Co., Ltd.

(Vector Administration)

Blind rd1 mice at the age of 10 weeks or older are administered 1 μl of the first nucleic acid construct or the nucleic acid construct including the nucleic acid sequence encoding a signal sequence of Example 11, at a concentration of $1.0 \times 10^9$ vg/μl by intravitreal injection. The control group is administered the same amount of AAV DJ-CAGGS-EGFP-WPRE-pA vector.

Measurements

A light-dark transition test (LDT) is conducted at or after the 4th week after the injection, at which gene expression peaked, to evaluate the light-dark recognition function. Mice are placed in a light-dark box (an acrylic case with the width: 415 mm, height: 300 mm, and depth: 250 mm, which is divided into two by a partition, one half of which receives 20 lux of light and the other half of which is a dark room, and the two are connected by a 5×5 mm window) and a video of their 10-minute action is taken. The ratio of staying time in the bright and dark halves is measured and compared.

Results

Healthy mice avoids the bright spot, so that their time spent in the bright spot is shorter, while blind mice (controls)

have a staying time ratio of about half, 0.5. Furthermore, it can be seen that the mice treated by injecting the nucleic acid construct including the nucleic acid sequence encoding a signal sequence of Example 11 have a significantly shorter staying time than the mice treated by injecting the first nucleic acid construct.

(Example 16: Evaluation of Object Recognition Function Using Nucleic Acid Construct Including Nucleic Acid Sequence Encoding Signal Sequence)

The effect of the nucleic acid construct including a nucleic acid sequence encoding a signal sequence of Example 11 on the object recognition function is measured. The descriptions thereof will be provided hereinafter.

Materials and Methods (Animals)

A model of retinitis pigmentosa, rd1 mouse (Pde6b$^{rd1/rd1}$), is used. A C3H/HeJ Jcl mouse having the above mutation is purchased from Japan Claire Co., Ltd.

(Vector Administration)

Blind rd1 mice at the age of 10 weeks or older are administered 1 μl of the nucleic acid construct including the nucleic acid sequence encoding a signal sequence of Example 11, at a concentration of $1.0 \times 10^9$ vg/μl by intravitreal injection. The blind control group is administered the same amount of AAV DJ-CAGGS-EGFP-WPRE-pA vector. Tablet terminals are installed on both side of the space in which the mice are placed, where, at a brightness of 10 lux, one tablet terminal plays a mouse video and the other tablet terminal plays an empty mouse cage. The space designed for the experiment is shown in FIG. 8.

Measurements

The staying time is measured in the area where the video of the mouse is played and the area where the video of the empty mouse cage is played, respectively. The measurement target time is set to be fifteen minutes immediately after the central partition is removed.

Results

The object video side staying time ratio of the blind control group (EGFP) (time spent in the area where the mouse video is played/measurement time) is about 0.5, while it is significantly higher with the nucleic acid construct including the nucleic acid sequence encoding a signal sequence of Example 11.

(Example 17: Preparation of Nucleic Acid Construct Including Nucleic Acid Sequence Encoding Signal Sequence)

A nucleic acid construct is prepared, which includes a nucleic acid sequence encoding a chimeric protein in which an endoplasmic reticulum import signal sequence is inserted into the nucleic acid sequence encoding the chimeric protein prepared in Example 1.

(Example 18: Multi-Electrode Array (Multiple Electrode Array: MEA) Test Using Nucleic Acid Construct Including Nucleic Acid Sequence Encoding Endoplasmic Reticulum Import Signal Sequence)

The effect of a nucleic acid construct including a nucleic acid sequence encoding an endoplasmic reticulum import signal sequence of Example 17 on the optical response is measured. The descriptions thereof will be provided hereinafter.

Materials and Methods (Animals)

A model of retinitis pigmentosa, rd1 mouse (Pde6b$^{rd1/rd1}$), is used. A C3H/HeJ Jcl mouse having the above mutation is used. A C3H/HeJ Jcl mouse having the above mutation is purchased from Japan Claire Co., Ltd.

(Vector Administration)

Blind rd1 mice at the age of 10 weeks or older are administered 1 μl of AAV DJ-CAGGS-Chimeric rhodopsin (GR/BvRh)-WPRE-pA vector (the first nucleic acid construct) or the nucleic acid construct including the nucleic acid sequence encoding an endoplasmic reticulum import signal sequence of Example 19, at a concentration of 1.0× $10^9$ vg/μl by intravitreal injection.

Measurements

The optical response of the mice is measured at or after the 4th week after the injection, at which gene expression peaks. In the multi-electrode array (multi-electrode array: MEA) tests, the optical response of retinal ganglion cells is measured ex vivo by changing the light stimulation intensity of the white LED.

Results

A response is obtained only with light intensity up to $1×10^{14}$ photons/cm/s stimulation with the first nucleic acid construct, while an improved response is obtained with the nucleic acid construct including a nucleic acid sequence encoding an endoplasmic reticulum import signal sequence of Example 17. Furthermore, in the stimulus intensity range of $1×10^{14}$-16 photons/cm$^2$/s, the nucleic acid construct including a nucleic acid sequence encoding an endoplasmic reticulum import signal sequence of Example 17 has a significantly higher firing frequency. In addition, at a stimulus intensity of $1×10^{15}$ photons/cm$^2$/s, the number of firing cells per unit area is also significantly higher.

(Example 19: Wavelength Sensitivity Evaluation Using Nucleic Acid Construct Including Nucleic Acid Sequence Encoding Endoplasmic Reticulum Import Signal Sequence)

The wavelength sensitivity of the nucleic acid construct including a nucleic acid sequence encoding an endoplasmic reticulum import signal sequence of Example 17 is evaluated.

The relative luminous efficiency of each wavelength of 11-week-old male rd1 mice, 7 weeks after injection of the nucleic acid construct including a nucleic acid sequence encoding an endoplasmic reticulum import signal sequence of Example 17 is measured. Light stimulation is performed with a wavelength-specific LED, and the peak firing frequency (Peak Firing Rate (spikes/sec)) of the 25 cells obtained for the reaction is measured at each wavelength. The most responsive value of all wavelengths is set to 1 and the average is measured. The measurement is performed with the light stimulation intensity of $1×10^{14}$ photons/cm$^2$/s. As a result of the measurement, it can be seen that the mice injected with the nucleic acid construct including a nucleic acid sequence encoding an endoplasmic reticulum import signal sequence of Example 17 exhibits the expected wavelength sensitivity.

(Example 20: Evaluation of Visual Evoked Potential Using Nucleic Acid Construct Including Nucleic Acid Sequence Encoding Endoplasmic Reticulum Import Signal Sequence)

The effect of the nucleic acid construct including a nucleic acid sequence encoding an endoplasmic reticulum import signal sequence of Example 17 on the visual evoked potential (VEP) is measured. The descriptions thereof will be provided hereinafter.

Materials and Methods (Animals)

A model of retinitis pigmentosa, rd1 mouse (Pde6b$^{rd1/rd1}$), is used. A C3H/HeJ Jcl mouse having the above mutation is purchased from Japan Claire Co., Ltd.

(Vector Administration)

Blind rd1 mice at the age of 10 weeks or older are administered 1 μl of the first nucleic acid construct or the nucleic acid construct including the nucleic acid sequence encoding an endoplasmic reticulum import signal sequence of Example 17, at a concentration of $1.0×10^9$ vg/μl by intravitreal injection. The control group is administered the same amount of AAV DJ-CAGGS-EGFP-WPRE-pA vector.

Measurements

The VEP is measured at or after the 4th week after the injection, at which gene expression peaks. One week before the measurement, the mice are sedated by administration of three types of mixed anesthesia (midazolam, medetomidine, and butorphanol tarrate are administered at 4 mg/kg, 0.75 mg/kg and 5 mg/kg body weight, respectively), and measurement electrodes are placed in the skull near the visual cortex (1.5 mm forward and 1.5 mm lateral to the lambda suture). After sedating the mice again with the three-types anesthesia, the evoked potential for a flash stimulus of 0.1 cds/m$^2$ is measured from a white LED installed 3 cm in front of the eyes. As the measuring device, PuREC acquisition system (Mayo, Inazawa, Japan) is used.

Results

A significant increase in amplitude is observed in the mice treated with the nucleic acid construct including the nucleic acid sequence encoding an endoplasmic reticulum import signal sequence of Example 17 with respect to the control and the mice treated with the first nucleic acid construct. Treatment with the improved construct also shows a visually significant restoration effect at the central level.

(Example 21: Evaluation of Light-Dark Recognition Function Using Nucleic Acid Construct Including Nucleic Acid Sequence Encoding Endoplasmic Reticulum Import Signal Sequence)

The effect of the nucleic acid construct including a nucleic acid sequence encoding an endoplasmic reticulum import signal sequence of Example 17 on the light-dark recognition function is measured. The descriptions thereof will be provided hereinafter.

Materials and Methods (Animals)

A model of retinitis pigmentosa, rd1 mouse (Pde6b$^{rd1/rd1}$), is used. A C3H/HeJ Jcl mouse having the above mutation is purchased from Japan Claire Co., Ltd.

(Vector Administration)

Blind rd1 mice at the age of 10 weeks or older are administered 1 μl of the first nucleic acid construct or the nucleic acid construct including the nucleic acid sequence encoding an endoplasmic reticulum import signal sequence of Example 17, at a concentration of $1.0×10^9$ vg/μl by intravitreal injection. The control group is administered the same amount of AAV DJ-CAGGS-EGFP-WPRE-pA vector.

Measurements

A light-dark transition test (LDT) is conducted at or after the 4th week after the injection, at which gene expression peaked, to evaluate the light-dark recognition function. Mice are placed in a light-dark box (an acrylic case with the width: 415 mm, height: 300 mm, and depth: 250 mm, which is divided into two by a partition, one half of which receives 10 lux of light and the other half of which is a dark room, and the two are connected by a 5×5 mm window) and a video of their 10-minute action is taken. The ratio of staying time in the bright and dark halves is measured and compared.

Results

Healthy mice avoids the bright spot, so that their time spent in the bright spot is shorter, while blind mice (controls) have a staying time ratio of about half, 0.5. Furthermore, it can be seen that the mice treated by injecting the nucleic acid construct including the nucleic acid sequence encoding an endoplasmic reticulum import signal sequence of Example 17 have a significantly shorter staying time than the mice treated by injecting the first nucleic acid construct.

(Example 22: Evaluation of Object Recognition Function Using Nucleic Acid Construct Including Nucleic Acid Sequence Encoding Endoplasmic Reticulum Import Signal Sequence)

The effect of the nucleic acid construct including a nucleic acid sequence encoding an endoplasmic reticulum import signal sequence of Example 17 on the object recognition function is measured. The descriptions thereof will be provided hereinafter.

Materials and Methods (Animals)

A model of retinitis pigmentosa, rd1 mouse (Pde6b$^{rd1/rd1}$), is used. A C3H/HeJ Jcl mouse having the above mutation is purchased from Japan Claire Co., Ltd.

(Vector Administration)

Blind rd1 mice at the age of 10 weeks or older are administered 1 μl of the nucleic acid construct including the nucleic acid sequence encoding an endoplasmic reticulum import signal sequence of Example 17, at a concentration of 1.0×10$^9$ vg/μl by intravitreal injection. The blind control group is administered the same amount of DJ-CAGGS-EGFP-WPRE-pA vector. Tablet terminals are AAV installed on both side of the space in which the mice are placed, where, at a brightness of 10 lux, one tablet terminal plays a mouse video and the other tablet terminal plays an empty mouse cage. The space designed for the experiment is shown in FIG. 8.

Measurements

The staying time is measured in the area where the video of the mouse is played and the area where the video of the empty mouse cage is played, respectively. The measurement target time is set to be fifteen minutes immediately after the central partition is removed.

Results

The object video side staying time ratio of the blind control group (EGFP) (time spent in the area where the mouse video is played/measurement time) is about 0.5, while it is significantly higher with the nucleic acid construct including the nucleic acid sequence encoding an endoplasmic reticulum import signal sequence of Example 17.

(Example 23: Comparative Example of GPCR Activity Measurement)

A base sequence encoding an amino acid shown in a SEQ ID NO, which is different from the base sequence set forth in SEQ ID NO: 7, is prepared. The nucleic acid construct including the base sequence set forth in SEQ ID NO: 7 and the nucleic acid construct including the base sequence prepared in the present example are gene-introduced into ND7/23 cells.

When the intracellular CAMP concentration is measured using GloSensor™, it can be seen that the CAMP concentration is lower in the cells into which the nucleic acid construct including the nucleotide sequence set forth in SEQ ID NO: 7 has been gene-introduced than in the cells into which the nucleic acid construct prepared in the present example has been gene-introduced. From this, it can be seen that the chimeric rhodopsin encoded by the nucleotide sequence set forth in SEQ ID NO: 7 has stronger GPCR activity than the chimeric rhodopsin encoded by the nucleotide sequence prepared in the present example.

(Example 24: Comparative Example of Ion Transport Capacity)

A base sequence encoding the amino acid set forth in SEQ ID NO: 8, which is different from the base sequence set forth in SEQ ID NO: 7, is prepared. The nucleic acid construct including the base sequence set forth in SEQ ID NO: 7 and the nucleic acid construct including the base sequence prepared in the present example are gene-introduced into ND7/23 cells.

When the ion transport capacity of chimeric rhodopsin encoded by each base sequence is measured by the patch clamp method, it can be seen that the cells into which the nucleic acid construct including the nucleotide sequence set forth in SEQ ID NO: 7 has been gene-introduced have a greater ion transport capacity than the cells into which the nucleic acid construct prepared in the present example has been gene-introduced.

(Example 25: Vector Culture in Adhesive Culture System and Suspension Culture System)

As an adhesive culture system, HEK293T cells or (adhesive) HEK293 cells are cultured. As a suspension culture system, (floating) HEK293 cells or CHO cells are cultured. After culturing, the following plasmids are mixed and the mixture is transfected into cells (PEI: Polyethylenimine; the calcium phosphate method or DEAE-dextran method is used, if necessary).

pAAV-RC (Rep and Cap Genes)

pHelper pAAV-GOI (a Gene of Interest)

A few days after transfection, the cells are collected, and the cells are lysed with a detergent to obtain the drug substance. Thereafter, affinity chromatography, ultracentrifugation, and filter purification are performed for purification to obtain the final product. The purification can be performed based on the method described in Nathalie C and Joshua C., Methods & Clinical Development (2016) 3, 16002.

(Example 26: Multi-Electrode Array (Multiple Electrode Array: MEA) Test Using Nucleic Acid Construct Including Nucleic Acid Sequence Encoding Signal Sequence)

The effect of the nucleic acid sequence set forth in SEQ ID NO: 26 (which encodes the amino acid sequence set forth in SEQ ID NO: 27) on the optical response is measured. The descriptions thereof will be provided hereinafter.

Materials and Methods (Animals)

A model of retinitis pigmentosa, rd1 mouse (Pde6b$^{rd1/rd1}$), is used. A C3H/HeJ Jcl mouse having the above mutation is purchased from Japan Claire Co., Ltd.

(Vector Administration)

Blind rd1 mice at the age of 10 weeks or older are administered 1 μl of AAV 6-CAGGS-Chimeric rhodopsin (GR/BvRh)-WPRE-pA vector (the first nucleic acid construct) or the nucleic acid construct including the nucleic acid sequence set forth in SEQ ID NO: 26, at a concentration of 1.0×10⁸ vg/μl by intravitreal injection.

Measurements

The optical response of the mice is measured at or after the 4th week after the injection, at which gene expression peaks. In the multi-electrode array (multi-electrode array: MEA) tests, the optical response of retinal ganglion cells is measured ex vivo by changing the light stimulation intensity of the white LED.

Results

A response is obtained only with light intensity up to 1×10¹⁴ photons/cm²/s stimulation with the first nucleic acid construct, while an improved response is obtained with the nucleic acid construct including the nucleic acid sequence set forth in SEQ ID NO: 26. Furthermore, in the stimulus intensity range of 1×10¹⁴⁻¹⁶ photons/cm²/s, the nucleic acid construct including the nucleic acid sequence set forth in SEQ ID NO: 26 has a significantly higher firing frequency. In addition, at a stimulus intensity of 1×10¹⁵ photons/cm²/s, the number of firing cells per unit area is also significantly higher.

(Example 27: Wavelength Sensitivity Evaluation Using Nucleic Acid Nucleic Acid Construct Including Sequence Encoding Signal Sequence)

The wavelength sensitivity of the nucleic acid construct including the nucleic acid sequence set forth in SEQ ID NO: 26 is evaluated.

The relative luminous efficiency of each wavelength of 11-week-old male rd1 mice, 7 weeks after injection of the nucleic acid construct including the nucleic acid sequence set forth in SEQ ID NO: 26, is measured. Light stimulation is performed with a wavelength-specific LED, and the peak firing frequency (Peak Firing Rate (spikes/sec)) of the 25 cells obtained for the reaction is measured at each wavelength. The most responsive value of all wavelengths is set to 1 and the average is measured. The measurement is performed with the light stimulation intensity of 1×10¹⁴ photons/cm²/s. As a result of the measurement, it can be seen that the mice injected with the nucleic acid construct including the nucleic acid sequence set forth in SEQ ID NO: 26 exhibits the expected wavelength sensitivity.

(Example 28: Evaluation of Visual Evoked Potential Using Nucleic Acid Construct Including Nucleic Acid Sequence Encoding Signal Sequence)

The effect of the nucleic acid construct including the nucleic acid sequence set forth in SEQ ID NO: 26 on the visual evoked potential (VEP) is measured. The descriptions thereof will be provided hereinafter.

Materials and Methods (Animals)

A model of retinitis pigmentosa, rd1 mouse (Pde6b$^{rd1/rd1}$), is used. A C3H/HeJ Jcl mouse having the above mutation is purchased from Japan Claire Co., Ltd.

(Vector Administration)

Blind rd1 mice at the age of 10 weeks or older are administered 1 μl of the first nucleic acid construct or the nucleic acid construct including the nucleic acid sequence set forth in SEQ ID NO: 26, at a concentration of 1.0×10⁸ vg/μl by intravitreal injection. The control group is administered the same amount of AAV 6-CAGGS-EGFP-WPRE-pA vector.

Measurements

The VEP is measured at or after the 4th week after the injection, at which gene expression peaks. One week before the measurement, the mice are sedated by administration of three types of mixed anesthesia (midazolam, medetomidine, and butorphanol tarrate are administered at 4 mg/kg, 0.75 mg/kg and 5 mg/kg body weight, respectively), and measurement electrodes are placed in the skull near the visual cortex (1.5 mm forward and 1.5 mm lateral to the lambda suture). After sedating the mice again with the three-anesthesia mix, the evoked potential for a flash stimulus of 0.1 cds/m² is measured from a white LED installed 3 cm in front of the eyes. As the measuring device, PuREC acquisition system (Mayo, Inazawa, Japan) is used.

Results

A significant increase in amplitude is observed in the mice treated with the nucleic acid construct including the nucleic acid sequence set forth in SEQ ID NO: 26 with respect to the control and the mice treated with the first nucleic acid construct. Treatment with the improved construct also shows a visually significant restoration effect at the central level.

(Example 29: Evaluation of Light-Dark Recognition Function Using Nucleic Acid Construct Including Nucleic Acid Sequence Encoding Signal Sequence)

The effect of the nucleic acid construct including the nucleic acid sequence set forth in SEQ ID NO: 26 on the light-dark recognition function is measured. The descriptions thereof will be provided hereinafter.

Materials and Methods (Animals)

A model of retinitis pigmentosa, rd1 mouse (Pde6b$^{rd1/rd1}$), is used. A C3H/HeJ Jcl mouse having the above mutation is purchased from Japan Claire Co., Ltd.

(Vector Administration)

Blind rd1 mice at the age of 10 weeks or older are administered 1 μl of the first nucleic acid construct or the nucleic acid construct including the nucleic acid sequence set forth in SEQ ID NO: 26, at a concentration of 1.0×10⁸ vg/μl by intravitreal injection. The control group is administered the same amount of AAV 6-CAGGS-EGFP-WPRE-pA vector.

Measurements

A light-dark transition test (LDT) is conducted at or after the 4th week after the injection, at which gene expression peaked, to evaluate the light-dark recognition function. Mice are placed in a light-dark box (an acrylic case with the width: 415 mm, height: 300 mm, and depth: 250 mm, which is divided into two by a partition, one half of which receives 10 lux of light and the other half of which is a dark room, and the two are connected by a 5×5 mm window) and a video of their 10-minute action is taken. The ratio of staying time in the bright and dark halves is measured and compared.

Results

Healthy mice avoids the bright spot, so that their time spent in the bright spot is shorter, while blind mice (controls) have a staying time ratio of about half, 0.5. Furthermore, it can be seen that the mice treated by injecting the nucleic acid construct including the nucleic acid sequence set forth in SEQ ID NO: 26 have a significantly shorter staying time than the mice treated by injecting the first nucleic acid construct.

(Example 30: Evaluation of Object Recognition Function Using Nucleic Acid Construct Including Nucleic Acid Sequence Encoding Signal Sequence)

The effect of the nucleic acid construct including the nucleic acid sequence set forth in SEQ ID NO: 26 on the object recognition function is measured. The descriptions thereof will be provided hereinafter.

Materials and Methods (Animals)

A model of retinitis pigmentosa, rd1 mouse (Pde6b$^{rd1/rd1}$), is used. A C3H/HeJ Jcl mouse having the above mutation is purchased from Japan Claire Co., Ltd.

(Vector Administration)

Blind rd1 mice at the age of 10 weeks or older are administered 1 µl of the nucleic acid construct including the nucleic acid sequence set forth in SEQ ID NO: 26, at a concentration of $1.0×10^8$ vg/µl by intravitreal injection. The blind control group is administered the same amount of AAV 6-CAGGS-EGFP-WPRE-pA vector. Tablet terminals are installed on both side of the space in which the mice are placed, where, at a brightness of 10 lux, one tablet terminal plays a mouse video and the other tablet terminal plays an empty mouse cage. The space designed for the experiment is shown in FIG. 8.

Measurements

The staying time is measured in the area where the video of the mouse is played and the area where the video of the empty mouse cage is played, respectively. The measurement target time is set to be fifteen minutes immediately after the central partition is removed.

Results

The object video side staying time ratio of the blind control group (EGFP) (time spent in the area where the mouse video is played/measurement time) is about 0.5, while it is significantly higher with the nucleic acid construct including the nucleic acid sequence set forth in SEQ ID NO: 26.

(Note)

As described above, the present disclosure has been illustrated using the preferred embodiments of the present disclosure; however, it is understood that the scope of the present disclosure should be interpreted only by the Claims thereof. It is understood that the contents of patents, patent applications and documents cited herein should be incorporated herein by reference in the same way that the contents themselves thereof are specifically described herein. The present application claims priority to Japanese Patent Application No. 2019-167553 (filed on Sep. 13, 2019) filed with the Japan Patent Office, the contents of which are incorporated herein by reference in the same manner as all of them are described in the present specification.

INDUSTRIAL APPLICABILITY

New nucleic acid constructs of chimeric rhodopsin have been provided for the prevention and the suppression of progress of retinal disease, for the visual cognitive behavioral functions visual cognitive behavioral functions (e.g., improvement in light-dark determination functions, improvement in bright spot evading functions, and/or crisis avoidance functions) and for enhancing the object recognition function and the visual acuity. Techniques are provided that are applicable to industries (pharmaceuticals, etc.) based on such techniques as described above.

SEQUENCE LISTING FREE TEXT

SEQ ID NO: 1: an example of the nucleic acid sequence consisting of a chimeric rhodopsin (GR/BvRh) and an endoplasmic reticulum export signal sequence SEQ ID NO: 2: an example of the amino acid sequence consisting of a chimeric rhodopsin (GR/BvRh) and an endoplasmic reticulum export signal sequence SEQ ID NO: 3: an example of the nucleic acid sequence consisting of a chimeric rhodopsin (GR/BvRh), an endoplasmic reticulum export signal sequence, and a FLAG tag SEQ ID NO: 4: an example of the amino acid sequence consisting of a chimeric rhodopsin (GR/BvRh), an endoplasmic reticulum export signal sequence, and a FLAG tag SEQ ID NO: 5: an example of the amino acid sequence of a chimeric rhodopsin (GR/BvRh)

SEQ ID NO: 6: an example of the nucleic acid sequence of a chimeric rhodopsin (GtACR2/BvRh)

SEQ ID NO: 7: an example of the nucleic acid sequence of a chimeric rhodopsin (GtACR2/BvRh)

SEQ ID NO: 8: an example of the amino acid sequence of a chimeric rhodopsin (GtACR2/BvRh)

SEQ ID NO: 9: the nucleic acid sequence of a human rhodopsin (huRh)

SEQ ID NO: 10: the amino acid sequence of a human rhodopsin (huRh)

SEQ ID NO: 11: the nucleic acid sequence of a bovine rhodopsin (BvRh)

SEQ ID NO: 12: the amino acid sequence of a bovine rhodopsin (BvRh)

SEQ ID NO: 13: the nucleic acid sequence of Gloeobacter *violaceus* Rhodopsin (GR)

SEQ ID NO: 14: the amino acid sequence of Gloeobacter *violaceus* Rhodopsin (GR)

SEQ ID NO: 15: the nucleic acid sequence of Guillardia theta anion channelrhodopsin2 (GtACR2)

SEQ ID NO: 16: the amino acid sequence of Guillardia theta anion channelrhodopsin2 (GtACR2)

SEQ ID NO: 17: an example of the nucleic acid sequence of the second loop on the cytoplasm side of the G protein-coupled receptor rhodopsin SEQ ID NO: 18: an example of the nucleic acid sequence of the second loop on the cytoplasm side of the G protein-coupled receptor rhodopsin SEQ ID NO: 19: an example of the amino acid sequence of the second loop on the cytoplasm side of the G protein-coupled receptor rhodopsin (corresponding to SEQ ID NO: 18)

SEQ ID NO: 20: an example of the nucleic acid sequence of the third loop on the cytoplasm side of the G protein-coupled receptor rhodopsin SEQ ID NO: 21: an example of the nucleic acid sequence of the third loop on the cytoplasm side of the G protein-coupled receptor rhodopsin SEQ ID NO: 22: an example of the amino acid sequence of the third loop on the cytoplasm side of the G protein-coupled receptor rhodopsin SEQ ID NO: 23: an example of the nucleic acid sequence of the chimeric rhodopsin (GR/BvRh) (corresponding to SEQ ID NO: 8), where the start codon corresponds to nucleotides 43-45 and the stop codon corresponds to nucleotides 994-996

SEQ ID NO: 24: an example of the nucleic acid sequence of the second loop on the cytoplasm side of the G protein-coupled receptor rhodopsin SEQ ID NO: 25: an example of the amino acid sequence of the second loop on the cytoplasm side of the G protein-coupled receptor rhodopsin (corresponding to SEQ ID NO: 24)

SEQ ID NO: 26: an example of the nucleic acid sequence consisting of a chimeric rhodopsin (GR/BvRh) and an endoplasmic reticulum export signal sequence SEQ ID NO: 27: an example of the amino acid sequence consisting of a chimeric rhodopsin (GR/BvRh) and an endoplasmic reticulum export signal sequence

---

The invention claimed is:

1. A nucleic acid comprising:
   (i) a nucleic acid sequence encoding a chimeric protein, wherein said chimeric protein comprises a microbial-derived ion-transporting receptor rhodopsin and an animal-derived G protein-coupled receptor rhodopsin; and
   (ii) a nucleic acid sequence encoding an endoplasmic reticulum export signal sequence; wherein said nucleic acid comprises nucleotides 27 to 1037 of the nucleic acid sequence set forth in SEQ ID NO: 1.

2. The nucleic acid of claim 1, further comprising a nucleic acid sequence encoding a FLAG tag, wherein the nucleic acid comprises the nucleic acid sequence set forth in SEQ ID NO: 3.

3. A polypeptide encoded by the nucleic acid of claim 1, wherein the polypeptide comprises the amino acid sequence set forth in SEQ ID NO: 2.

4. A nucleic acid construct comprising the nucleic acid of claim 1 and a nucleic acid operably linked to the nucleic acid for enabling expression in a cell.

5. A vector comprising the nucleic acid construct of claim 4.

6. The vector of claim 5, wherein the vector is a viral vector.

7. The vector of claim 6, wherein the vector is a retroviral vector, a lentiviral vector, or an adeno-associated virus (AAV) vector.

8. The vector of claim 7, wherein the vector is an AAV vector.

9. The vector of claim 8, wherein the AAV vector is AAV-DJ, AAV-2 or AAV-6.

10. A cell comprising one or more of the nucleic acid of claim 1, a polypeptide encoded by the nucleic acid of claim 1, or a nucleic acid construct comprising the nucleic acid of claim 1 and a nucleic acid operably linked to the nucleic acid for enabling expression in the cell.

11. The cell of claim 10, wherein the cell is a retinal cell.

12. A pharmaceutical composition comprising an effective amount of one or more of the nucleic acid of claim 1, a polypeptide encoded by the nucleic acid of claim 1, or a nucleic acid construct comprising the nucleic acid of claim 1 and a nucleic acid operably linked to the nucleic acid for enabling expression in a cell, and a pharmacologically acceptable carrier.

13. A method for treating retinitis pigmentosa in a subject in need or at risk thereof, comprising administering to the subject an effective amount of (i) the nucleic acid of claim 1; (ii) a polypeptide encoded by the nucleic acid of claim 1; (iii) a nucleic acid construct comprising the nucleic acid of claim 1 and a nucleic acid operably linked to the nucleic acid for enabling expression in a cell; or (iv) a cell comprising one or more of the nucleic acid of claim 1; a polypeptide encoded by the nucleic acid of claim 1; or a nucleic acid construct comprising the nucleic acid of claim 1 and a nucleic acid operably linked to the nucleic acid for enabling expression in the cell.

14. A method for improving a visual cognitive behavioral function in a subject in need thereof, comprising administering to the subject an effective amount of (i) the nucleic acid of claim 1; (ii) a polypeptide encoded by the nucleic acid of claim 1; (iii) a nucleic acid construct comprising the nucleic acid of claim 1 and a nucleic acid operably linked to the nucleic acid for enabling expression in a cell; or (iv) a cell comprising one or more of the nucleic acid of claim 1; a polypeptide encoded by the nucleic acid of claim 1; or a nucleic acid construct comprising the nucleic acid of claim 1 and a nucleic acid operably linked to the nucleic acid for enabling expression in a cell.

15. A method for enhancing a visual function in a subject in need thereof, comprising administering to the subject an effective amount of (i) the nucleic acid of claim 1; (ii) a polypeptide encoded by the nucleic acid of claim 1; (iii) a nucleic acid construct comprising the nucleic acid of claim 1 and a nucleic acid operably linked to the nucleic acid for enabling expression in a cell; or (iv) a cell comprising one or more of the nucleic acid of claim 1; a polypeptide encoded by the nucleic acid of claim 1; or a nucleic acid construct comprising the nucleic acid of claim 1 and a nucleic acid operably linked to the nucleic acid for enabling expression in a cell.

16. A method for enhancing an object recognition function in a subject in need thereof, comprising administering to the subject an effective amount of (i) the nucleic acid of claim 1; (ii) a polypeptide encoded by the nucleic acid of claim 1; (iii) a nucleic acid construct comprising the nucleic acid of claim 1 and a nucleic acid operably linked to the nucleic acid for enabling expression in a cell; or (iv) a cell comprising one or more of the nucleic acid of claim 1; a polypeptide encoded by the nucleic acid of claim 1; or a nucleic acid construct comprising the nucleic acid of claim 1 and a nucleic acid operably linked to the nucleic acid for enabling expression in a cell.

17. A nucleic acid comprising a nucleic acid sequence encoding a chimeric protein, wherein said chimeric protein comprises an algal or microbial ion channeling receptor rhodopsin and an animal-derived G protein-coupled receptor rhodopsin, wherein said nucleic acid comprises the nucleic acid sequence set forth in SEQ ID NO: 7.

* * * * *